US012781203B2

(12) United States Patent
Ai et al.

(10) Patent No.: US 12,781,203 B2
(45) **Date of Patent: *Nov. 3, 2026**

(54) ATP-INDEPENDENT BIOLUMINESCENT REPORTER VARIANTS TO IMPROVE IN VIVO IMAGING

(71) Applicant: University of Virginia Patent Foundation, Charlottesville, VA (US)

(72) Inventors: Huiwang Ai, Crozet, VA (US); Hsien-Wei Yeh, Seattle, WA (US); Ying Xiong, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 926 days.

This patent is subject to a terminal disclaimer.

(21) Appl. No.: 17/434,351

(22) PCT Filed: Feb. 27, 2020

(86) PCT No.: PCT/US2020/020144

§ 371 (c)(1),
(2) Date: Aug. 26, 2021

(87) PCT Pub. No.: WO2020/176755

PCT Pub. Date: Sep. 3, 2020

(65) Prior Publication Data

US 2022/0259574 A1 Aug. 18, 2022

Related U.S. Application Data

(60) Provisional application No. 62/811,129, filed on Feb. 27, 2019.

(51) Int. Cl.
*C12N 9/02* (2006.01)
*C12N 15/63* (2006.01)
*G01N 33/542* (2006.01)

(52) U.S. Cl.
CPC .......... *C12N 9/0069* (2013.01); *C12N 15/63* (2013.01); *G01N 33/542* (2013.01); *C12Y 113/12005* (2013.01)

(58) Field of Classification Search
CPC .... C12N 9/0069; C12N 15/63; G01N 33/542; G01N 33/5041; G01N 33/5023; G01N 33/5088; C12Y 113/12005; C07D 487/04; C12Q 1/66
See application file for complete search history.

(56) References Cited

U.S. PATENT DOCUMENTS

| | | | |
|---|---|---|---|
| 4,554,101 A | 11/1985 | Hopp | |
| 5,034,506 A | 7/1991 | Summerton et al. | |
| 8,557,970 B2 | 10/2013 | Encell et al. | |
| 8,669,103 B2 | 3/2014 | Binkowski et al. | |
| 9,777,311 B2 | 10/2017 | Encell et al. | |
| 9,840,730 B2 | 12/2017 | Binkowski et al. | |
| 9,951,373 B2 | 4/2018 | Binkowski et al. | |
| 10,202,584 B2 | 2/2019 | Ai et al. | |
| 2004/0131637 A1 | 7/2004 | Chatfield | |
| 2016/0376332 A1 | 12/2016 | Lin et al. | |
| 2018/0057801 A1* | 3/2018 | Ai ................. | C12Y 113/12007 |
| 2018/0327810 A1 | 11/2018 | Binkowski et al. | |
| 2026/0077068 A1 | 3/2026 | Ai et al. | |

FOREIGN PATENT DOCUMENTS

| | | |
|---|---|---|
| WO | 9617951 A2 | 6/1996 |
| WO | WO 2020/176755 A1 | 9/2020 |

OTHER PUBLICATIONS

Branchini et al., Biochemistry, 10.1021/bi7015052, cited on attached Form PTO-892; herein referred to as Branchini) (Year: 2007).*
Kizer, Lance, et al. "Application of functional genomics to pathway optimization for increased isoprenoid production." Applied and environmental microbiology 74.10 (2008): 3229-3241. (Year: 2008).*
Prather, Kristala L. Jones, and Collin H. Martin. "De novo biosynthetic pathways: rational design of microbial chemical factories." Current opinion in biotechnology 19.5 (2008): 468-474 (Year: 2008).*
K Singh, Raushan, et al. "Protein engineering approaches in the post-genomic era." Current Protein and Peptide Science 19.1 (2018): 5-15. (Year: 2018).*
Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*
Yeh et al (Date Published: May 17, 2019, HHS Public Access) {herein Yeh} (Year: 2019).*
International Search Report and Written Opinion corresponding to International Patent Application No. PCT/US2020/020144 dated Jul. 24, 2020.
Yeh (2017) "Red-Shifted Luciferase-Luciferin Pairs for Enhanced Bioluminescence Imaging," Nat. Methods, vol. 14, No. 10, pp. 971-974, Abstract.
Adamczyk, M., et al., "Synthesis of 3,7-dihydroimidazo[1,2a]pyrazine-3-ones and their chemiluminescent properties," Tetrahedron, vol. 59, 2003, pp. 8129-8142.
Adams, S.T., et al., "Beyond D-luciferin: expanding the scope of bioluminescence imaging in vivo," Curr. Opin. Chern. Biol., 2014, vol. 21, pp. 112-120.

(Continued)

*Primary Examiner* — Manjunath N Rao
*Assistant Examiner* — Erica Nicole Jones-Foster
(74) *Attorney, Agent, or Firm* — CANTOR COLBURN LLP

(57) ABSTRACT

Provided herein are chemically modified luciferase substrates for spectrally shifted emission and enhanced water solubility. Provided herein are engineered luciferases. Moreover, provided herein are new ATP-independent bioluminescent reporters which have improved biochemical and photophysical properties and are expected to have broad applications. Finally, provided herein are spectral-resolved triple-color bioluminescent systems, suitable for flexible and convenient approaches to monitor multiple biological events in either qualitative or quantitative manners.

2 Claims, 31 Drawing Sheets

Specification includes a Sequence Listing.

(56) References Cited

OTHER PUBLICATIONS

Altschul, S.F., et al., (1990), "Basic local alignment search tool," J Mol Biol, vol. 215, pp. 403-410.
Badr, C. E., et al., "Real-Time Monitoring of Nuclear Factor κB Activity in Cultured Cells and in Animal Models," Molecular Imaging, 2009, vol. 8, pp. 278-290.
Bindels, D. S., et al., "mScarlet: a bright monomeric red fluorescent protein for cellular imaging," Nat. Methods, vol. 14, 2017, pp. 13.
Bird, R.E., et al. (1988) "Single-chain antigen-binding proteins", Science, vol. 242, pp. 423-426.
Bowie, J.U., et al., "Deciphering the message in protein sequences: tolerance to amino acid substitutions", Science, vol. 24, No. 7, 1990, pp. 1306-1310.
Branchini, B. R., et al., "A Firefly Luciferase Dual Color Bioluminescence Reporter Assay Using Two Substrates to Simultaneously Monitor Two Gene Expression Events," Sci Rep-Uk, 2018, vol. 8, pp. 7.
Chou, P.C., et al., "Prediction of protein conformation", Biochemistry, vol. 13, 1974, pp. 222-245.
Chou, P.Y., et al., "Empirical predictions of protein conformation", Ann Rev Biochem, vol. 47, 1978, pp. 251-276.
Chou, P.Y., et al., "Prediction of beta-turns", Biophys J., vol. 26, 1979, pp. 367-384.
Chu, J., et al., "A bright cyan-excitable orange fluorescent protein facilitates dual-emission microscopy and enhances bioluminescence imaging in vivo," Nat. Biotechnol., vol. 34, 2016, pp. 760-767.
Greenwald, E. C., et al., "Genetically Encoded Fluorescent Biosensors Illuminate the Spatiotemporal Regulation of Signaling Networks," Chemical reviews, vol. 118, 2018, pp. 11707-11794.
Haddock, S. H., et al., "Bioluminescence in the sea," Ann Rev Mar Sci, vol. 2, 2010, pp. 443-493.
Hall, M. P., et al., "Engineered luciferase reporter from a deep sea shrimp utilizing a novel imidazopyrazinone substrate," ACS Chern. Biol., vol. 7, 2012, pp. 1848-1857.
Heise, K., et al., "Dual Luciferase Assay for Secreted Luciferases Based on Gaussia and NanoLuc," Assay and Drug Development Technologies, 2013, vol. 11, pp. 244-252.
Henikoff, S., et al., "Amino acid substitution matrices from protein blocks," Proc Natl Acad Sci USA, vol. 89, 1992, pp. 10915-10919.
Hill, C. S., et al., "Differential activation of c-fos promoter elements by serum, lysophosphatidic acid, G proteins and polypeptide growth factors," Embo J., 1995, vol. 14, pp. 5037-5047.
Houston, J.S., et al., (1988) "Protein engineering of antibody binding sites: recovery of specific activity in an anti-digoxin single-chain Fv analogue produced in *Escherichia coli*," Proc Natl Acad Sci USA, vol. 85, pp. 5879-5883.
Inagaki, S., et al., "Genetically encoded bioluminescent voltage indicator for multi-purpose use in wide range of bioimaging," Scientific reports, 2017, vol. 7, 42398, 11 pages.
Inouye, S., et al., "Luminescence enhancement of the catalytic 19 kDa protein (KAZ) of Oplophorus luciferase by three amino acid substitutions," Biochem. Biophys. Res. Commun., vol. 445, 2014, pp. 157-162.
Inouye, S., et al., "Overexpression, purification and characterization of the catalytic component of Oplophorus luciferase in the deep-sea shrimp, *Oplophorus gracilirostris*," Protein Expr. Purif., vol. 56, 2007, pp. 261-268.
International Preliminary Report on Patentability received in PCT Application No. PCT/US2020/020144 mailed on Sep. 10, 2021, 7 pages.
Invitation to Pay Additional Fees received in PCT Application No. PCT/US2020/020144 mailed on May 19, 2020, 2 pages.
Iwano, S., et al., "Single-cell bioluminescence imaging of deep tissue in freely moving animals," Science, vol. 359, 2018, pp. 935-939.
Jedinak, L., et al., "The Suzuki-Miyaura Cross-Coupling Reaction of Halogenated Aminopyrazoles: Method Development, Scope, and Mechanism of Dehalogenation Side Reaction," J. Org. Chem., vol. 82, 2017, pp. 157-169.
Jiang, T. Y., et al., "New bioluminescent coelenterazine derivatives with various C-6 substitutions," Org. Biomol. Chem., vol. 15, 2017, pp. 7008-7018.
Johnson, M.S., et al., "A Structural Basis for Sequence Comparisons: An Evaluation of Scoring Methodologies", J. Mol Biol., vol. 233, 1993, pp. 716-738.
Jones, K. A., "Orthogonal Luciferase-Luciferin Pairs for Bioluminescence Imaging," Journal of the American Chemical Society, 2017, vol. 139, pp. 2351-2358.
Karlin, S., et al., "Applications and statistics for multiple high-scoring segments in molecular sequences", Proc Natl Acad Sci USA, 1993, vol. 90, pp. 5873-5877.
Kerns, E. H., et al., "In vitro solubility assays in drug discovery," Curr. Drug Metab., vol. 9, 2008, pp. 879-885.
Kotlobay, A. A., "Genetically encodable bioluminescent system from fungi," Proceedings of the National Academy of Sciences of the United States of America, 2018, vol. 115, pp. 12728-12732.
Kyte, J., et al., "A simple method for displaying the hydropathic character of a protein", J Mol Biol, vol. 157, 1982, pp. 105-132.
Loening, A.M., et al., "Red-shifted Renilla reniformis luciferase variants for imaging in living subjects," Nat Methods, 2007, vol. 4, pp. 641-643.
Mezzanotte, L., et al., (2017) "In Vivo Molecular Bioluminescence Imaging: New Tools and Applications," Trends Biotechnol., vol. 35, pp. 640-652.
Mezzanotte, L., et al., "A new multicolor bioluminescence imaging platform to investigate NF-κB activity and apoptosis in human breast cancer cells," Plos One, 2014, vol. 9, e85550, pp. 12.
Mezzanotte, L., et al., "Sensitive Dual Color In Vivo Bioluminescence Imaging Using a New Red Codon Optimized Firefly Luciferase and a Green Click Beetle Luciferase," Plos One 2011, vol. 6, e19277, pp. 9.
Michelini, E., et al., "Cell-based assays: fuelling drug discovery," Anal Bioanal Chem, 2010, vol. 398, pp. 227-238.
Michelini, E., et al., "Spectral-Resolved Gene Technology for Multiplexed Bioluminescence and High-Content Screening," Anal Chem, 2008, vol. 80, pp. 260-267.
Miraglia, L. J., et al., "Seeing the light: luminescent reporter gene assays," Comb Chem High Throughput Screen, 2011, vol. 14, pp. 648-657.
Morse, D., et al., "A water-soluble coelenterazine for sensitive in vivo imaging of coelenterate luciferases," Mol. Ther., vol. 20, 2012, pp. 692-693.
Morton, C. L., et al., "Establishment of human tumor xenografts in immunodeficient mice," Nat. Protoc, vol. 2, 2007, pp. 247-250.
Nakajima, Y., et al., "Multicolor luciferase assay system: one-step monitoring of multiple gene expressions with a single substrate," Biotechniques 2005, vol. 38, pp. 891-894.
Naylor, L.H., "Reporter gene technology: the future looks bright," Biochem Pharmacol., 1999, vol. 58, pp. 749-757.
Needleman, S.B., et al., "A general method applicable to the search for similarities in the amino acid sequence of two proteins," J Mol Biol, 1970, vol. 48, pp. 443-453.
Nguyen, T., et al., "The Nrf2-antioxidant response element signaling pathway and its activation by oxidative stress," J Bioi Chem 2009, vol. 284, pp. 13291-13295.
Nielsen, P.E., et al., (1991) "Sequence-selective recognition of DNA by strand displacement with a thymine-substituted polyamide," Science, vol. 254, pp. 1497-1500.
Oh, Y., et al., "An orange calcium-modulated bioluminescent indicator for non-invasive activity imaging," Nat Chem Biol., 2019, vol. 15 (5), pp. 433-436.
Ohmiya, Y., "Simultaneous multicolor luciferase reporter assays for monitoring of multiple genes expressions," Comb Chem High Throughput Screen, 2015, vol. 18, pp. 937-945.
Pearson, W.R., et al., "Improved tools for biological sequence comparison", Proc Natl Acad Sci USA, vol. 85, 1988, pp. 2444-2448.
Qian, Y., et al., "A Bioluminescent Ca(2+) Indicator Based on a Topological Variant of GCaMP6s," ChemBioChem., 2018, vol. 20, pp. 516-520.

(56) References Cited

OTHER PUBLICATIONS

Rathbun, C. M., et al., "Parallel Screening for Rapid Identification of Orthogonal Bioluminescent Tools," ACS Cent Sci., 2017, vol. 3, pp. 1254-1261.
Rodriguez, E. A., et al., "The Growing and Glowing Toolbox of Fluorescent and Photoactive Proteins," Trends Biochem. Sci., vol. 42, 2017, pp. 111-129.
Rogers, K. L., et al., "Non-invasive in vivo imaging of calcium signaling in mice," PLoS One, vol. 2, 2007, e974, pp. 15.
Rumyantsev, K. A., et al., "Near-infrared bioluminescent proteins for two-color multimodal imaging," Sci Rep-Uk, 2016, vol. 6, 36588, pp. 10.
Sadikot, R. T., et al., "Bioluminescence imaging," Proc. Am. Thorac. Soc., vol. 2, 537-540, 2005, pp. 537-540.
Saito, R., et al., "Synthesis and luminescence properties of near-infrared N-heterocyclic luciferin analogues for in vivo optical imaging," Bulletin of the Chemical Society of Japan, doi:10.1246/bcsj.20180350, vol. 92, Dec. 15, 2018, pp. 608-618.
Salin, K., et al., "Variation in the link between oxygen consumption and ATP production, and its relevance for animal performance," P Roy Soc B-Biol Sci, vol. 282, 2015, pp. 14-22.
Shakhmin, A., et al., "Coelenterazine analogues emit red-shifted bioluminescence with NanoLuc," Org Biomol Chem., vol. 15, 2017, pp. 8559-8567.
Shakhmin, A., et al., "Three Efficient Methods for Preparation of Coelenterazine Analogues," Chem-Eur J., vol. 22, 2016, pp. 10369-10375.
Smith, T.F., et al., (1981) "Comparison of biosequences," Advances in Applied Mathematics, vol. 2, pp. 482-489.
Suzuki, K., et al., "Five colour variants of bright luminescent protein for real-time multicolour bioimaging," Nat. Commun., vol. 7, Article No. 13718, 2016, 10 pages.
Suzuki, K., et al., "Recent progress in expanding the chemiluminescent toolbox for bioimaging," Curr Opin Biotech, 2017, vol. 48, pp. 135-141.
Tantama, M., et al., "Imaging energy status in live cells with a fluorescent biosensor of the intracellular ATP-to-ADP ratio," Nat. Commun. vol. 4, 2013, Article No. 2550, pp. 11.
Teranishi, K., "Solubilizing coelenterazine in water with hydroxypropyl-beta-cyclodextrin," Biosci. Biotechnol. Biochem. vol. 61, 1997, pp. 1219-1220.
Thorne, N., et al., "Illuminating insights into firefly luciferase and other bioluminescent reporters used in chemical biology," Auldl, D. S. Chemistry & Biology, 2010, vol. 17, pp. 646-657.
Weissleder, R., et al., "Shedding light onto live molecular targets," Nat. Med., 2003, vol. 9, pp. 123-128.
Wu, C., et al., "Chemi- and bioluminescence of coelenterazine analogues with a conjugated group at the C-8 position," Tetrahedron Lett, 2001, vol. 42, pp. 2997-3000.
Yao, Z., et al., "Advances in bioluminescence imaging: new probes from old recipes," Curr. Opin. Chern. Bioi., vol. 45, 2018, pp. 148-156.
Yasunaga, M., et al., "Dual-color bioluminescence imaging assay using green- and red-emitting beetle luciferases at subcellular resolution," Anal Bioanal Chem, 2014, vol. 406, pp. 5735-5742.
Yeh, H. W., et al., "Development and Applications of Bioluminescent and Chemiluminescent Reporters and Biosensors," Annu. Rev. Anal. Chem., vol. 12, 2019, pp. 129-150.
Yeh, H. W., et al., "Identification of Factors Complicating Bioluminescence Imaging," Biochemistry minor revision, as of Feb. 1, 2019, reprint from BioRxiv: https:// doi.org/10.1101/511501, pp. 12 (Jan. 22, 2019).
Zinn, K. R., et al., "Noninvasive bioluminescence imaging in small animals," ILAR J., vol. 49, 2008, pp. 103-115.
Alpuche Aranda, et al.; "*Salmonella typhimurium* activates virulence gene transcription within acidified macrophage phagosomes"; PNAS, vol. 89, Issue No. 21; pp. 10079-10083 (1992).
Altschul, S et al.; "Gapped BLAST and PSI-BLAST: a new generation of protein database search programs"; Nucleic Acids Research, vol. 25, Issue No. 17; pp. 3389-3402 (1997).
Chenna, et al.; "Multiple sequence alignment with the Clustal series of programs"; Nucleic Acids Research, vol. 31, Issue No. 13; pp. 3497-3500 (2003).
De Boer, H. et al.; "The tac promoter: a functional hybrid derived from the trp and lac promoters"; PNAS, vol. 80, Issue No. 1; pp. 21-25; DOI:10.1073/pnas.80.1.21 (1983).
Dunstan, S. et al.; "Use of In Vivo-Regulated Promoters to Deliver Antigens from Attenuated *Salmonella enterica* var. *Typhimurium*"; Infect Immun, vol. 67; pp. 5133-5141; DOI:10.1128/iai.67.10.5133-5141.1999 (1999).
Genbank Accession No. AX798183, "Sequence 59 from Patent WO03054201"; Oct. 8, 2003.
Genbank Accession No. AX798961, "Sequence 53 from Patent WO03054189"; Oct. 8, 2003.
Genbank Accession No. AX798980, "Sequence 72 from Patent WO03054189"; Oct. 8, 2003.
Gornall, A. et al.; "Determination of Serum Proteins by Means of the Biuret Reaction"; Journal of Biological Chemistry, vol. 177; pp. 751-766 (1948).
Melton, D., et al.; "Efficient in vitro synthesis of biologically active RNA and RNA hybridization probes from plasmids containing a bacteriophage SP6 promoter"; Nucleic Acids Res, vol. 12, Issue No. 18; pp. 7035-7056; DOI: 10.1093/nar/12.18.7035 (1984).
Notredame, et al.; "T-Coffee: A Novel Method for Fast and Accurate Multiple Sequence Alignment"; Journal of Molecular Biology, vol. 302; pp. 205-217 (2000).
Pulkkinen and Miller; "A *Salmonella typhimurium* Virulence Protein Is Similar to a Yersinia enterocolitica Invasion Protein and a Bacteriophage Lambda Outer Membrane Protein"; J Bacteriol, vol. 173, Issue No. 1; pp. 86-93 (1991).
Sambrook, et al.; "Molecular cloning a laboratory manual: 3rd Edition"; Cold Spring Laboratory Press, 30 pages (2001).
Shetron-Rama, L. et al.; "Intracellular Induction of Listeria monocytogenes actA Expression"; Infect Immun, vol. 70, Issue No. 3; pp. 1087-1096; DOI:10.1128/ISI.70.3.1087-1096.2002 (2002).

* cited by examiner

COELENTERAZINE (CTZ)

FURIMAZINE (FRZ)

DIPHENYLTERAZINE (DTZ)

3a, pyCTZ 3c, 8pyDTZ 3d, 6pyDTZ

| | | | |
|---|---|---|---|
| 1 | LumiLuc (-2-169) | XX | mScarlet-I (1-232) |
| 2 | mScarlet-I (1-232) | XX | LumiLuc (1-169) |
| 3 | mScarlet-I (1-225) | X | LumiLuc (2-169) |

pyOMeCTZ, 416 NM pyDTZ, 520 NM

AkaLumine, 650 NM

OpyLuc: L20Q, S21A, Q22K, V23A, V29L, S30T, G69C, G73A, N87D, R114Q, V121K

ATP-INDEPENDENT BIOLUMINESCENT REPORTER VARIANTS TO IMPROVE IN VIVO IMAGING

CROSS REFERENCE TO RELATED APPLICATIONS

This application claims benefit of U.S. Provisional Application Ser. No. 62/811,129, filed Feb. 27, 2019, the disclosure of which is incorporated herein by reference in its entirety.

GRANT STATEMENT

This invention was made with government support under Grant Nos. R01GM118675 and R01GM129291 awarded by the National Institute of General Medical Sciences of the National Institutes of Health, and Grant No. CHE1750660 awarded by the National Science Foundation. The government has certain rights in the invention.

TECHNICAL FIELD

The presently disclosed subject matter relates to ATP-independent bioluminescent reporter variants to improve in vivo imaging. In some embodiments, methods, kits, and compositions for enhanced bioluminescent imaging are provided.

BACKGROUND

In the past few decades, fluorescence imaging has evolved quickly and become a dominant visualization method for live-cell studies.[1] However, fluorescence imaging has several limitations, such as photobleaching, phototoxicity, and poor tissue penetration, largely due to the need for light excitation. Unlike fluorescence, bioluminescence produces photons via enzyme-catalyzed biochemical reactions in which luciferases oxidize their corresponding small-molecule substrates (also referred to as luciferins) to generate excited-state emitters. As a result, bioluminescence signals glow essentially on dark background, leading to excellent signal-to-background ratios. Moreover, even though the spatiotemporal resolution of bioluminescence imaging (BLI) is usually worse than that of fluorescence imaging, the emitted photons can escape through several centimeters of tissue.[2] BLI is thus especially suited for diverse, noninvasive in vivo imaging applications.[3-5]

*Photinus pyralis* firefly luciferase (FLuc) and D-luciferin ($\lambda_{max}$: 563 nm) constitute the most widely used luciferase-luciferin pair for in vivo BLI. Recently, research has been performed to develop FLuc and D-luciferin derivatives for brighter and more red-shifted emission. In particular, an Akaluc-AkaLumine luciferase-luciferin pair with near-infrared (NIR) emission ($\lambda_{max}$: 650 nm) was reported for highly sensitive deep-tissue in vivo BLI.[6] Despite the progress, AkaLumine has been shown to induce cytotoxicity.[7-9] Moreover, FLuc, Akaluc, and other insect luciferases consume ATP for photon production; the bioluminescence reaction between FLuc and D-luciferin reduced the intracellular ATP-to-ADP ratio of live mammalian cells from greater than 40:1 to about 20:1,[8] suggesting metabolic disruption by all ATP-dependent luciferases. Because ATP is required for the activation of the luciferin substrates, this metabolic disruption issue cannot be addressed by simply improving insect luciferases and the corresponding substrates.

In contrast to insect luciferases, a large family of marine luciferases and photoproteins, such as Renilla luciferase (RLuc), Gaussia luciferase (GLuc), Oplophorus luciferase (OLuc), and aequorin, are ATP-independent and use coelenterazine (CTZ, FIG. 1) as their native substrate for bioluminescence production.[10] The 19 kDa catalytic domain of OLuc[11] was recently engineered into NanoLuc, which has a fast enzyme turnover and produces intense blue bioluminescence ($\lambda_{max}$: 456 nm) in the presence of a synthetic CTZ analog, furimazine (FRZ, FIG. 1).[12] To expand the color palette, NanoLuc was further engineered into teLuc, which emits red-shifted photons ($\lambda_{max}$: 502 nm) when paired with a synthetic substrate diphenylterazine (DTZ, FIG. 1).[7] Since biological tissues significantly absorb and scatter short-wavelength photons,[13] NanoLuc and teLuc have been fused to fluorescent proteins, resulting in Antares, Antares2, and enhanced Nano-Lanterns for further red-shifted emission via bioluminescence resonance energy transfer (BRET).[7, 14, 15] The water solubility of CTZ, FRZ, and DTZ is adequate for protein- and cell-based assays, because their solubility is already higher than typical substrate concentrations in these in vitro assays. However, in vivo applications of existing ATP-independent bioluminescent reporters are greatly hindered by the low solubility of CTZ, FRZ, and DTZ. Small animals, such as mice, can only tolerate a small injection volume. To enhance bioluminescence brightness by delivering more luciferin substrate, hydroxypropyl-β-cyclodextrin, polyethylene glycols (PEGs), or other organic cosolvents are typically used to formulate CTZ, FRZ, or DTZ for in vivo administration.[7, 14, 16, 17] These formulation ingredients are not biologically inert and can cause irritation or biotoxicity. It is also practically difficult to intravenously (i.v.) inject these highly viscous solutions into small animals. Furthermore, it is still of great interest to further red-shift marine luciferases for enhanced tissue penetration.

Taken together, there is a long-felt need for new and improved ATP-independent bioluminescent reporters, which have improved biochemical and photophysical properties and broad applicability. Such needs are address by the present disclosure.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, provided herein are bioluminescent proteins, comprising a substituted luciferase polypeptide comprising an amino acid sequence having at least 90% homology to SEQ ID NO: 2 with amino acid substitutions at one or more of positions corresponding to positions 6, 20, 21, 29, 30, 69, 73, 87, 92, 114, 121, and 138 of SEQ ID NO: 2. In some embodiments, the bioluminescent proteins comprise amino acid substitutions at positions corresponding to positions 20, 21, 29, and 30, and further comprise one or more amino acid substitutions at one or more of positions corresponding to positions 6, 69, 73, 87, 92, 114, 121, and 138 of SEQ ID NO: 2. In some embodiments, the bioluminescent protein comprise an amino acid sequence having at least 95% homology to SEQ ID NO: 2 with amino acid substitutions at least eight positions selected from positions corresponding to positions 6, 20, 21, 29, 30, 69, 73, 87, 92, 114, 121, and 138 of SEQ ID NO: 2. In some embodiments, a luciferase polypeptide is substituted at positions corresponding to positions 6, 20, 21, 29, 30, 69, 73, 87, 92, 114, 121, and 138 of SEQ ID NO: 2. In some embodiments, the luciferase polypeptide can comprise SEQ ID NO: 3.

In some embodiments, bioluminescent proteins disclosed herein can comprise a fluorescent protein connected to the substituted luciferase polypeptide. The fluorescent protein can be connected to the substituted luciferase polypeptide so as to allow bioluminescence resonant energy transfer (BRET) between the substituted luciferase polypeptide and the fluorescent protein. A substituted luciferase polypeptide can comprise an amino acid sequence having at least 90% homology to SEQ ID NO: 5, or can comprise the amino acid sequence of SEQ ID NO: 5.

Provided herein are bioluminescent proteins comprising an amino acid sequence having at least 90% homology to SEQ ID NO: 6, SEQ ID NO: 8, SEQ ID NO: 10, or SEQ ID NO: 12. Nucleic acids encoding these bioluminescent proteins are also provided. Vectors encoding the nucleic acids are provided, as are expression vectors encoding the nucleic acids and functionally connected to a promoter. In some aspects, cell lines containing the expression vector and expressing the bioluminescent protein are provided. Additionally, non-human cells transfected with the expression vector and expressing the bioluminescent protein are provided.

Combinations comprising a bioluminescent protein and a luciferin are provided. The luciferin can comprise a luciferin selected from pyCTZ, 6pyDTZ, and 8pyDTZ. Methods of producing luminescence, comprising reacting a luciferin with a disclosed bioluminescent protein, are also provided. In such methods the bioluminescent protein can further comprise a fluorescent protein connected to the substituted luciferase polypeptide so as to allow BRET activity between the substituted luciferase polypeptide and the fluorescent protein.

Provided herein are luciferin compounds comprising an analog of pyridyl coelenterazine (CTZ), pyridyl furimazine (FRZ) and/or a pyridyl diphenylterazine (DTZ). The compounds comprise a water solubility increased by at least about 4-fold as compared to CTZ and/or DTZ, optionally by at least about 10-fold as compared to CTZ and/or DTZ. The compounds can in some aspects comprise a water solubility ranging from about 1,000 μM to about 1,800 μM. The luciferin compounds can comprise a bioluminescence ranging from about 450 $\lambda_{max}$ (nm) to about 550 $\lambda_{max}$ (nm), and can be compatible with any luciferase, optionally any ATP-independent luciferase, including for example luciferases comprising a polypeptide comprising SEQ ID NO: 3, SEQ ID NO:5, SEQ ID NO:6, SEQ ID NO:8, SEQ ID NO:10, or SEQ ID NO: 12.

Methods of making a luciferin compound are provided herein, and can include making one or more pyridyl isomer substitutions at a C-2, C-6 and C-8 position of an imidazopyrazinone core.

In some embodiments, provided herein are bioluminescent reporter systems, such systems comprising at least two bioluminescent proteins selected from RLuc8, OpyLuc and Akaluc, and at least two luciferin compounds select from pyOMeCTZ, pyDTZ and AkaLumine. In some aspects, the system comprises bioluminescent proteins consisting of RLuc8, OpyLuc and Akaluc, and luciferin compounds consisting of pyOMeCTZ, pyDTZ and AkaLumine. In some aspects, the bioluminescent proteins and luciferin compounds are provided in pairs as follows: RLuc8 with pyOMeCTZ, OpyLuc with pyDTZ, and Akaluc with AkaLumine. The pairs of bioluminescent proteins and luciferins produce distinct colors of emission across the visible spectrum. In some aspects, RLuc8 paired with pyOMeCTZ yields a bioluminescence of about 380-470 (nm), OpyLuc paired with pyDTZ yields a bioluminescence of about 480-600 (nm), and Akaluc paired with AkaLumine yields a bioluminescence of about 600-750 (nm). In such reporter systems, RLuc8 can comprise a polypeptide sequence comprising SEQ ID NO: 14, OpyLuc can comprise a polypeptide sequence comprising SEQ ID NO: 6, and Akaluc can comprise a polypeptide sequence comprising SEQ ID NO: 16. Nucleic acids, vectors, expression vectors and cell lines encoding and/or expressing the reporter systems are also provided.

In some embodiments, provided herein are methods of monitoring bioluminescence in a subject, the methods comprising providing a subject, establishing in the subject a luciferase expressing cell, wherein the luciferase is selected from the group consisting of LumiLuc, teLuc, RLuc8 and OpyLuc, administering to the subject a luciferin selected from the group consisting of pyCTZ, pyOHCTZ, pyOMeCTZ, pyOEtCTZ, pyiPrCTZ, 2pyDTZ, 6pyDTZ, 6opyDTZ and 8pyDTZ, and measuring bioluminescence in the subject. In some aspects, the subject comprises a tumor or a cancer cell. In some aspects, the luciferase expressing cell comprises a tumor or a cancer cell. In some embodiments, the subject comprises an in vivo tumor or cancer model. In some embodiments, the subject is a non-human animal. In some embodiments, the bioluminescence is measured in a tumor or cancer cell in the subject.

Provided herein are cells containing an expression vector for expressing a bioluminescent protein, wherein the bioluminescent protein is selected from the group consisting of LumiLuc, teLuc, RLuc8 and OpyLuc, wherein the expression vector comprises a responsive promoter element, wherein the responsive promoter element is responsive to a stimuli of a cell signaling pathway. Such cells can be cultured in vitro.

Provided herein are cell signaling assay systems, the systems comprising cells containing an expression vector for expressing a bioluminescent protein, and a luciferin selected from the group consisting of pyCTZ, pyOHCTZ, pyOMeCTZ, pyOEtCTZ, pyiPrCTZ, 2pyDTZ, 6pyDTZ, 6opyDTZ and 8pyDTZ, wherein the assay is configured to indicate activation of a cell signaling pathway by bioluminescence.

Methods for monitoring a cell signaling pathway are provided, where the methods comprise culturing cells containing an expression vector for expressing a bioluminescent protein, exposing the cell to a luciferin selected from the group consisting of pyCTZ, pyOHCTZ, pyOMeCTZ, pyOEtCTZ, pyiPrCTZ, 2pyDTZ, 6pyDTZ, 6opyDTZ and 8pyDTZ, exposing the cell to a compound of interest, and measuring bioluminescence in the cell, wherein an increase in bioluminescence in the cell is indicative of an activation of the cell signaling pathway in the cell. The compound of interest can comprise a drug candidate compound.

Provided herein are stable cell lines integrated with a series of nucleic acids disclosed herein and expressing the bioluminescent proteins.

Accordingly, it is an object of the presently disclosed subject matter to provide engineered luciferases, modified luciferase substrates and related methods. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Figures, and Examples.

BRIEF DESCRIPTION OF THE FIGURES

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

Like numbers refer to like elements throughout. In the figures, the thickness of certain lines, layers, components, elements or features can be exaggerated for clarity. Where used, broken lines illustrate optional features or operations unless specified otherwise. For a more complete understanding of the presently disclosed subject matter, reference is now made to the below drawings.

FIG. 4A is a schematic of a procedure to derive LumiLuc from teLuc. FIG. 4B is an illustration of the putative substrate-binding site and LumiLuc mutations from teLuc. CTZ is shown as spheres and mutated residues are presented in sticks. FIG. 4C shows the bioluminescence of pyCTZ, 6pyDTZ, or 8pyDTZ in the presence of either teLuc or LumiLuc. FIG. 4D shows normalized bioluminescence emission spectra of pyCTZ, 6pyDTZ, and 8pyDTZ in the presence of LumiLuc.

FIG. 6A shows the determination of apparent Michaelis constants ($K_M$) by substrate titrations (teLuc-DTZ: 9.9±0.9 μM; NanoLuc-FRZ: 9.1±0.6 μM; LumiLuc-8pyDTZ: 4.6±0.6 μM; LumiLuc-pyCTZ: 13.1±0.8 μM; LumiLuc-6pyDTZ: 11.0±1.2 μM). Final concentrations of all enzymes were 20 pM. Substrate concentrations varied from 0.78 to 50 μM, and peak bioluminescence intensities at individual substrate concentrations were used to fit the Michaelis-Menten equation. FIG. 6B shows the total bioluminescence over the first 10 min post addition of corresponding luciferins. Final concentrations for luciferins were 10 μM and final concentrations for luciferases were 50 pM. Data are normalized to the intensity of Akaluc-AkaLumine and shown as mean and s.d. from three independent measurements. Under this condition, LumiLuc-8pyDTZ produced about 1200-fold higher photon flux than Akaluc-AkaLumine. Assays in panels a and b were all performed in PBS. FIG. 6C shows the bioluminescence kinetic of LumiLuc-8pyDTZ in PBS or in a formulated assay buffer containing 1 mM CDTA, 0.5% Tergitol NP-40, 0.05% Antifoam 204, 150 mM KCl, 100 mM MES, pH 6.0, 1 mM DTT, and 35 mM thiourea.

(FIG. 9A) Bioluminescence intensities integrated over the first 10 mins post injection of substrates. The y-axis is shown in a logarithmic scale. Under this condition, LumiLuc-8pyDTZ produced about 190-fold higher photon flux than Akaluc-AkaLumine. (FIG. 9B) Decay kinetics. Assays were performed with 20 μM substrates and 500 HeLa cells. Data are presented as mean and s.d. from three independent measurements.

(FIG. 10A) BLI (n=4) on day 1, 3, 5, and day 7. 104 luciferase-expressing HeLa cells were injected to the left and right dorsolateral trapezius regions and 105 cells were injected to the left and right dorsolateral thoracolumbar regions of NU/J mice. For i.v. administration of substrates, AkaLumine-HCl (3 μmol/mouse) and 8pyDTZ (0.2 μmol/mouse) were dissolved in normal saline, and DTZ (0.3 μmol/mouse) was formulated with a mixture of organic cosolvents. (FIG. 10B) Comparison of luciferase-luciferin pairs at tumor sites inoculated with 104 cells. (*$p<0.05$ for LumiLuc-8pyDTZ and teLuc-DTZ, and for LumiLuc-8pyDTZ and Akaluc-AkaLumine; **$p<0.05$ for LumiLuc-8pyDTZ and Antares2-DTZ).

(FIG. 11A) HeLa cells stably expressing indicated luciferase were injected at four sites of each female NU/J mouse. $10^4$ cells were injected to the left and right dorsolateral trapezius regions and $10^5$ cells were injected to the left and right dorsolateral thoracolumbar regions. BLI were obtained on days 1, 3, 5, 7, 14, and 28 (n=4). Pseudocolored images are presented on a scale of $5\times10^5$ to $5\times10^7$ p/sec/cm$^2$/sr. Images are identical to FIG. 4, except for that data on days 14 and 28 are presented here and that a different scale is used for pseudocoloring. (FIG. 11B) Comparison of luciferase-luciferin pairs at tumor sites inoculated with $10^5$ cells (*p<0.05 for LumiLuc-8pyDTZ and Akaluc-AkaLumine; p<0.05 for LumiLuc-8pyDTZ and teLuc-DTZ; *p<0.05 for LumiLuc-8pyDTZ and teLuc-8pyDTZ). (FIG. 11C) Bioluminescence decay kinetics for i.v.-injected luciferins (1.5 μmol for AkaLumine, 0.2 μmol for 8pyDTZ, and 0.3 μmol for DTZ) in a xenograft NU/J mouse model. Measurements were done 5 days after tumor implantation. Quantifications were made at sites initially inoculated with 105 cells. Data are presented as mean and s.d. from four replicates.

(FIG. 12A) Libraries screened for high BRET. Each "X" represents an amino acid residue randomized with the NNK codon, in which N=A/C/G/T and K=G/T. (FIG. 12B) Bioluminescence spectra of constructs selected from each library in the presence of 8pyDTZ. (FIG. 12C) Normalized fluorescence excitation and emission spectra of mScarlet-I and bioluminescence emission of LumiLuc-8pyDTZ, showing excellent spectral overlap for BRET. (FIG. 12D) Comparison of LumiLuc and LumiScarlet (100 pM purified enzymes) for bioluminescence integrated over the first 10 min post injection of 20 μM 8pyDTZ. (FIG. 12E) Schematic diagram of teScarlet, a genetic fusion of mScarlet-I and teLuc. (FIG. 12F) Bioluminescence emission of teScarlet in the presence of DTZ, showing significant emission longer than 600 nm.

(FIG. 13A) Schematic diagram of LumiScarlet, a genetic fusion of mScarlet-I and LumiLuc. (FIG. 13B) Bioluminescence emission of LumiScarlet in the presence of pyCTZ, 6pyDTZ, or 8pyDTZ, showing significant emission longer than 600 nm. (FIG. 13C) Comparison of LumiLuc-8pyDTZ, LumiScarlet-8pyDTZ, and Akaluc-AkaLumine in NU/J mice (n=4) at 4 h post i.v. injection of 106 luciferase-expressing HeLa cells. (FIG. 13D) Quantitative analysis of bioluminescence from the regions around the lungs in panel c (n.s.: not significant).

(FIG. 15A) The schematic representation of directed evolution to derive OpyLuc. (FIG. 15B) Illustration of the putative substrate-binding site and OpyLuc mutations. CTZ is shown as spheres and mutated residues near the binding site are highlighted in yellow. (FIG. 15C) Normalized bioluminescence activity ratio of pyCTZ/pyOMeCTZ in the presence of either teLuc or OpyLuc.

(FIG. 17A) Schematic representation of spectral-resolved and orthogonal luciferase-luciferin pairs.

FIGS. 18A and 8B show the determination of apparent Michaelis constants ($K_M$) by substrate titrations. (FIG. 18A) OpyLuc-pyDTZ: 9.8±1.7 μM.

(FIG. 19A) Images were acquired without a filter or with either a 360-500 nm, 495-580 nm, or 600-700 nm bandpass filter. (FIG. 19B) Quantitative values for each tested luciferase-luciferin pair. Final concentrations were 10 nM for RLuc8 and OpyLuc; 100 nM for Akaluc; 30 μM corresponding luciferin. (FIG. 19C) Live HEK293T cells were transfected with either RLuc8, Akaluc, or OpyLuc. 5000 cells per well for RLuc8 and OpyLuc; 30,000 cells per well for Akaluc. Images were acquired without a filter after addition of 1: 10 μM pyDTZ, 2: 100 μM AkaLumine, or 3:25 μM pyOMeCTZ. (FIG. 19D) Quantitative analysis of BL signals gained from (FIG. 19C).

(FIG. 21A) Schematic of triple luciferase assay in live HEK293T after co-transfection of SRE-RLuc8, ARE-OpyLuc, and NFκB-Akaluc plasmids. The emission spectra were acquired from intact cells after adding Optimal Mix solution. The cells were (FIG. 21B) non-treated, induced by (FIG. 21C) 20% FBS, (FIG. 21D) 50 μM tBHQ, (FIG. 21E) 10 ng/mL TNFα, (FIG. 21F) 20% FBS+10 ng/mL TNFα, (FIG. 21G) 20% FBS+50 μM tBHQ, (FIG. 21H) 50 μM tBHQ+10 ng/mL TNFα, (FIG. 21I) 20% FBS+50 μM tBHQ 10 ng/mL+TNFα for 16 h post PEI transfection.

(FIG. 22A) Schematic diagrams of LumiCameleon1 and LumiCameleon2. (FIG. 22B) Bioluminescence emission of LumiCameleon1 in the presence of pyCTZ, showing large dynamic range in response to $Ca^{2+}$. (FIG. 22C) Bioluminescence emission of LumiCameleon2 in the presence of DTZ.

DETAILED DESCRIPTION

Figure 1:
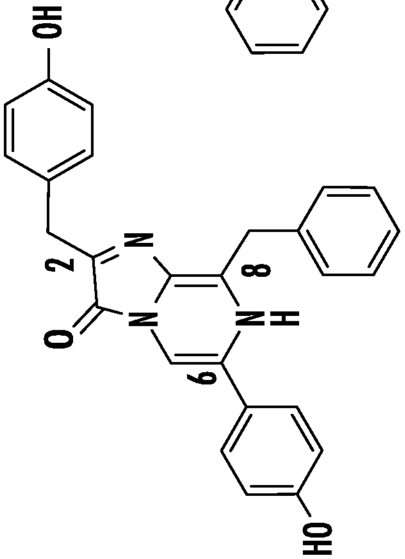
FIG. 1 includes schematic illustration of the chemical structures of coelenterazine (CTZ), furimazine (FRZ), diphenylterazine (DTZ), pyCTZ (3a in Table 2), 8pyDTZ (3c in Table 2) and 6pyDTZ (3d in Table 2).
Figure 1:
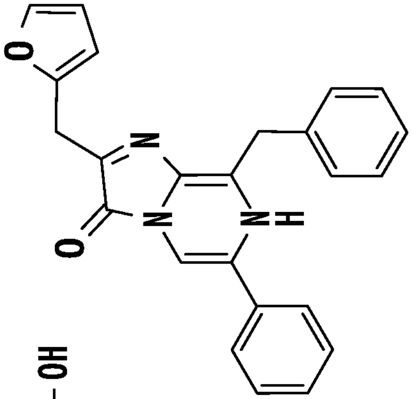
Figure 1:
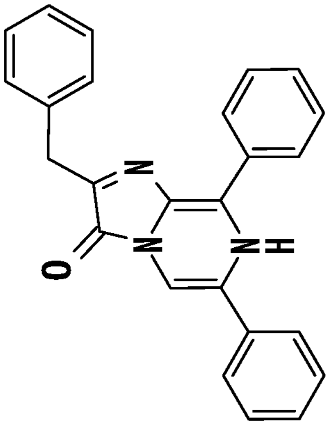
Figure 1:
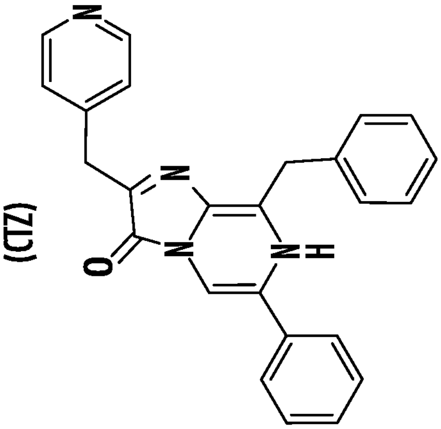
Figure 1:
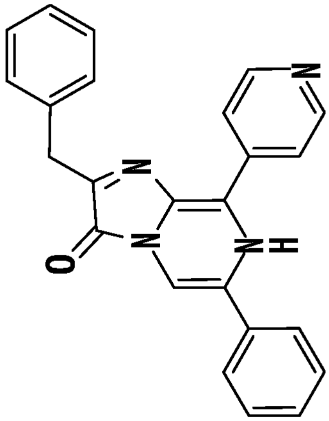
Figure 1:
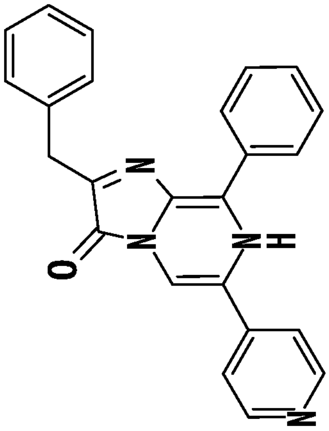

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein;

rather, these embodiments are provided so that this disclosure will satisfy applicable legal requirements.

I. General Considerations

Provided herein are chemically modified luciferase substrates, namely coelenterazine (CTZ) and diphenylterazine (DTZ), for spectrally shifted emission and enhanced water solubility. Concurrently, teLuc was engineered into a LumiLuc luciferase, which is highly active toward the new modified substrates for intense blue, teal, and yellow emission. Moreover, provided herein is a new reporter, LumiScarlet, with significant emission longer than 600 nm. The disclosed multipronged approach yielded a new family of ATP-independent bioluminescent reporters, which have improved biochemical and photophysical properties and are expected to have broad applications.

To elaborate, a series of pyridyl CTZ and DTZ analogs, or luciferin compounds, with diverse emission profiles were prepared. The water solubility of these synthetic analogs generally increased by about 10-fold from their ancestors. Surprisingly, these substrate analogs can not only be paired with the new luciferases engineered herein, but also existing ATP-independent reporters, such as RLuc and aequorin.

Such luciferin compounds, as described further herein, can include the following structure:

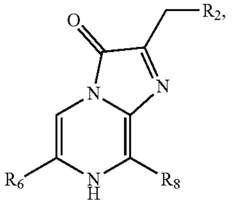

wherein R6 is selected from

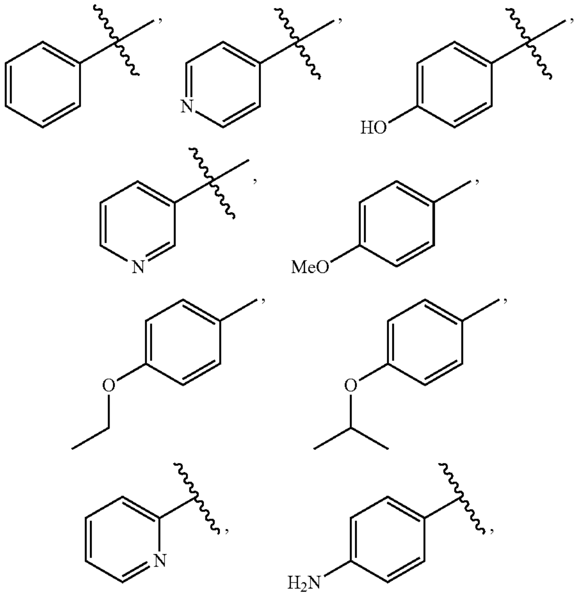

-continued

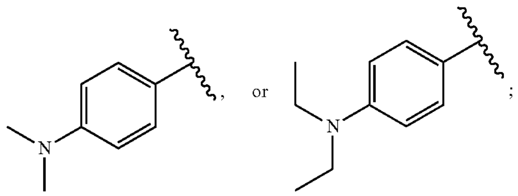

wherein R8 is selected from

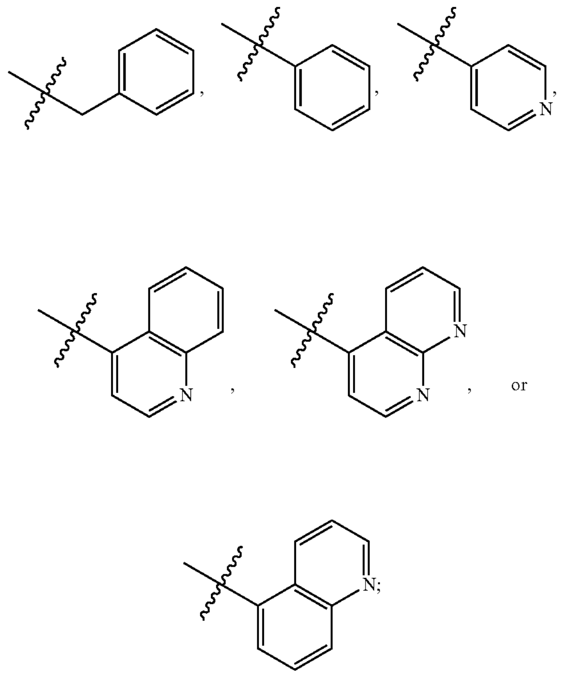

and wherein R2 is selected from

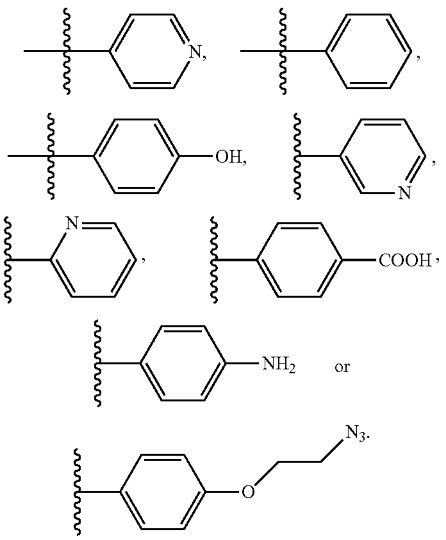

More particularly, the luciferin compounds include:

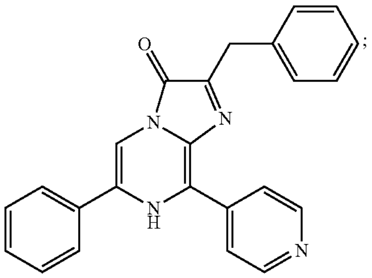

8pyDTZ

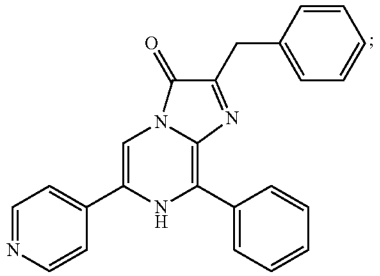

6pyDTZ

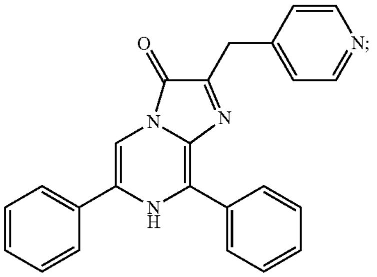

2pyDTZ

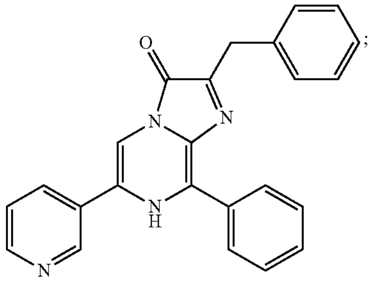

6opyDTZ

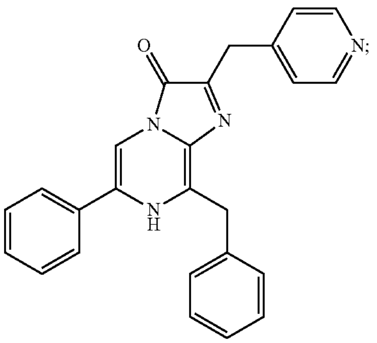

pyCTZ

-continued

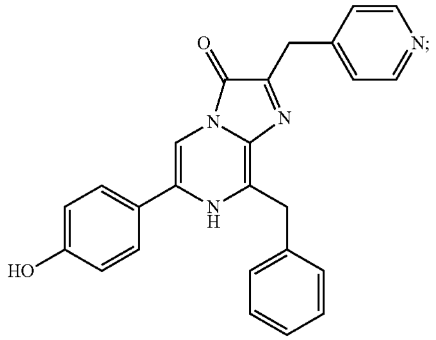

pyOHCTZ

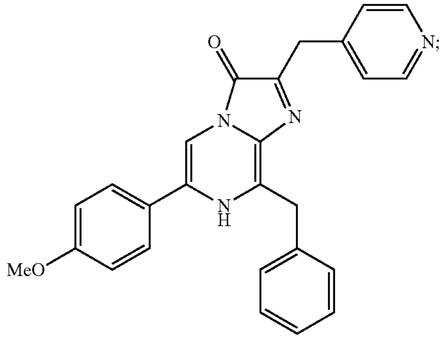

pyOMeCTZ

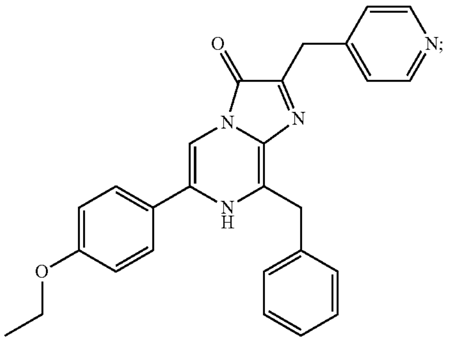

and pyOEtCTZ

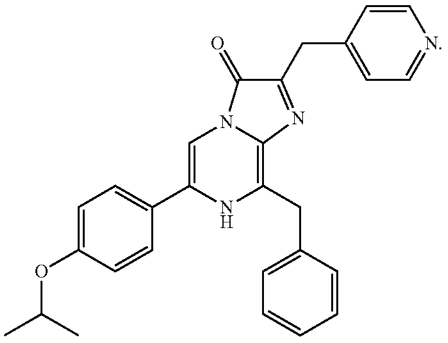

pyiPrCTZ

Methods of making luciferin compounds are provided herein, and comprise making one or more pyridyl isomer substitutions at a C-2, C-6 and C-8 position of an imidazopyrazinone core according to the following chemical synthetic route:

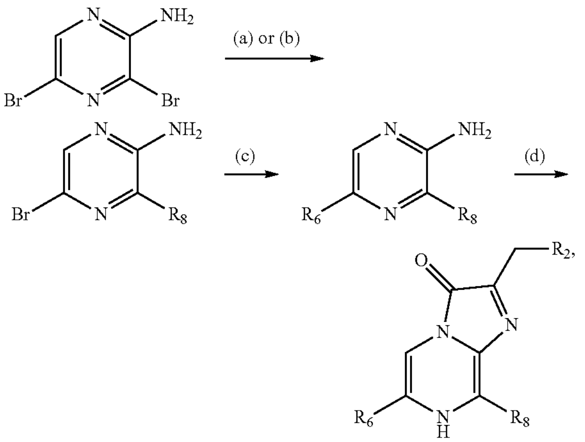

wherein step (a) comprises Suzuki coupling, comprising $Pd(PPh_3)_4$, $Na_2CO_3$, $R_8$—$B(OH)_2$, and/or EtOH; step (b) comprises Negishi coupling, comprising $PhCH_2MgCl$, $ZnCl_2$, $(PPh_3)_2PdCl_2$, and/or THF; step (c) comprises Suzuki coupling, comprising XPhos-Pd-G2, $Na_2CO_3$, $R_6$—$B(OH)_2$, and/or EtOH; and step (d) comprises acid-catalyzed ring closing, comprising corresponding α-ketoacetal, HCl, and/or dioxane.

Disclosed herein are luciferin compounds consisting of pyOMeCTZ, pyDTZ and AkaLumine, which comprise the following chemical structures:

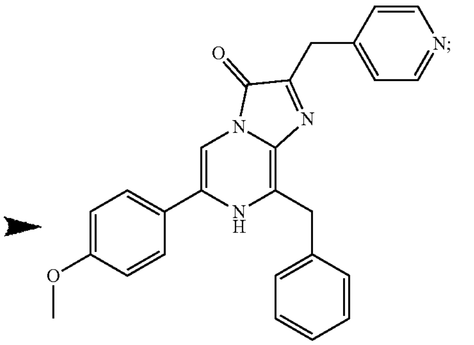

pyOMeCTZ

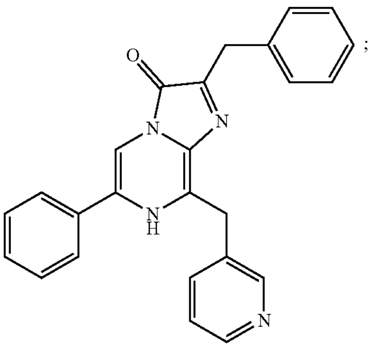

; and pyDTZ

-continued

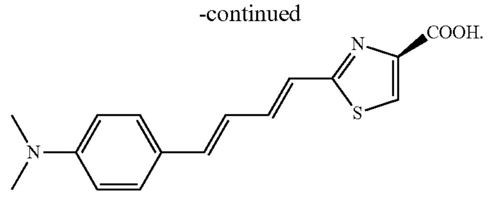

AkaLumine

Moreover, the LumiLuc luciferase provided herein can in some embodiments comprise a substituted teLuc luciferase, including up to twelve substitutions, as discussed further hereinbelow. In some aspects, a fluorescent protein can be connected to the substituted luciferase polypeptides so as to allow bioluminescence resonant energy transfer (BRET) between the substituted luciferase polypeptide and the fluorescent protein.

Engineered luciferases provided herein, also referred to as bioluminescent proteins, include LumiLuc (SEQ ID NO. 3), LumiScarlet (SEQ ID NOs. 4 and 5), OpyLuc (SEQ ID NO. 6), teScarlet (SEQ ID NOs. 7 and 8), LumiCameleon1 (SEQ ID NOs. 9 and 10), and LumiCameleon2 (SEQ ID NOs. 11 and 12). Additional luciferases are also provided as follows: NanoLuc (SEQ ID NO. 1), teLuc (SEQ ID NO. 2), RLuc8 (SEQ ID NOs. 13 and 14), Akaluc (SEQ ID NOs. 15 and 16), NanoKAZ (SEQ ID NO. 17), and yeLuc (SEQ ID NO. 18).

In addition, provided herein are engineered mutually orthogonal luciferase-luciferin pairs for multiplexed cell-based bioluminescence (BL) assays. Disclosed triple-color BL systems feature the selectivity of synthetic substrates and production of well separated emission spectra from about 400 nm to about 650 nm. The disclosed spectral-resolved triple-color BL systems provide flexible and convenient approaches to monitor multiple biological events in either qualitative or quantitative manners.

New bioluminescent $Ca^{2+}$ biosensors were also developed based on the modified luciferase compounds disclosed herein. These bioluminescent $Ca^{2+}$ biosensors showed large bioluminescence increase in response to $Ca^{2+}$, making them well suited for in vivo and in vitro applications.

The disclosed luciferase-luciferin pairs can also be used for in vivo monitoring of tumor models. For example, bioluminescence can be monitored in a tumor model by administering to that model, or otherwise establishing in the model, a luciferase expressing cell (e.g. a tumor cell expressing LumiLuc, teLuc, RLuc8 and OpyLuc), and administering to the model a luciferin (e.g. pyCTZ, pyOHCTZ, pyOMeCTZ, pyOEtCTZ, pyiPrCTZ, 2pyDTZ, 6pyDTZ, 6opyDTZ or 8pyDTZ). Using these luciferase-luciferin pairs as reporter systems the bioluminescence can be used as a tool to monitor the tumor.

The present disclosure provides for the use of the new luciferase-luciferin pairs for assays of cell signaling pathways. By way of example and not limitation, the disclosed luciferase-luciferin pairs can allow for the monitoring of particular cell signaling pathways, which can be implemented to for candidate compound and drug screening applications.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. Thus, unless defined otherwise, all technical and scientific terms and any acronyms used herein have the same meanings as commonly understood by one of ordinary skill in the art in the field of the presently disclosed subject matter. Although any compositions, methods, kits, and means for communicating information similar or equivalent to those described herein can be used to practice the presently disclosed subject matter, particular compositions, methods, kits, and means for communicating information are described herein. It is understood that the particular compositions, methods, kits, and means for communicating information described herein are exemplary only and the presently disclosed subject matter is not intended to be limited to just those embodiments.

Following long-standing patent law convention, the terms "a", "an", and "the" refer to "one or more" when used in this application, including the claims. Thus, in some embodiments the phrase "a peptide" refers to one or more peptides.

The term "about", as used herein to refer to a measurable value such as an amount of weight, time, dose, etc., is meant to encompass in some embodiments variations of ±20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed methods.

As used herein, the term "and/or" when used in the context of a list of entities, refers to the entities being present singly or in any and every possible combination and subcombination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

As used herein, the term "subject" refers to an individual (e.g., human, animal, or other organism) to be treated by the methods or compositions of the present invention. Subjects include, but are not limited to, mammals (e.g., murines, simians, equines, bovines, porcines, canines, felines, and the like), and includes humans. In the context of the invention, the term "subject" generally refers to an individual who will receive or who has received treatment for a condition characterized by the presence of bacteria (e.g., *Bacillus anthracis* (e.g., in any stage of its growth cycle), or in anticipation of possible exposure to bacteria. As used herein, the terms "subject" and "patient" are used interchangeably, unless otherwise noted.

As used herein, the terms "effective amount" and "therapeutically effective amount" are used interchangeably and refer to the amount that provides a therapeutic effect, e.g., an amount of a composition that is effective to treat or prevent pathological conditions, including signs and/or symptoms of disease, associated with a pathogenic organism infection (e.g., spore germination, bacterial growth, toxin production, etc.) in a subject.

As used herein, the term "adjuvant" as used herein refers to an agent which enhances the pharmaceutical effect of another agent.

The expression "amino acid" as used herein is meant to include both natural and synthetic amino acids, and both D- and L-amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage can be present or absent in the peptides of the invention.

The term "amino acid" is used interchangeably with "amino acid residue", and can refer to a free amino acid and to an amino acid residue of a peptide. It will be apparent from the context in which the term is used whether it refers to a free amino acid or a residue of a peptide.

The term "antibody", as used herein, refers to an immunoglobulin molecule which is able to specifically bind to a specific epitope on an antigen. Antibodies can be derived from natural sources or from recombinant sources and can be intact immunoglobulins or immunoreactive portions of intact immunoglobulins (for example, a fragment or derivative of an antibody that includes an antigen-binding site or a paratope). Antibodies are typically tetramers of immunoglobulin molecules. The antibodies in the present invention can exist in a variety of forms including, for example, polyclonal antibodies, monoclonal antibodies, Fv, Fab and $F(ab)_2$, as well as single chain antibodies and humanized antibodies (see e.g., Harlow & Lane (1999) *Using Antibodies: A Laboratory Manual*, Cold Spring Harbor Laboratory Press, Cold Spring Harbor, New York, United States of America; Harlow & Lane (1988) *Antibodies: A Laboratory Manual*, Cold Spring Harbor Laboratory Press, Cold Spring Harbor, New York, United States of America; Houston et al. (1988) Proc Natl Acad Sci USA 85:5879-5883; Bird et al. (1988) Science 242:423-426; each of which is incorporated herein by reference in its entirety).

The term "synthetic antibody" as used herein refers to an antibody which is generated using recombinant DNA technology, such as, for example, an antibody expressed by a bacteriophage or a host cell. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (see e.g., U.S. Pat. No. 5,034,506 to Summerton and Weller; Nielsen et al. (1991) Science 254:1497-1500). The term "antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence can be complementary to regulatory sequences specified on the coding strand of a DNA molecule encoding a protein, which regulatory sequences control expression of the coding sequences.

As used herein, the term "biologically active fragments" or "bioactive fragment" of a polypeptide encompasses natural or synthetic portions of the full-length protein that are capable of specific binding to their natural ligand or of performing the function of the protein.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T", is complementary to the sequence "T-C-A."

The term "complex", as used herein in reference to proteins, refers to binding or interaction of two or more proteins. Complex formation or interaction can include such things as binding, changes in tertiary structure, and modification of one protein by another, such as phosphorylation.

A "compound", as used herein, refers to any type of substance or agent that is commonly considered a chemical, drug, or a candidate for use as a drug, as well as combinations and mixtures of the above. The term compound further encompasses molecules such as peptides and nucleic acids.

As used herein, a "derivative" of a compound refers to a chemical compound that can be produced from another compound of similar structure in one or more steps, as in replacement of H by an alkyl, acyl, or amino group. Similarly, a "derivative" of a peptide (or of a polypeptide) is a compound that can be produced from or has a biological activity similar to a peptide (or a polypeptide) but that differs in the primary amino acid sequence of the peptide (or the polypeptide) to some degree. By way of example and not limitation, a derivative of a subject peptide of the presently disclosed subject matter is a peptide that has a similar although not identical primary amino acid sequence as the subject peptide (for example, has one or more amino acid substitutions) and/or that has one or more other modifications (e.g., N-terminal, C-terminal, and/or internal modifications) as compared to the subject peptide. Thus, the term "derivative" compasses the term "modified peptide" and vice versa, in the context of peptides. In some embodiments, a derivative of a peptide is a C-terminal amidated peptide.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid of the amino acid sequence, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

The terms "formula" and "structure" are used interchangeably herein.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J Mol Biol 215:403-410) are available for determining sequence identity.

In some embodiments, "identity" can be expressed as a "percent identity". As used herein, the phrase "percent identity" in the context of two nucleic acid or polypeptide sequences, refers to two or more sequences or subsequences that have in some embodiments 60%, in some embodiments 70%, in some embodiments 75%, in some embodiments 80%, in some embodiments 85%, in some embodiments 90%, in some embodiments 92%, in some embodiments 94%, in some embodiments 95%, in some embodiments 96%, in some embodiments 97%, in some embodiments 98%, in some embodiments 99%, and in some embodiments 100% nucleotide or amino acid residue identity, respectively, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments, the percent identity exists over at least about 150 residues. In some embodiments, the percent identity exists over the entire length of the sequences.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm disclosed in Smith & Waterman (1981) 2 Adv Appl Math 482-489; by the homology alignment algorithm disclosed in Needleman & Wunsch (1970) 48 J Mol Biol 443-453; by the search for similarity method disclosed in Pearson & Lipman (1988) Proc Natl Acad Sci USA 85:2444-2448; by computerized implementations of these algorithms (GAP, BESTFIT, FASTA, and TFASTA in the GCG® WISCONSIN PACKAGE®, available from Accelrys, Inc., San Diego, California, United States of America), or by visual inspection. See generally, Altschul et al. (1990) 215 J Mol Biol 403-410; Ausubel et al. (2002) Short Protocols in Molecular Biology, Fifth ed. Wiley, New York, New York, United States of America; and Ausubel et al. (2003) Current Protocols in Molecular Biology, John Wylie & Sons, Inc, New York, New York, United States of America.

One example of an algorithm that is suitable for determining percent sequence identity and sequence similarity is the BLAST algorithm, which is described in Altschul et al. (1990) 215 J Mol Biol 403-410. Software for performing BLAST analysis is publicly available through the website of the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold. See generally, Altschul et al. (1990) 215 J Mol Biol 403-410. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix. See Henikoff & Henikoff (1992) 89 Proc Natl Acad Sci USA 10915-10919.

In addition to calculating percent sequence identity, the BLAST algorithm also performs a statistical analysis of the similarity between two sequences (see e.g., Karlin & Altschul (1993) 90 Proc Natl Acad Sci USA 5873-5877). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

The term "inhibit", as used herein, refers to the ability of a compound or any agent to reduce or impede a described function or pathway. For example, inhibition can be by at least 10%, by at least 25%, by at least 50%, by at least 75%, by at least 80%, by at least 85%, by at least 90%, by at least 95%, by at least 97%, by at least 99%, or more.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound invention or be shipped together with a container which contains the identified compound. Alternatively, the instructional material can be shipped separately from the container with the intention that the instructional material and the compound be used cooperatively by the recipient.

An "isolated" compound/moiety is a compound/moeity that has been removed from components naturally associated with the compound/moiety. For example, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "modulate", as used herein, refers to changing the level of an activity, function, or process. The term "modulate" encompasses both inhibiting and stimulating an activity, function, or process.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in an animal. In some embodiments, a pharmaceutically acceptable carrier is pharmaceutically acceptable for use in a human.

The term "polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides (e.g., a polypeptide of in some embodiments at least 50 amino acids, in some embodiments at least 75 amino acids, in some embodiments at least 100 amino acids, in some embodiments at least 200 amino acids, in some embodiments at least 300 amino acids, in some embodiments at least 500 amino acids, and in some embodiments more than 500 amino acids).

A peptide encompasses a sequence of 2 or more amino acids wherein the amino acids are naturally occurring or synthetic (non-naturally occurring) amino acids.

The term "linked" or like terms refers to a connection between two entities. The linkage can comprise a covalent, ionic, or hydrogen bond or other interaction that binds two compounds or substances to one another.

As used herein the term "peptidomimetic" refers to a chemical compound having a structure that is different from the general structure of an existing peptide, but that functions in a manner similar to the existing peptide, e.g., by mimicking the biological activity of that peptide. The term "modified peptide" encompasses a peptidomimetic. Peptidomimetics typically comprise naturally-occurring amino acids and/or unnatural amino acids, but can also comprise modifications to the peptide backbone. For example, a peptidomimetic can include one or more of the following modifications:

1. Peptides wherein one or more of the peptidyl —C(O)NR— linkages (bonds) have been replaced by a non-peptidyl linkage such as a —$CH_2$-carbamate linkage (—$CH_2OC(O)NR$—), a phosphonate linkage, a —$CH_2$-sulfonamide (—$CH_2$—$S(O)_2NR$—) linkage, a urea (—NHC(O)NH—) linkage, a —$CH_2$-secondary amine linkage, an azapeptide bond (CO substituted by NH), or an ester bond (e.g., depsipeptides, wherein one or more of the amide (—CONHR—) bonds are replaced by ester (COOR) bonds) or with an alkylated peptidyl linkage (—C(O)NR—) wherein R is $C_1$-$C_6$ alkyl;
2. Peptides wherein the N-terminus is derivatized to a —NRR1 group, to a —NRC(O)R group, to a —NRC(O)OR group, to a —$NRS(O)_2R$ group, to a —NHC(O)NHR group where R and R1 are hydrogen or $C_1$-$C_6$ alkyl with the proviso that R and RI are not both hydrogen;
3. Peptides wherein the C terminus is derivatized to —C(O)R2 where R2 is selected from the group consisting of $C_1$-$C_6$ alkoxy, and —NR3R4 where R3 and R4 are independently selected from the group consisting of hydrogen and $C_1$-$C_4$ alkyl;
4. Modification of a sequence of naturally-occurring amino acids with the insertion or substitution of a non-peptide moiety, e.g., a retroinverso fragment.

The term "permeability", as used herein, refers to transit of fluid, cell, or debris between or through cells and tissues.

A "sample", as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds", as used herein, is meant a compound which recognizes and binds a specific protein, but does not substantially recognize or bind other molecules in a sample, or it means binding between two or more proteins as in part of a cellular regulatory process, where said proteins do not substantially recognize or bind other proteins in a sample.

The term "standard", as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "symptom", as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

As used herein an "amino acid modification" refers in some embodiments to a substitution, addition, or deletion of an amino acid, and includes substitution with, or addition of, any of the 20 amino acids commonly found in human proteins, as well as unusual or non-naturally occurring amino acids such as but not limited to D-amino acids. Commercial sources of unusual amino acids include Sigma-Aldrich (Milwaukee, Wisconsin, United States of America), ChemPep Inc. (Miami, Florida, United States of America), and Genzyme Pharmaceuticals (Cambridge, Massachusetts, United States of America). Unusual amino acids can be purchased from commercial suppliers, synthesized de novo, or chemically modified or derivatized from naturally occurring amino acids. Amino acid modifications include linkage of an amino acid to a conjugate moiety, such as a hydrophilic polymer, acylation, alkylation, and/or other chemical derivatization of an amino acid. The term "modified peptide" encompasses any amino acid modification as described herein.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substitutions can be designed based on, for example, the model of Dayhoff et al. (in *Atlas of Protein Sequence and Structure* 1978, National Biomedical Research Foundation, Washington D.C., United States of America).

In some embodiments, an amino acid substitution is a conservative amino acid substitution. As used herein, the term "conservative amino acid substitution" is defined in some embodiments as exchanges within one of the following five groups:

I. Small aliphatic, nonpolar or slightly polar residues: Ala, Ser, Thr, Pro, Gly;

II. Polar, charged residues and their amides: Asp, Asn, Glu, Gln, His, Arg, Lys;

III. Large, aliphatic, nonpolar residues: Met Leu, Ile, Val, Cys

IV. Large, aromatic residues: Phe, Tyr, Trp

Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al. (1990) Science 247:1306-1310.

For example, the hydropathic index of amino acids may be considered (Kyte & Doolittle (1982) J Mol Biol 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle (1982) J Mol Biol 157:105-132), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, in some embodiments an amino acid with a compact side chain, such as glycine or serine, would not be replaced with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet, or reverse turn secondary structure has been determined and is known in the art (see e.g., Chou & Fasman (1974) Biochemistry 13:222-245; Chou & Fasman (1978) Ann Rev Biochem 47: 251-276; Chou & Fasman (1979) Biophys J 26:367-384).

Based on such considerations and extensive empirical study, tables of conservative amino acid substitutions have been constructed and are known in the art. By way of example and not limitation, the following substitutions can be made: arginine and lysine; glutamate and aspartate; serine and threonine; glutamine and asparagine; and valine, leucine, and isoleucine. Alternatively, Table 1 lists exemplary conservative amino acid substitutions.

TABLE 1

| Exemplary Conservative Amino Acid Substitutions | |
|---|---|
| Amino Acid | Possible Substitution(s) |
| Ala (A) | Leu, Ile, Val |
| Arg (R) | Gln, Asn, Lys |
| Asn (N) | His, Asp, Lys, Arg, Gln |
| Asp (D) | Asn, Glu |
| Cys (C) | Ala, Ser |
| Gln (Q) | Glu, Asn |
| Glu (E) | Gln, Asp |
| Gly (G) | Ala |
| His (H) | Asn, Gln, Lys, Arg |
| Ile (I) | Val, Met, Ala, Phe, Leu |
| Leu (L) | Val, Met, Ala, Phe, Ile |
| Lys (K) | Gln, Asn, Arg |
| Met (M) | Phe, Ile, Leu |
| Phe (F) | Leu, Val, Ile, Ala, Tyr |
| Pro (P) | Ala |
| Ser (S) | Thr |
| Thr (T) | Ser |
| Trp (W) | Phe, Tyr |
| Tyr (Y) | Trp, Phe, Thr, Ser |
| Val (V) | Ile, Leu, Met, Phe, Ala |

As used herein, amino acids are represented by the full name thereof, by the three letter code corresponding thereto, or by the one-letter code corresponding thereto, as indicated in the following table (Table 1A):

TABLE 1A

| Full Name | 3-Letter Code | 1-Letter Code | Functionally Equivalent Codons |
|---|---|---|---|
| Aspartic Acid | Asp | D | GAC GAU |
| Glutamic Acid | Glu | E | GAA GAG |
| Lysine | Lys | K | AAA AAG |
| Arginine | Arg | R | AGA AGG CGA CGC CGG CGU |
| Histidine | His | H | CAC CAU |
| Tyrosine | Tyr | Y | UAC UAU |
| Cysteine | Cys | C | UGC UGU |
| Asparagine | Asn | N | AAC AAU |
| Glutamine | Gln | Q | CAA CAG |
| Serine | Ser | S | ACG AGU UCA UCC UCG UCU |
| Threonine | Thr | T | ACA ACC ACG ACU |
| Glycine | Gly | G | GGA GGC GGG GGU |
| Alanine | Ala | A | GCA GCC GCG GCU |
| Valine | Val | V | GUA GUC GUG GUU |
| Leucine | Leu | L | UUA UUG CUA CUC CUG CUU |
| Isoleucine | Ile | I | AUA AUC AUU |
| Methionine | Met | M | AUG |

TABLE 1A-continued

| Full Name | 3-Letter Code | 1-Letter Code | Functionally Equivalent Codons |
|---|---|---|---|
| Proline | Pro | P | CCA CCC CCG CCU |
| Phenylalanine | Phe | F | UUC UUU |
| Tryptophan | Trp | W | UGG |

In some embodiments, another consideration for amino acid substitutions include whether or not the residue is located in the interior of a protein or is solvent exposed. For interior residues, conservative substitutions can include in some embodiments: Asp and Asn; Ser and Thr; Ser and Ala; Thr and Ala; Ala and Gly; Ile and Val; Val and Leu; Leu and Ile; Leu and Met; Phe and Tyr; Tyr and Trp. For solvent exposed residues, conservative substitutions can include in some embodiments: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, the Dayhoff matrix, the Grantham matrix, the McLachlan matrix, the Doolittle matrix, the Henikoff matrix, the Miyata matrix, the Fitch matrix, the Jones matrix, the Rao matrix, the Levin matrix, and the Risler matrix (summarized in, for example, Johnson & Overington (1993) J Mol Biol 233:716-738; see also the PROWL resource available at the website of The Rockefeller University, New York, New York, United States of America).

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for Examples 1-5

Synthetic DNA oligonucleotides were purchased from Integrated DNA Technologies. Restriction endonucleases were purchased from Thermo Fisher Scientific. Q5 high-fidelity DNA polymerase and Taq DNA polymerase were purchased from NEB. Products of PCR and restriction digestion were purified by gel electrophoresis and Syd Laboratories Gel Extraction columns. Plasmid DNA was purified using Syd Laboratories Miniprep columns. DNA sequences were analyzed by Eurofins. Potassium D-luciferin was purchased from Thermo Fisher Scientific. Coelenterazine was purchased from Gold Biotechnology. Furimazine (Nano-Glo®) was purchased from Promega. AkaLumine-HCl was purchased from Aobious. CTZ and DTZ were obtained from GoldBio and Haoyuan Chemexpress, respectively. All other chemicals were purchased from Sigma-Aldrich, Fisher Scientific, or VWR and used without further purification. Bruker Avance DRX 600 and Varian NMRS 600 at the UVA Biomolecular Magnetic Resonance Facility was used to record all NMR spectra. Chemical shift (δ) is given in parts per million relative to $^{1}H$ (7.24 p.p.m.) and $^{13}C$ (77.23 p.p.m.) for $CDCl_3$; $^{1}H$ (2.50 p.p.m.) and $^{13}C$ (39.5 p.p.m.) for DMSO-$d_6$; $^{1}H$ (3.31 p.p.m.) and $^{13}C$ (49.15 p.p.m.) for methanol-$d_4$. Splitting patterns are reported as s (singlet), bs (broad singlet), d (doublet), t (triplet), dd (doublet of doublets), and m (multiplet). Coupling constant (J) is given in Hz. High resolution ESI-MS was run on an Agilent 6545 Q-TOF LC/MS system by direct infusion. A Waters Delta Prep ZQ 2000 LC-MS Purification System equipped with a XBridge BEH Amide OBD Prep Column (130 Å, 5 μm, 30 mm×150 mm) was used for preparative reverse-phase HPLC purifications. Nu/J mice were obtained from the Jackson Laboratory (Cat. #002019) and maintained and treated in standard conditions that complied with all relevant ethical regulations. All animal procedures were approved by the UVA Institutional Animal Care and Use Committee. Images were analyzed using the Fiji image analysis software. Microsoft Excel and GraphPad Prism were used to analyze data and prepare figures.

Chemical Synthesis of Compounds 5-bromo-3-phenylpyrazin-2-amine (1a)

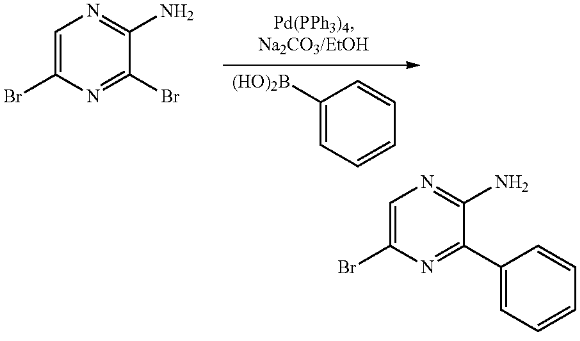

1a

To a solution of $Pd(PPh_3)_4$ (460 mg, 0.4 mmol, 0.1 equiv.) in 200 mL EtOH was added 2-Amino-3,5-dibromopyrazine (1010 mg, 4 mmol, 1 equiv.), 1N $Na_2CO_3$ solution (8 mL, 8 mmol, 2 equiv.) and phenylboronic acid (490 mg, 4 mmol, 1 equiv.). The resultant mixture was stirred at 80° C. under argon for 12 h. The solvent was removed in vacuo and the residue was suspended in 200 mL $ddH_2O$, which was extracted twice with EtOAc (200 mL). The organic layers were combined and dried over anhydrous $Na_2SO_4$, filtered and removed in vacuo. The residue was purified by silica column chromatography with elution (DCM:MeOH=100:1) to yield compound 1a (above) as yellow solid (360 mg, 36%). $^{1}H$ NMR (600 MHz, $CDCl_3$) δ 8.07 (s, 1H), 7.71 (d, J=7.4 Hz, 2H), 7.50 (t, J=7.4 Hz, 2H), 7.45 (t, J=7.4 Hz, 1H), 4.82 (s, 2H). $^{13}C$ NMR (151 MHz, DMSO-$d_6$) δ 152.4, 142.4, 139.3, 135.9, 129.2, 128.8, 128.7, 128.1, 127.9, 123.9. HRMS (ESI-TOF) calcd for $C_{10}H_8BrN_3$ $[M+H]^+$: 249.9902, found: m/z 249.9916.

5-bromo-3-(pyridin-4-yl)pyrazin-2-amine (1b)

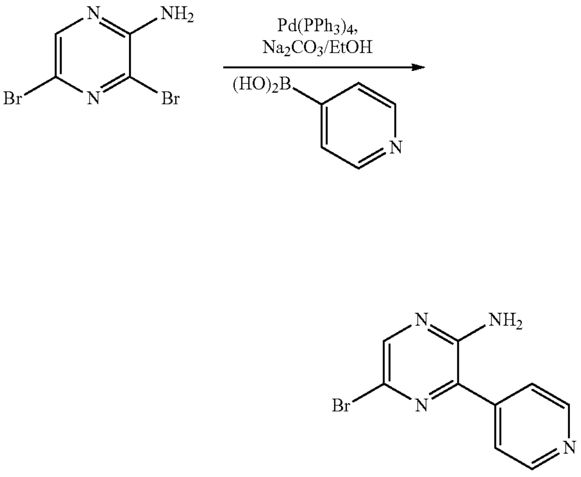

1b

The synthesis of 1b (above) followed the same procedure as 1a, whereas 4-pyridylboronic acid (492 mg, 4 mmol, 1 equiv.) was used. Crude 1b was purified by column chromatography with elution (DCM:MeOH=10:1) to yield 1b as yellow solid (301 mg, 30%). $^{1}H$ NMR (600 MHz, DMSO-$d_6$) δ 8.69 (d, J=6.0 Hz, 2H), 8.17 (s, 1H), 7.67 (d, J=6.0 Hz, 2H), 6.68 (s, 2H). $^{13}C$ NMR (151 MHz, DMSO-$d_6$) δ 152.6, 150.1, 144.1, 143.3, 136.1, 124.0, 122.4. HRMS (ESI-TOF) calcd for $C_9H_7BrN_4$ $[M+H]^+$: 250.9854, found: m/z 250.9845.

3-benzyl-5-phenylpyrazin-2-amine (2a)

2a

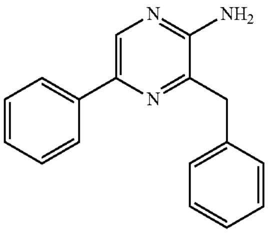

2a (above) was prepared following the published synthesis methods[35]. $^{1}H$ NMR (600 MHz, DMSO-$d_6$) δ 8.41 (s, 1H), 7.89 (d, J=7.4 Hz, 2H), 7.39 (t, J=7.7 Hz, 2H), 7.33 (d, J=7.6 Hz, 2H), 7.27 (q, J=7.7, 7.1 Hz, 3H), 7.18 (t, J=7.3 Hz, 1H), 6.39 (s, 2H), 4.07 (s, 2H). $^{13}C$ NMR (150 MHz, DMSO-$d_6$) δ 153.2, 140.5, 139.2, 138.6, 137.6, 137.4, 129.4, 129.1, 128.7, 127.8, 126.6, 125.2, 39.1. HRMS (ESI-TOF) calcd for $C_{17}H_{15}N_3$ $[M+H]^+$: 262.1266, found: m/z 262.1258.

3,5-diphenylpyrazin-2-amine (2b)

2b

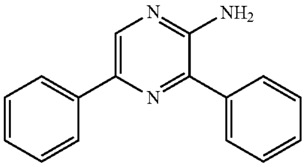

2b was reported previously[33].

5-phenyl-3-(pyridin-4-yl)pyrazin-2-amine (2c)

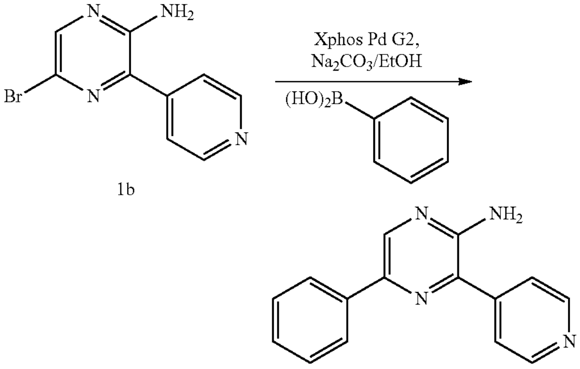

1b

2c

The synthesis and purification of 2c (above) followed the same procedure as 2d, whereas 1b was used as the starting compound and phenylboronic acid (245 mg, 2 mmol, 2 equiv.) was used as boron reagent. Yellow solid (87 mg, 70%). $^{1}$H NMR (600 MHz, DMSO-$d_6$) δ 7.88-7.84 (m, 2H), 7.70 (s, 1H), 7.15 (dt, J=7.8, 1.2 Hz, 2H), 7.12-7.08 (m, 2H), 6.65-6.59 (m, 2H), 6.57-6.51 (m, 1H). $^{13}$C NMR (150 MHz, DMSO-$d_6$) δ 152.3, 150.1, 144.9, 140.0, 139.4, 136.6, 134.7, 128.8, 127.9, 125.0, 122.7. HRMS (ESI-TOF) calcd for $C_{15}H_{12}N_4$ $[M+H]^+$: 249.1062, found: m/z 249.1059.

3-phenyl-5-(pyridin-4-yl)pyrazin-2-amine (2d)

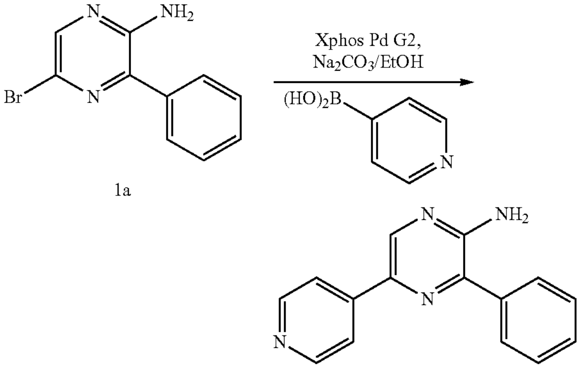

1a

2d

To a mixture of XPhos Pd G2 (79 mg, 0.1 mmol, 0.2 equiv.) and XPhos (24 mg, 0.05 mmol, 0.1 equiv.) in 5 mL EtOH was added 1a (125 mg, 0.5 mmol, 1 equiv.), 1N $Na_2CO_3$ (1 mL, 1 mmol, 2 equiv.) and 4-pyridylboronic acid (246 mg, 2 mmol, 4 equiv.). The resulting mixture was stirred at 80° C. under argon for 12 h. The solvent was then removed in vacuo and the residue was dissolved in 1N HCl (30 mL) and subsequently washed with EtOAc (30 mL). The aqueous layer was collected and the pH was then adjusted to 10 by the addition of 1N NaOH. Product 2d precipitated as yellow solid, which was filtered, washed with EtOAc and dried under reduced pressure overnight. (93 mg, 75%). $^{1}$H NMR (600 MHz, DMSO-$d_6$) δ 8.71 (s, 1H), 8.58 (d, J=6.2 Hz, 2H), 7.94 (d, J=6.2 Hz, 2H), 7.78 (d, J=7.2 Hz, 2H), 7.52 (t, J=7.5 Hz, 2H), 7.46 (t, J=7.3 Hz, 1H), 6.63 (s, 2H). $^{13}$C NMR (150 MHz, DMSO-$d_6$) δ 153.3, 150.1, 144.0, 139.2, 138.6, 137.1, 128.8, 128.2, 119.0. HRMS (ESI-TOF) calcd for $C_{15}H_{12}N_4$ $[M+H]^+$: 249.1062, found: m/z 249.1060.

4-(5-amino-6-benzylpyrazin-2-yl)phenol (2e)

2e

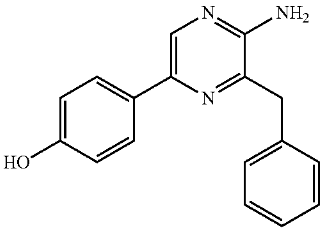

2e (above) was prepared following the published synthesis methods[36]. $^{1}$H NMR (600 MHz, DMSO-$d_6$) δ 9.49 (s, 1H), 8.29 (s, 1H), 7.72 (d, J=8.6 Hz, 2H), 7.33 (d, J=7.3 Hz, 2H), 7.28 (t, J=7.6 Hz, 2H), 7.18 (t, J=7.3 Hz, 1H), 6.79 (d, J=8.6 Hz, 2H), 6.19 (s, 2H), 4.06 (s, 2H). $^{13}$C NMR (150 MHz, DMSO-$d_6$) δ 157.1, 152.0, 139.7, 139.5, 138.3, 135.9, 135.9, 128.9, 128.2, 126.2, 126.1, 115.5, 115.4, 38.7. HRMS (ESI-TOF) calcd for $C_{17}H_{15}N_3O$ $[M+H]^+$: 278.1215, found: m/z 278.1208.

3-phenyl-5-(pyridin-3-yl)pyrazin-2-amine (2f)

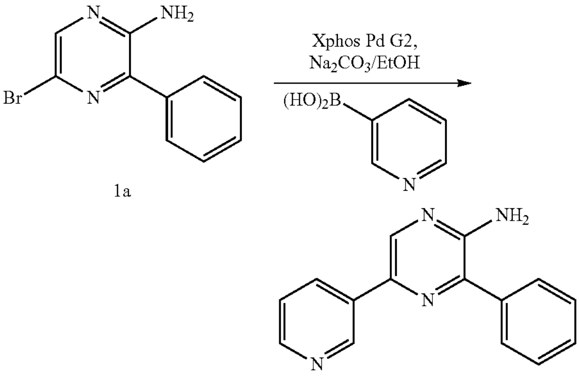

1a

2f

The synthesis and purification of 2f (above) followed the same procedure as 2d, whereas 3-pyridylboronic acid (246 mg, 2 mmol, 4 equiv.) was used. Yellow solid (95 mg, 77%). $^1$H NMR (600 MHz, DMSO-d$_6$) δ 9.19 (s, 1H), 8.64 (s, 1H), 8.54 (d, J=3.9 Hz, 1H), 8.39 (d, J=8.1 Hz, 1H), 7.79 (d, J=7.3 Hz, 2H), 7.53-7.49 (m, 3H), 7.46 (t, J=7.3 Hz, 1H), 6.47 (s, 2H). $^{13}$C NMR (151 MHz, DMSO-d$_6$) δ 152.6, 148.5, 146.3, 138.4, 138.4, 137.3, 137.2, 132.6, 132.3, 132.2, 128.8, 128.6, 128.3. HRMS (ESI-TOF) calcd for $C_{15}H_{12}N_4$ [M+H]$^+$: 249.1062, found: m/z 249.1060.

3-pyridin-4-yl-1,1-diethoxyacetone (4)

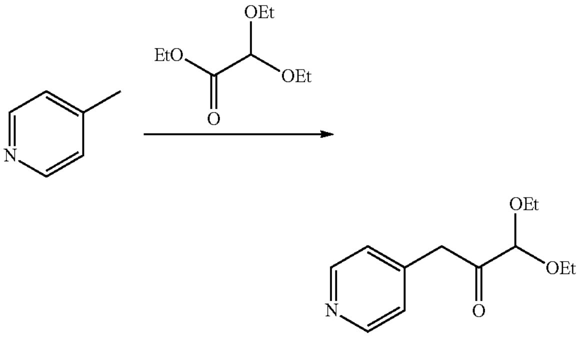

To a solution of 4-methylpyridine (931 mg, 10 mmol, 1 equiv.) in 50 mL anhydrous THF was added potassium tert-butoxide (5.6 g, 50 mmol, 5 equiv.), and the mixture was stirred at room temperature for 10 min. Ethyl diethoxyacetate (3.52 g, 20 mmol, 2 equiv.) in 20 mL THF was then added dropwise over 10 min. The resulting mixture was stirred overnight, and solvent was removed under vacuo. The residue was purified by silica column chromatography with elution (Hexane:EtOAc=1:3 to 100% EtOAc) to yield product as light yellow solid (669 mg, 30%). $^1$H NMR (600 MHz, DMSO-d$_6$) δ 8.47 (d, J=5.8 Hz, 2H), 7.18 (d, J=5.8 Hz, 2H), 4.81 (s, 1H), 3.91 (s, 2H), 3.63 (dq, J=9.7, 7.1 Hz, 2H), 3.54 (dq, J=9.7, 7.1 Hz, 2H), 1.15 (t, J=7.1 Hz, 6H). $^{13}$C NMR (150 MHz, DMSO-d$_6$) δ 202.0, 149.3, 143.2, 125.3, 101.6, 62.8, 42.6, 15.1. HRMS (ESI-TOF) calcd for $C_{12}H_{17}NO_3$ [M+H]$^+$: 224.1208, found: m/z 224.1195.

8-benzyl-6-phenyl-2-(pyridin-4-ylmethyl)imidazo[1,2-a]pyrazin-3(7H)-one (3a)

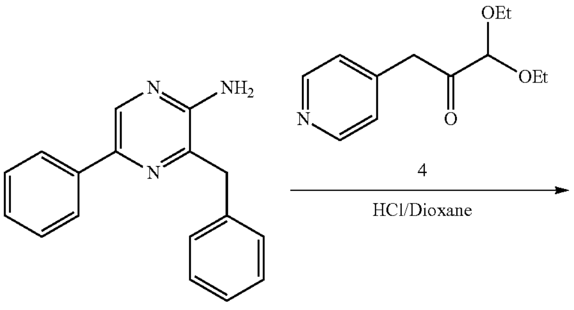

2a

-continued

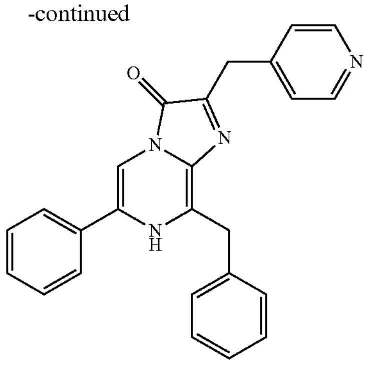

3a

To a solution of 2a (26 mg, 0.1 mmol, 1 equiv.) and 4 (89 mg, 0.4 mmol 4 equiv) in 5 mL degassed 1,4-dioxane was added 0.8 mL 6N HCl. The resulting mixture was stirred at 80° C. in a seal tube for 12 h. The solvent was then removed in vacuo and the residue was dissolved in 1 mL (ACN: $H_2O$=1:1) and next purified with preparative RP-HPLC. (acetonitrile/water=1:99 to 90:10, 20 mL/min, UV 254 nm). Product fractions were combined and lyophilized to give 3a (above) as yellow powder (15 mg, 38%), which has to be stored as solid at −80° C. for long-term stability. $^1$H NMR (600 MHz, Methanol-d$_4$) δ 8.43 (d, J=6.2 Hz, 2H), 7.74 (s, 1H), 7.65 (d, J=6.8 Hz, 2H), 7.49-7.38 (m, 7H), 7.29 (t, J=7.6 Hz, 2H), 7.23 (t, J=7.4 Hz, 1H), 4.42 (s, 2H), 4.23 (s, 2H). $^{13}$C NMR (150 MHz, Methanol-d$_4$) δ 142.6, 137.9, 131.1, 130.4, 130.0, 129.9, 129.1, 128.5, 128.3, 110.1, 49.7. HRMS (ESI-TOF) calcd for $C_{25}H_{20}N_4O$ [M+H]$^+$: 393.1637, found: m/z 393.1630.

6,8-diphenyl-2-(pyridin-4-ylmethyl)imidazo[1,2-a]pyrazin-3(7H)-one (3b)

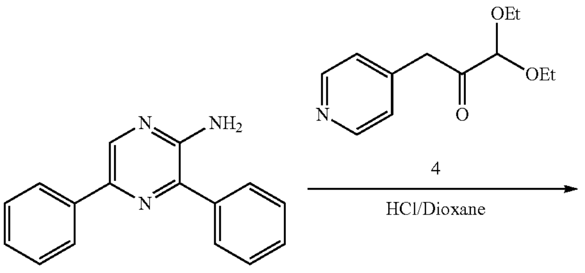

2b

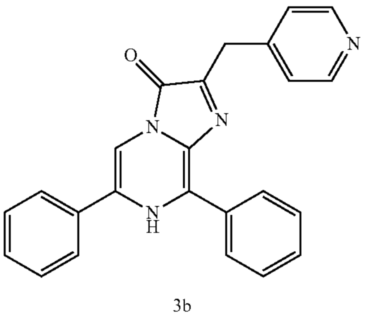

3b

The synthesis and purification of 3b (above) followed the same procedure as 3a, whereas 2b (25 mg, 0.1 mmol, 1 equiv.) was used as the starting compound. Orange powder (8 mg, 21%). 1H NMR (600 MHz, Methanol-$d_4$) δ 8.79 (d, J=6.5 Hz, 2H), 8.50 (s, 1H), 8.15 (d, J=7.2 Hz, 2H), 8.06 (d, J=6.5 Hz, 2H), 8.00 (d, J=7.4 Hz, 2H), 7.69 (t, J=7.4 Hz, 1H), 7.65 (t, J=7.2 Hz, 2H), 7.58 (t, J=7.2 Hz, 2H), 7.56-7.53 (m, 1H), 4.66 (s, 2H). $^{13}C$ NMR (150 MHz, Methanol-$d_4$) δ 161.0, 146.2, 142.7, 139.3, 134.7, 133.3, 133.0, 131.3, 131.0, 130.4, 130.3, 128.8, 128.5, 112.2. HRMS (ESI-TOF) calcd for $C_{24}H_{18}N_4O$ [M+H]$^+$: 379.1481, found: m/z 379.1480.

2-benzyl-6-phenyl-8-(pyridin-4-yl)imidazo[1,2-a]pyrazin-3(7H)-one (3c)

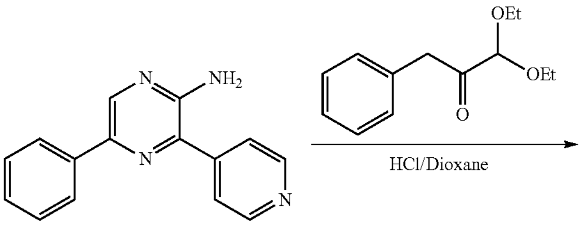

2c

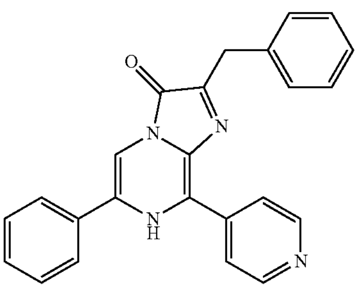

3c

To a solution of 2c (25 mg, 0.1 mmol, 1 equiv.) and 1,1-diethoxy-3-phenylpropan-2-one (89 mg, 0.4 mmol, 4 equiv.) in 5 mL degassed 1,4-dioxane was added 0.8 mL 6 N HCl, and the resulting mixture was stirred at 80° C. in a sealed tube for 12 h. The solvent was then removed in vacuo and the residue was dissolved in 1 mL (ACN:$H_2O$=1:1) and next purified with preparative RP-HPLC. (acetonitrile/water=1:99 to 90:10, 20 mL/min, UV 254 nm). Product fractions were combined and lyophilized to give 3c (above) as brown powder (9 mg, 23%). $^1H$ NMR (600 MHz, Acetonitrile-$d_3$ and $D_2O$, ratio=9:1) δ 9.31 (d, J=6.8 Hz, 2H), 8.84 (d, J=6.8 Hz, 2H), 8.54 (s, 1H), 8.09 (d, J=8.0 Hz, 2H), 7.52 (t, J=7.6 Hz, 2H), 7.44 (t, J=7.3 Hz, 1H), 7.35 (d, J=7.7 Hz, 2H), 7.28 (t, J=7.7 Hz, 2H), 7.24-7.21 (m, 1H), 4.19 (s, 2H). $^{13}C$ NMR (150 MHz, Methanol-$d_4$) δ 143.0, 140.7, 140.1, 139.5, 137.5, 132.0, 130.2, 129.9, 129.6, 129.4, 127.8, 127.5, 127.4, 126.5, 113.8, 33.6. HRMS (ESI-TOF) calcd for $C_{24}H_{18}N_4O$ [M+H]$^+$: 379.1481, found: m/z 379.1477.

2-benzyl-8-phenyl-6-(pyridin-4-yl)imidazo[1,2-a]pyrazin-3(7H)-one (3d)

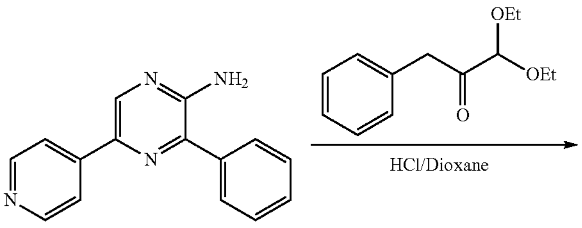

2d

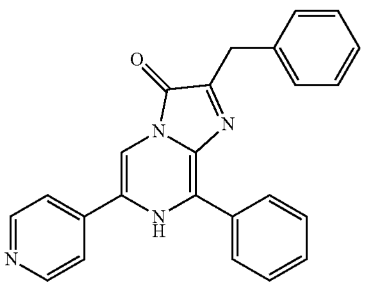

3d

The synthesis and purification of 3d (above) followed the same procedure as 3c, whereas 2d (25 mg, 0.1 mmol, 1 equiv.) was used as the starting compound. Yellow powder (6 mg, 16%). $^1H$ NMR (600 MHz, Methanol-$d_4$) δ 9.52 (s, 1H), 9.01 (d, J=6.8 Hz, 2H), 8.97 (d, J=6.8 Hz, 2H), 8.15-8.11 (m, 2H), 7.71-7.66 (m, 3H), 7.35-7.30 (m, 7.4 Hz, 4H), 7.25 (t, J=7.4 Hz, 1H), 4.36 (s, 2H). $^{13}C$ NMR (150 MHz, Methanol-$d_4$) δ 154.5, 148.8, 143.5, 140.4, 138.4, 137.2, 135.0, 133.1, 130.6, 130.4, 130.4, 130.1, 129.8, 129.5, 128.7, 128.3, 125.3, 117.2, 30.5. HRMS (ESI-TOF) calcd for $C_{24}H_{18}N_4O$ [M+H]$^+$: 379.1481, found: m/z 379.1476.

8-benzyl-6-(4-hydroxyphenyl)-2-(pyridin-4-ylmethyl)imidazo[1,2-a]pyrazin-3(7H)-one (3e)

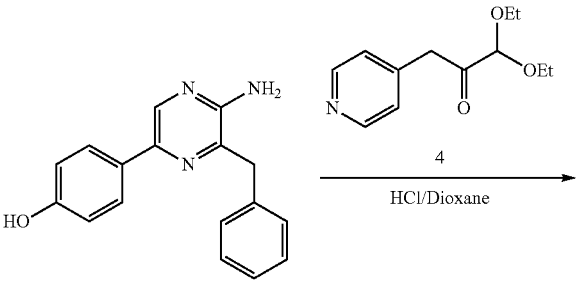

2e

-continued

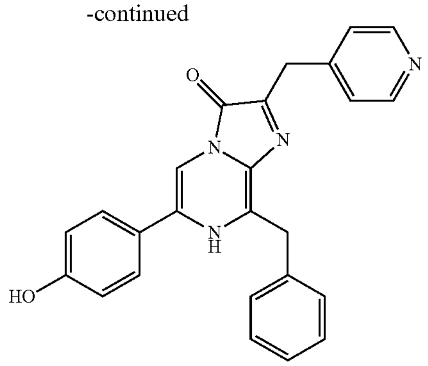

3e

The synthesis and purification of 3e (above) followed the same procedure as 3a, whereas 2e (28 mg, 0.1 mmol, 1 equiv.) was used as the starting compound. Yellow powder (14 mg, 34%). $^{1}$H NMR $^{1}$H NMR (600 MHz, Methanol-$d_4$) δ 8.78 (d, J=5.2 Hz, 2H), 8.08 (d, J=5.2 Hz, 2H), 8.01 (s, 1H), 7.72 (d, J=7.7 Hz, 2H), 7.53 (d, J=7.7 Hz, 3H), 7.42 (d, J=7.4 Hz, 2H), 7.31 (t, J=7.4 Hz, 2H), 7.25 (t, J=7.7 Hz, 1H), 4.58 (s, 2H), 4.52 (s, 2H). $^{13}$C NMR (150 MHz, Methanol-$d_4$) δ 161.2, 142.6, 137.1, 130.3, 130.2, 130.1, 129.1, 128.7, 117.3, 111.3. HRMS (ESI-TOF) calcd for $C_{25}H_{20}N_4O_2$ [M+H]$^+$: 409.1586, found: m/z 409.1585.

2-benzyl-8-phenyl-6-(pyridin-3-yl)imidazo[1,2-a]pyrazin-3(7H)-one (3f)

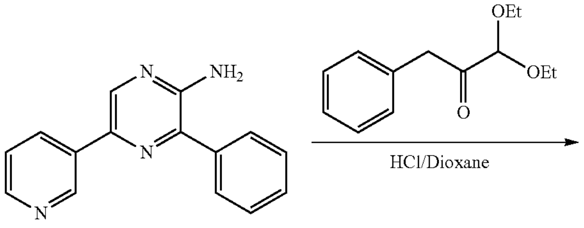

2f

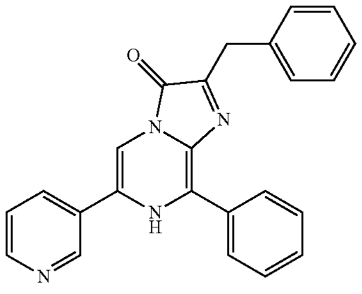

3f

The synthesis and purification of 3f (above) followed the same procedure as 3c, whereas 2f (25 mg, 0.1 mmol, 1 equiv.) was used as the starting compound. Orange powder (8 mg, 21%). $^{1}$H NMR (600 MHz, Methanol-$d_4$) δ 9.73 (s, 1H), 9.47 (d, J=8.3 Hz, 1H), 9.36 (s, 1H), 8.99 (d, J=5.6 Hz, 1H), 8.32-8.27 (m, 1H), 8.09 (d, J=6.6 Hz, 2H), 7.72-7.66 (m, 3H), 7.32 (7.67-7.30, 4H), 7.25 (t, J=7.0 Hz, 1H), 4.36 (s, 2H). $^{13}$C NMR (150 MHz, Methanol-$d_4$) δ 148.6, 145.3, 142.9, 141.5, 138.3, 137.4, 137.2, 134.8, 133.1, 130.5, 130.4, 130.1, 129.5, 129.1, 128.3, 128.2, 121.6, 114.8, 30.3. HRMS (ESI-TOF) calcd for $C_{24}H_{18}N_4O$ [M+H]$^+$: 379.1481, found: m/z 379.1478.

Plasmid and Library Construction

Polymerase chain reactions (PCRs) with various synthetic oligonucleotide pairs (see Table 5) were used to amplify genetic elements. To create a gene library with randomization at residues 20 and 21, oligo pairs pBAD-F and L20D21NNK-R, L20D21NNK-F and pBAD-R, were used to amplify two individual fragments from pBAD-teLuc; the corresponding products were used for assembly in a subsequent overlap PCR reaction by using oligos pBAD-F and pBAD-R. The assembled full-length fragment was digested with Xho I and Hind III restriction enzymes and ligated into a predigested, compatible pBAD/His B plasmid. Similarly, pBAD-F, 29VSSNNK-R, 29VSSNNK-F, and pBAD-R were used to create a library with randomization at residues 29, 30, and 31. To introduce random mutations across the gene, Taq DNA polymerase was used in all reactions with 0.2 mM $MnCl_2$ along with unbalanced dNTPs to promote amplification errors. To create mammalian expression plasmids, HindIII-pyr-F-Koz and pyr-R-XhoI were used to amplify the LumiLuc gene fragment, which was further treated with Hind III and Xho I restriction enzymes and ligated into a predigested, compatible pcDNA3 plasmid. The Akaluc gene was synthesized by Eurofins, and cloned into a pBAD plasmid for bacterial expression and a pcDNA3 plasmid for mammalian expression, by using Aka-F-XhoI and Aka-R-HindIII or Aka-F-HindIII-Kozak and Aka-R-XhoI oligonucleotides. To build mScarlet-LumiLuc fusion library, mScarlet-F-XhoI and mScar-NNK-pyr-R oligonucleotides were used to amplify mScarlet-I gene, while mScar-NNK-pyr-F and pyr-R-HindIII oligonucleotides were used for LumiLuc cloning, which were subsequently assembled by overlap PCR reaction. The product was digested with Xho I and Hind III restriction enzymes and ligated into a predigested, compatible pBAD/His B plasmid. The LumiScarlet gene was cloned into pcDNA3 for mammalian expression using HindIII-mScarlet-F-Koz and pyr-R-XhoI oligonucleotides. All ligation products were used to transform *Escherichia coli* DH10B electrocompetent cells, which were next plated on LB agar plates supplemented with ampicillin (100 μg/mL).

Library Screening

DH10B cells containing luciferase mutants were plated on LB agar plates supplemented with ampicillin (100 μg/mL) and L-arabinose (0.02%, w/v %) and incubated at 37° C. overnight to form bacterial colonies. Agar plates were left at room temperature for another 6 h, and this was followed by bioluminescence imaging using a luminescence dark box (UVP Bio Spectrum) equipped with a QSI 628 cooled CCD camera (Quantum Scientific Imaging). Digital images were acquired after spraying about 200 μL of 10 μM substrates to each agar plate, and next, images were processed with the Fiji image analysis software to derive bioluminescence intensities of individual colonies. For each round of selection, the brightest 20 colonies from a total of about 10,000 colonies were chosen and inoculated in 5 mL liquid LB broth containing ampicillin (100 μg/mL) and L-arabinose (0.02%, w/v %). After overnight growth at 37° C. and 250 r.p.m., the cultures were moved onto a shaker at room temperature for another 6 h. 500 μL cell cultures were centrifuged and next lysed with 100 μL B-PER (Thermo Fisher Scientific). Next, to 1 μL lysate from each sample was added 100 μL substrate at a final concentration of 20 μM in assay buffer. Bioluminescence activities of individual samples were measured on a Synergy Mx Microplate Reader (BioTek). Kinetics were followed for 0.1 s signal integration every 60 s for a total of 20 min. Top three Mutants showing exceptionally high bioluminescence activities or extended kinetics were chosen for next-round selection, sequencing, and other additional characterization. mScarlet-I and LumiLuc fusion libraries were screened for high BRET efficiency using a 600-700 nm bandpass filter. 20 colonies were picked from each library and inoculated in 5 mL liquid LB broth containing ampicillin (100 μg/mL) and L-arabinose (0.02%, w/v %). The cell lysates were prepared with B-PER and the bioluminescence emission spectra were measured by adding 20 μM 8pyDTZ. The construct showed highest BRET efficiency was designated LumiScarlet.

In Vitro Bioluminescence Characterization

Luciferases were expressed and purified as previously described.[33] A Synergy Mx Microplate Reader (BioTek) was used for all in vitro bioluminescence characterizations. 50 μL of luciferin substrates was injected into the wells of white 96-well plates containing 50 μL of pure enzymes in assay buffer (1 mM CDTA, 0.5% Tergitol NP-40, 0.05% Antifoam 204, 150 mM KCl, 100 mM MES pH 6.0, 1 mM DTT, and 35 mM thiourea). The final concentrations of all enzymes were 20 pM. Measurements were taken every 30 s post injection (0.1 s integration and 10 s shaking during intervals). Akaluc bioluminescence assays were performed at final concentration of 10 nM Akaluc and 100 μM AkaLumine in an assay buffer contained 30 mM MOPS (pH 7.0), 1.5 mM ATP, and 5 mM $MgSO_4$. To derive values for apparent Michaelis constants (Km), substrate concentrations varied from 0.78 to 50 μM, and peak bioluminescence intensities at individual substrate concentrations were used to fit the Michaelis-Menten equation. To record emission spectra, 50 μL of 20 μM substrates were injected into 50 μL of 2 nM pure enzymes, and the bioluminescence spectra were collected with 0.1 s integration and 1 nm increments from 350 to 750 nm.

Chemiluminescence Measurement 0.63 g ammonium bicarbonate was dissolved in 12 mL water and 24 mL acetonitrile containing 30% aqueous hydrogen peroxide, resulting in an active peroxymonocarbonate solution. The solution was left at room temperature for 10 min. Each stock solution containing synthetic analogues (500 μM, 100 μL) was dispensed into wells of a 96-well plate, and chemiluminescence was triggered by addition of 100 μL of the peroxymonocarbonate solution. Light emission was recorded on a Synergy Mx Microplate Reader (BioTek) with 0.1 s integration and 1 nm increments from 350 to 750 nm.

Mammalian Cell Culture, Transfection, and Imaging

HEK 293T cells were cultured and transfected as previously described.[33] The number and density of cells in Dulbecco's phosphate-buffered saline (DPBS) were determined using a hemocytometer. Cells were next diluted in DPBS to gain the desired numbers in each 50 μL solution. To use the luminescence dark box to directly image cells, we added luciferase-expressing HEK 293T cells (5,000 cells per well with ~70% transfection efficiency) and the corresponding luciferin substrates into wells of a white-wall, 96-well plate. Bioluminescence was imaged using a luminescence dark box immediately after substrate addition. The camera exposure time was set at 2 s. A Chroma Red 600-700 nm filter was used to acquire far-red emission. All images were analyzed using the Fiji image analysis software.

Generation of Luciferase-Expressing Stable Cell Lines

HeLa cells were cultured at 37° C. with 5% $CO_2$ in Dulbecco's Modified Eagle's Medium (DMEM) supplemented with 10% fetal bovine serum (FBS). HeLa cells were transfected with pcDNA3-teLuc, pcDNA3-Antares2, pcDNA3-LumiLuc, pcDNA3-LumiScarlet, or pcDNA3-Akaluc as previously described.[33] 48 h after transfection, cells were passed into fresh DMEM containing 10% FBS and 1 mg/mL G418. The medium was removed and replaced every 3 days. Stable polyclonal cell lines were generated after ~2 weeks of G418 selection.

Xenograft Mouse Model

HeLa cells stably expressing luciferases were dissociated with trypsin and re-suspended in 10 mL DMEM. Cell numbers were determined using a hemocytometer, and cell viability was determined using a trypan blue exclusion test. $10^4$ or $10^5$ cells were re-suspended in 100 μL FBS-free DMEM containing 50% Matrigel matrix (Corning). 8-week-old female nude mice were first anesthetized using isoflurane. Cells were subcutaneously injected into the left and right dorsolateral trapezius regions or thoracolumbar regions. Mice were recovered on heat pads for 5 min while cells were allowed to settle. On day 1, 3, 5, 7, 14, and 28 post tumor implants, mice were subsequently imaged using a Caliper IVIS Spectrum (Perkin Elmer) approximately 5 min after intravenous (i.v.) administration of corresponding luciferins (100 μL solution for indicated doses). DTZ was dissolved in a 100 μL solution containing 8% glycerol, 10% ethanol, 10% hydroxypropyl-β-cyclodextrin, and 35% PEG 400 in water. 8pyDTZ and AkaLumine-HCl was dissolved in normal saline. All solutions were passed through 0.22 μm pore filters before administrations. The following conditions were used for image acquisition: open filter for total bioluminescence, exposure time=60 s (Day 1, 3, and 5); 30 s (Day 7); 10 s (Day 14); 3 s (Day 28), binning=small, field of view=21.6×21.6 cm, and f/stop=1. Image analysis was performed using the Living Image 4.3.1 software.

Deep-Tissue Mouse Model $10^6$ HeLa cells stably expressing either LumiLuc, LumiScarlet or Akaluc were i.v. injected to female nude mice. After 4 h, images were acquired using a Caliper IVIS Spectrum immediately after i.v. delivery 0.2 μmol 8pyDTZ or 1.5 μmol AkaLumine-HCl in 100 μL normal saline. The following conditions were used for image acquisition: open filter for total bioluminescence, exposure time=10 s, binning=small, field of view=21.6×21.6 cm, and f/stop=1.

Fluorescence Imaging of ATP in Mammalian Cells

HEK293T and HeLa cells were cultured and transfected as aforementioned. Images were acquired on a Leica DMi8 inverted microscope equipped with the SPE confocal module. Cells were cultured in DMEM (no phenol red) with 4.5 g/mL glucose. 405 and 488 nm laser was used to excite PercevalHR, and emission was collected from 510 nm to 600 nm. Intervals between each image were 5 second. 50 μM 8pyDTZ was added to cells. For the internal calibration purpose, iodoacetic acid (IAA) was added to a final concentration of 5 mM to completely deplete intracellular ATP. pHRFP was also used to monitor the cellular pH change before and after addition of 50 μM 8pyDTZ.

Statistical Analysis.

Unpaired two-tailed t-tests were used to determine all p-values. No statistical methods were used to predetermine the sample size. Animals were randomly assigned to receive various treatments. Unless otherwise indicated, data are shown as mean±s.d., and error bars in figures represent s.d.

Example 1

Design and Synthesis of Pyridyl CTZ and DTZ Analogs with Enhanced Water Solubility Despite that recent studies have synthesized and tested a number of CTZ analogs with NanoLuc,[18, 19] the luciferase has not yet been optimized to pair with these new substrates and the water solubility issue of the substrates has not yet been tackled systematically. Thus, a need remained for CTZ and DTZ analogs with improved water solubility.

The chemical structures of coelenterazine (CTZ), furimazine (FRZ) and diphenylterazine (DTZ) are provided below.

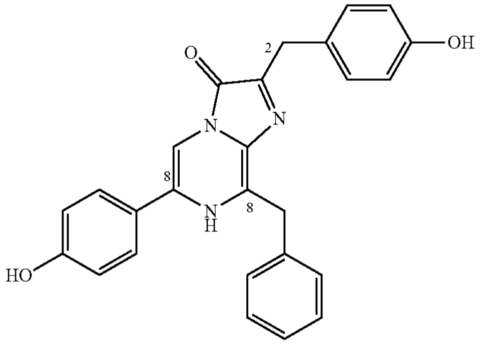

coelenterazine
(CTZ)

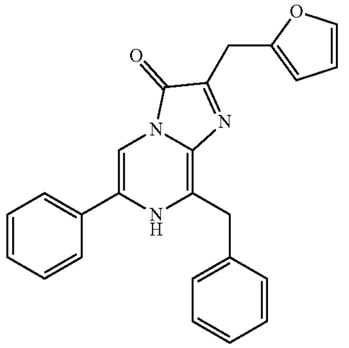

furimazine
(FRZ)

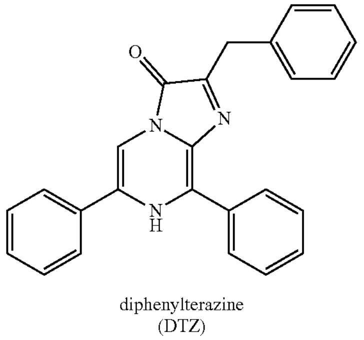

diphenylterazine
(DTZ)

The need was fulfilled, as disclosed herein, by using the concept of bioisostere replacements in medicinal chemistry. Pyridine is considered a biocompatible N-heterocycle substituent for benzene with enhanced water solubility, because pyridine-containing molecules can be readily turned into pyridinium salts. Therefore, a convergent synthetic route was designed to prepare a series of CTZ and DTZ analogs with pyridyl isomer substitutions at the C-2, C-6 and C-8 positions of the imidazopyrazinone core (Scheme 1, below). Briefly, Suzuki or Negishi cross-coupling reactions were first used to regioselectively functionalize 2-amino-3,5-dibromopyrazine with either pyridyl, phenyl, or benzyl functional groups to give monosubstituted products (1a-c), which were subsequently derivatized via Suzuki cross-coupling reactions to afford disubstituted intermediates (2a-f, see structures and synthetic methods above). In the second cross-coupling step, the XPhos-Pd-G2 catalyst was used to enhance reaction yields and minimize the protodeboronation of pyridyl boronic acids.[20] An acid-catalyzed ring closing reaction[21] in dioxane was also utilized to derive various pyridyl CTZ and DTZ analogs (3a-f, Table 2) from the disubstituted intermediates and corresponding α-ketoacetals.

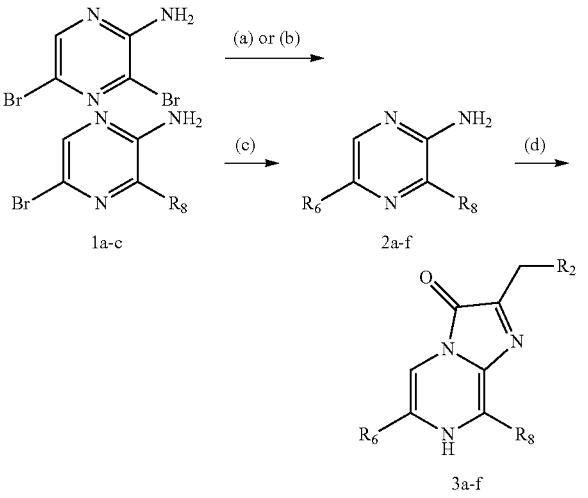

Scheme 1. Synthesis of pyridyl CTZ and DTZ analogs. (a) Suzuki coupling: $Pd(PPh_3)_4$, $Na_2CO_3$, $R_8$—$B(OH)_2$, and EtOH; (b) Negishi coupling: $PhCH_2MgCl$, $ZnCl_2$, $(PPh_3)_2PdCl_2$, and THF; (c) Suzuki coupling: XPhos-Pd-G2, $Na_2CO_3$, $R_6$—$B(OH)_2$, and EtOH; (d) Acid-catalyzed ring closing: corresponding α-ketoacetal, HCl, and dioxane.

Figure 2A:
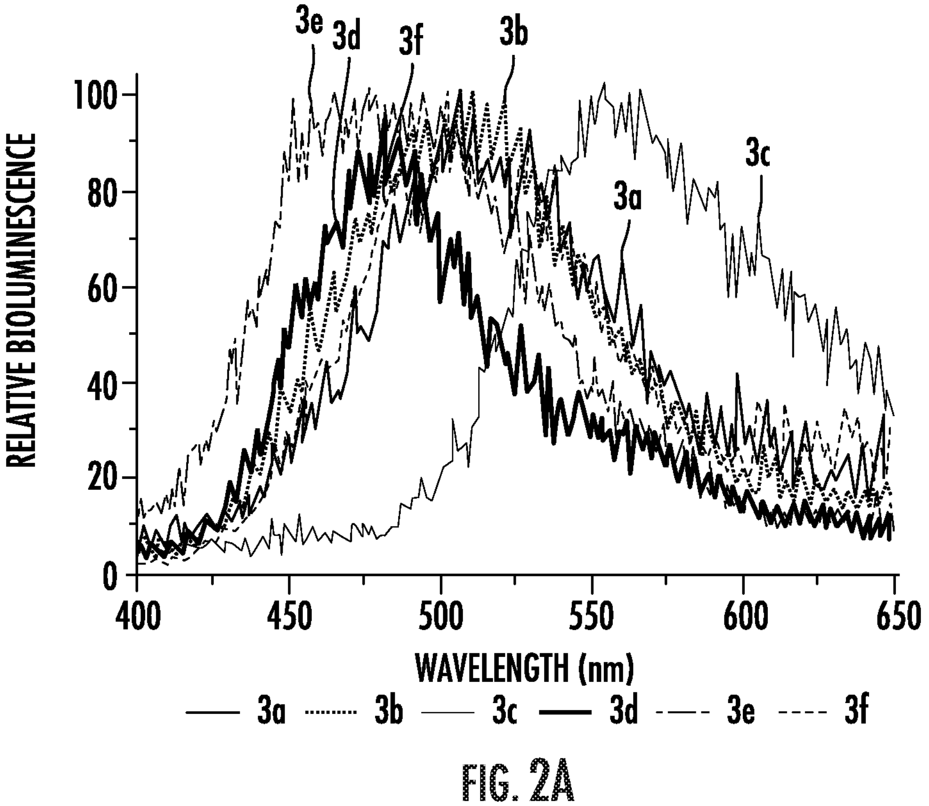
FIGS. 2A and 2B show chemiluminescence (FIG. 2A) and bioluminescence (FIG. 2B) spectra for synthetic CTZ and DTZ analogs described herein. Chemiluminescence was initiated with peroxymonocarbonate generated in situ. Bioluminescence was determined with 1 nM teLuc in PBS.
Figure 2B:
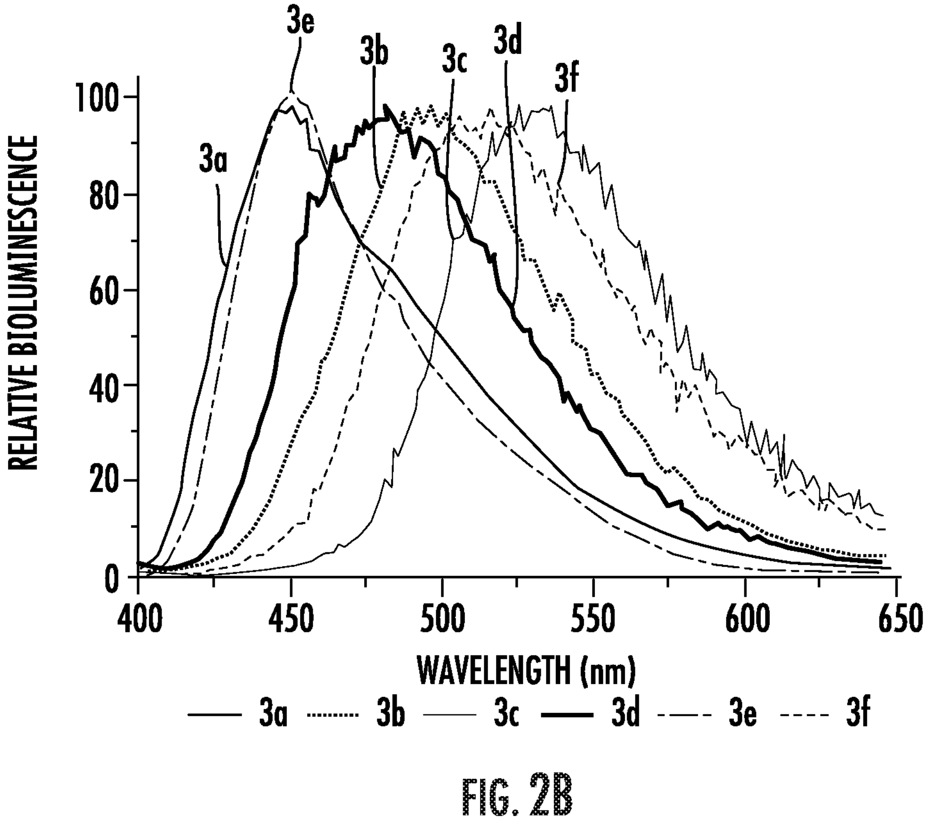
Figure 3A:
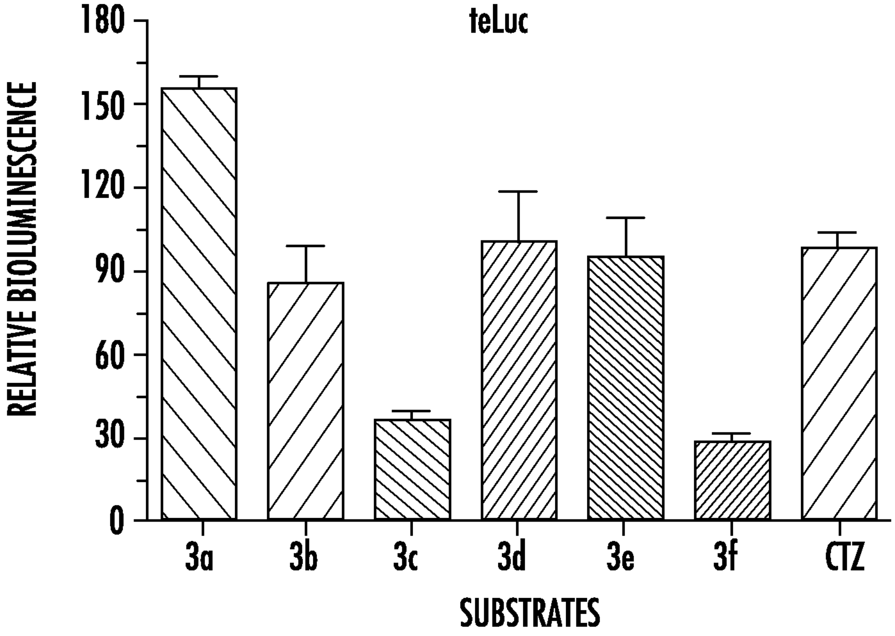
FIGS. 3A through 3D show the relative bioluminescence intensities of various luciferases. Total signals were integrated for the first 10 min after injection of indicated substrates (the final concentrations were 25 μM) in the presence of 1 nM purified (FIG. 3A) teLuc and (FIG. 3B) NanoLuc, or 10 nM (FIG. 3C) RLuc8 and (FIG. 3D) aequorin in PBS. Values were normalized to the intensity of CTZ in each group.
Figure 3B:
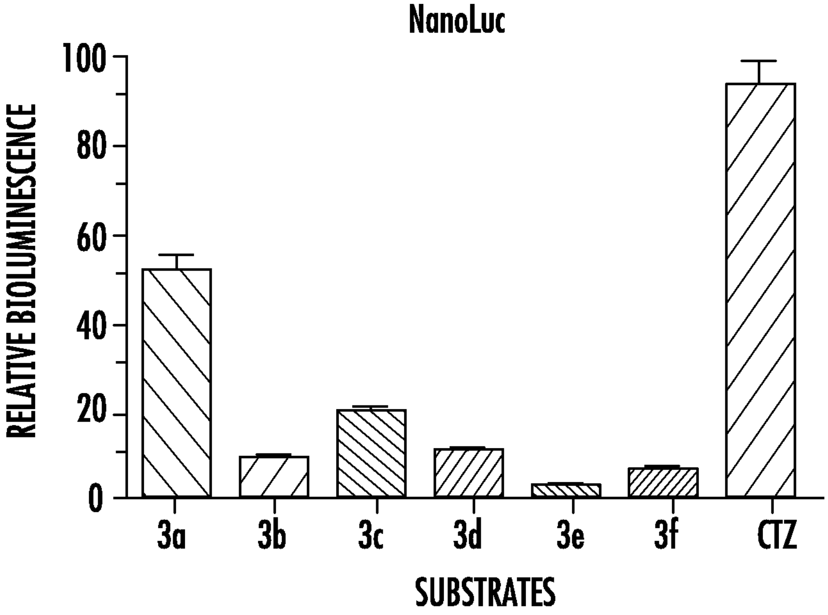
Figure 3C:
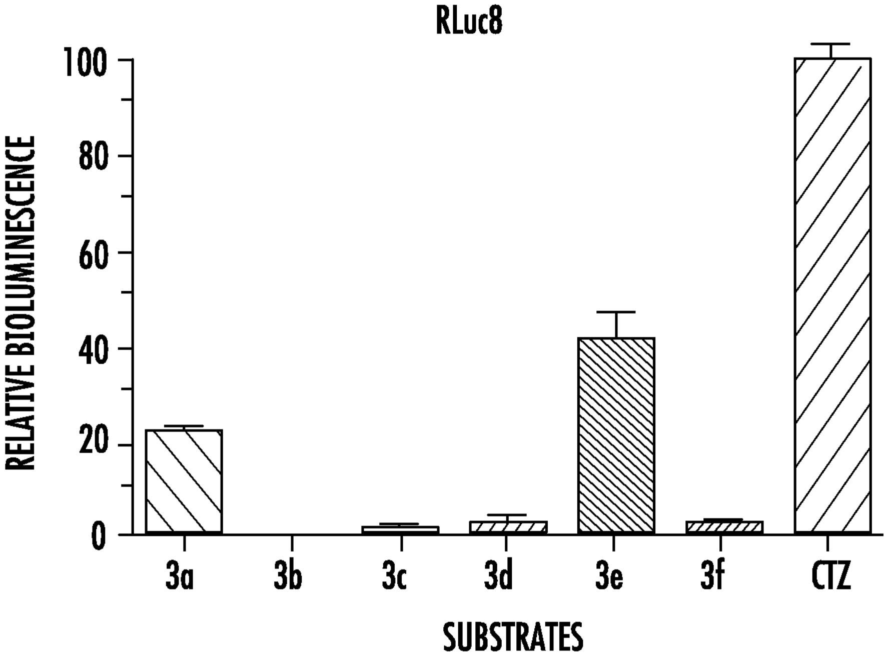
Figure 3D:
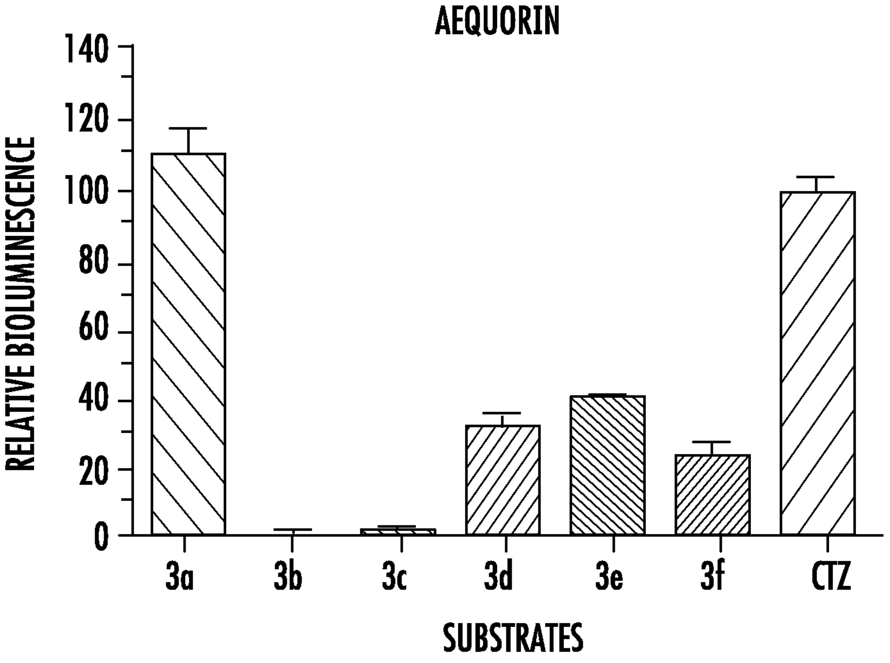

Turbidimetric solubility assays[22] were used to evaluate water solubility of these CTZ and DTZ analogs (Table 2). Surprisingly, the newly synthesized pyridyl analogs enhanced the solubility by 4- to 14-fold as compared to CTZ and DTZ. The autoluminescence and stability of these new analogs was also evaluated, the results of which indicated that they are comparable or even better than CTZ and FRZ. Moreover, their chemiluminescence was also evaluated, because the wavelength of bioluminescence is often related to the wavelength of substrate chemiluminescence, although the luciferase enzyme provides further electrostatic tuning which can reshape the emission (FIG. 2). In addition, the bioluminescence of these new substrates in the presence of several representative, ATP-independent luciferases such as RLuc8, NanoLuc, teLuc, and aequorin was evaluated (FIGS. 3A-3D).[23]

Although each luciferase has different substrate preferences, the compound 3a (pyCTZ) generated strong blue bioluminescence in the presence of each of these tested luciferases. When paired with aequorin, the bioluminescence intensity of pyCTZ was comparable to native CTZ, suggesting that pyCTZ may be directly used to replace CTZ for aequorin-based calcium sensing.[24] Furthermore, compared to DTZ, compounds 3c (8pyDTZ), and 3f were able to emit red-shifted chemiluminescence and/or bioluminescence, while 3b and 3d (6pyDTZ) caused hypsochromic shift (Table 2). Molecular mechanisms governing the spectral shift properties of these synthetic substrates remain to be investigated. Because 3c showed the most red-shifted emission and red-shifted photons can penetrate through tissue better,[25] 3c (8pyDTZ) was selected as the candidate substrate for further development of an optimized, red-shifted luciferase-luciferin pair.

TABLE 2

Chemical and photoluminescence properties of synthetic pyridyl CTZ and DTZ analogs.

| Compound | $R_6$ | $R_8$ | $R_2$ | Bio-luminescence $^a\lambda_{max}$ (nm) | Chemi-luminescence $^b\lambda_{max}$ (nm) | Water Solubility (μM) |
|---|---|---|---|---|---|---|
| 3a | 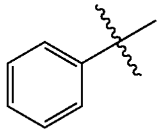 [SMILES: *c1ccccc1] | 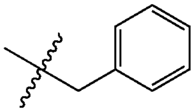 [SMILES: *Cc1ccccc1] | 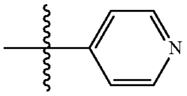 [SMILES: *c1ccncc1] | 451 | 505 | 1416 |
| 3b | 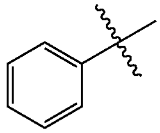 [SMILES: *c1ccccc1] | 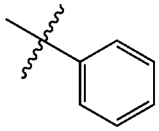 [SMILES: *c1ccccc1] | 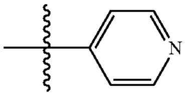 [SMILES: *c1ccncc1] | 497 | 506 | 1813 |
| 3c | 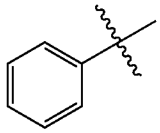 [SMILES: *c1ccccc1] | 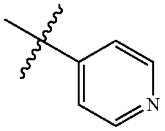 [SMILES: *c1ccncc1] | 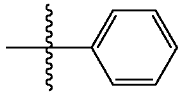 | 532 | 555 | 1711 |
| 3d | 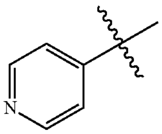 [SMILES: *c1ccncc1] | 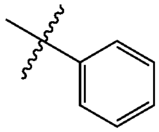 [SMILES: *c1ccccc1] | 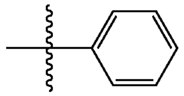 [SMILES: *c1ccccc1] | 483 | 492 | 1736 |
| 3e | 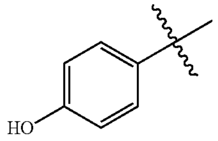 [SMILES: *c1ccc(O)cc1] | 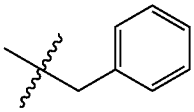 [SMILES: *Cc1ccccc1] | 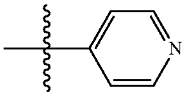 [SMILES: *c1ccncc1] | 450 | 465 | 987 |
| 3f | 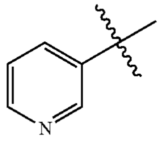 [SMILES: *c1cccnc1] | 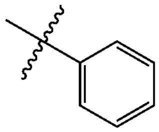 [SMILES: *c1ccccc1] | 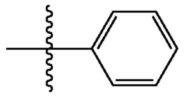 | 518 | 503 | 1562 |
| CTZ | 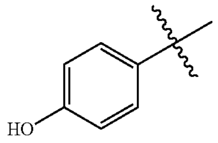 [SMILES: *c1ccc(O)cc1] | 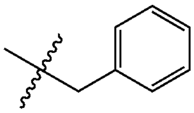 [SMILES: *Cc1ccccc1] | 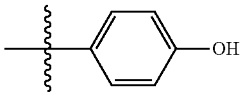 [SMILES: *c1ccc(O)cc1] | 455 | 461 | 256 |
| DTZ | 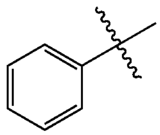 [SMILES: *c1ccccc1] | 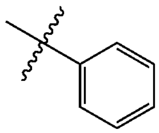 [SMILES: *c1ccccc1] | 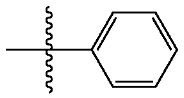 | 502 | 510 | 131 |

Note:
[a]Determined with 1 nM teLuc in PBS;
[b]Triggered by peroxymonocarbonate formed in situ.

The chemical structures of pyCTZ (3a in Table 2), 8pyDTZ (3c in Table 2) and 6pyDTZ (3d in Table 2) are provided below, as well as in FIG. 1.

3a

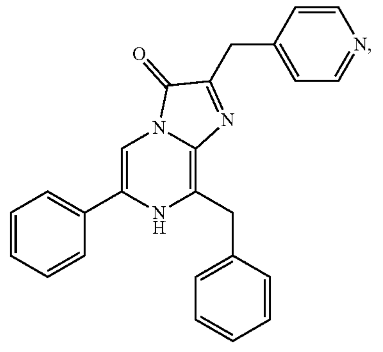

pyCTZ

3c

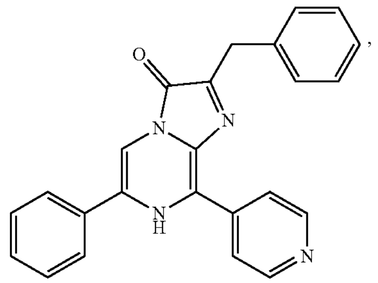

8pyDTZ

3d

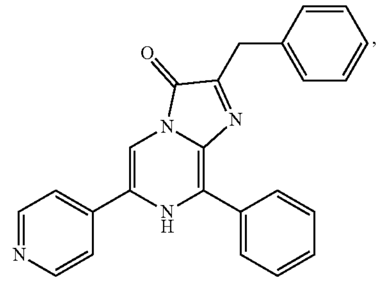

6pyDTZ

Example 2

Figure 4A:
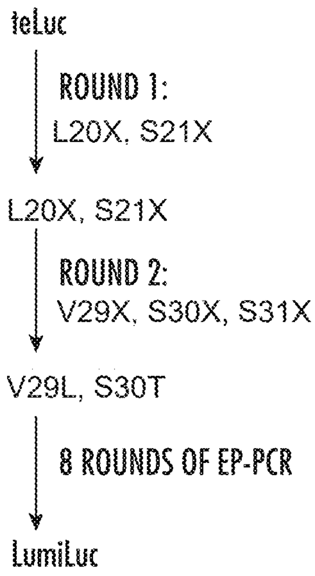
FIGS. 4A through 4D show results of efforts to engineer a LumiLuc luciferase.
Figure 4B:
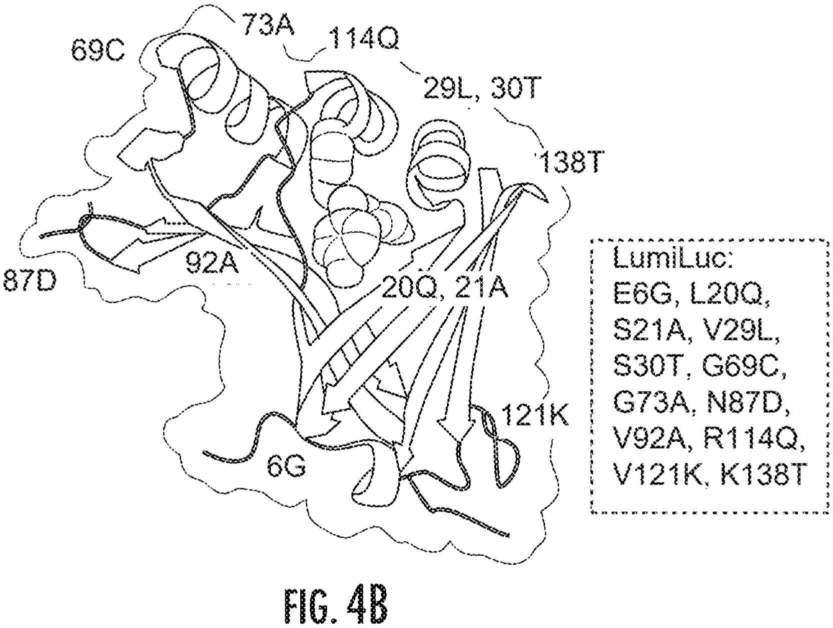
Figure 4C:
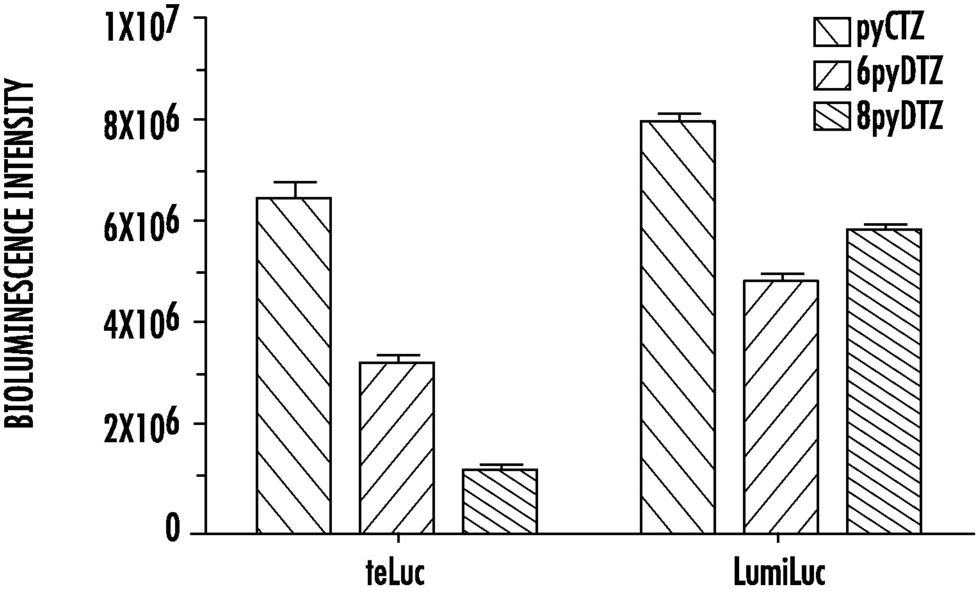
Figure 5:
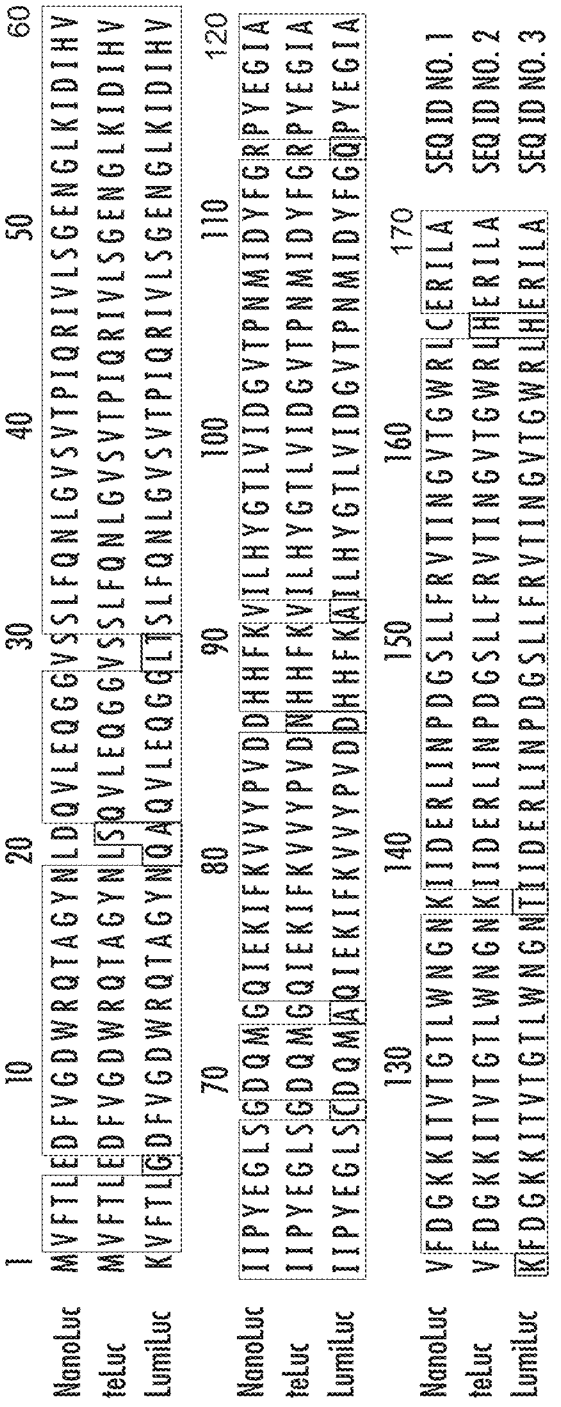
FIG. 5 shows alignments of primary polypeptide sequences of NanoLuc (SEQ ID NO. 1), teLuc (SEQ ID NO. 2), and LumiLuc (SEQ ID NO. 3). teLuc mutations are highlighted. Likewise, all LumiLuc mutations are highlighted.

Directed Evolution of the teLuc Luciferase for Improved Brightness teLuc was previously optimized for DTZ, a substrate with conjugated disubstitutions on the imidazopyrazinone core. 8pyDTZ exhibits about 30 nm red-shift but the emission of teLuc-8pyDTZ has been greatly attenuated compared to teLuc-DTZ. teLuc was then engineered for increased photon flux in the presence of 8pyDTZ. On the basis of a published apo-nanoKAZ structure[26] and our computational model,[7] random mutations were first introduced to residues 20 and 21 close to a putative substrate-binding pocket (FIGS. 4A and 4B). After screening for improved mutants, residues 28, 30, and 31 located deeper in the putative catalytic site were further randomized. From the first two rounds of protein engineering, a teLuc-L20Q/S21A/V29L/S30T mutant was identified, to which random mutations were further introduced using error-prone PCR. After eight additional rounds of mutagenesis and screening, a LumiLuc luciferase was derived with 12 total mutations and about 5-fold enhancement of 8pyDTZ bioluminescence from teLuc (FIGS. 4C and 5).

Figure 6A:
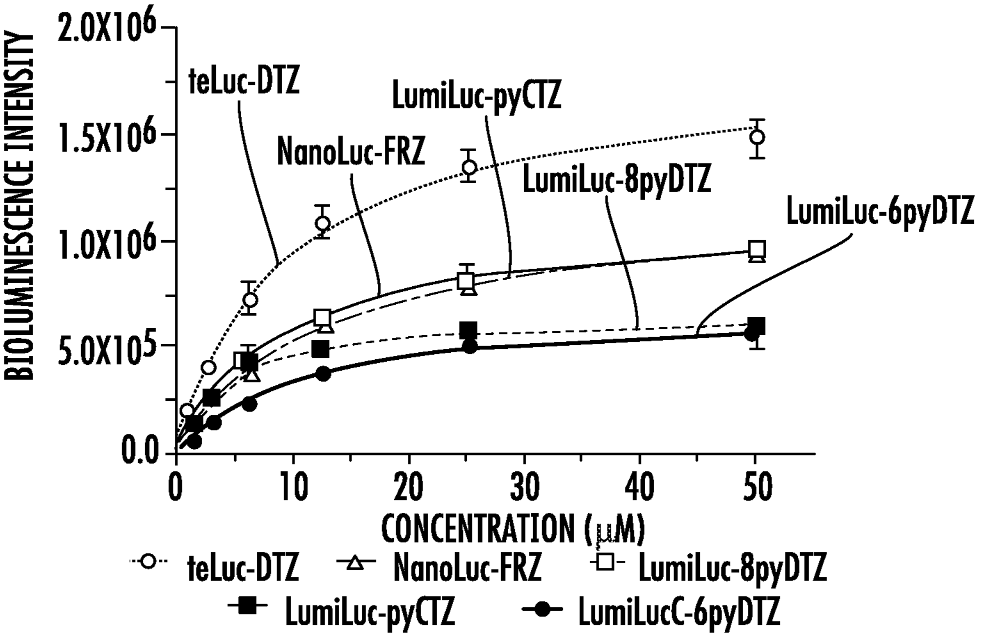
FIGS. 6A through 6C show the comparison of luciferase-luciferin pairs in enzyme-based assays.

The resultant LumiLuc-8pyDTZ pair has an emission peak at 525 nm. Its in vitro maximal photon emission rate (Vmax) is about 60% and about 36% of NanoLuc-FRZ and teLuc-DTZ, respectively. The apparent Michaelis constant (KM) of LumiLuc-8pyDTZ was 4.6 μM, lower than that of teLuc-DTZ or NanoLuc-FRZ (FIG. 6A). This reduced KM is practically beneficial, since LumiLuc-8pyDTZ would be relatively brighter when effective substrate concentrations are limited, such as in live cells (FIG. 6B) and in vivo. Similar to NanoLuc and teLuc, the bioluminescence kinetics of LumiLuc is flash-type in phosphate buffer saline (PBS) and glow-type in a specially formulated assay buffer (FIG. 6C).[12]

Figure 4D:
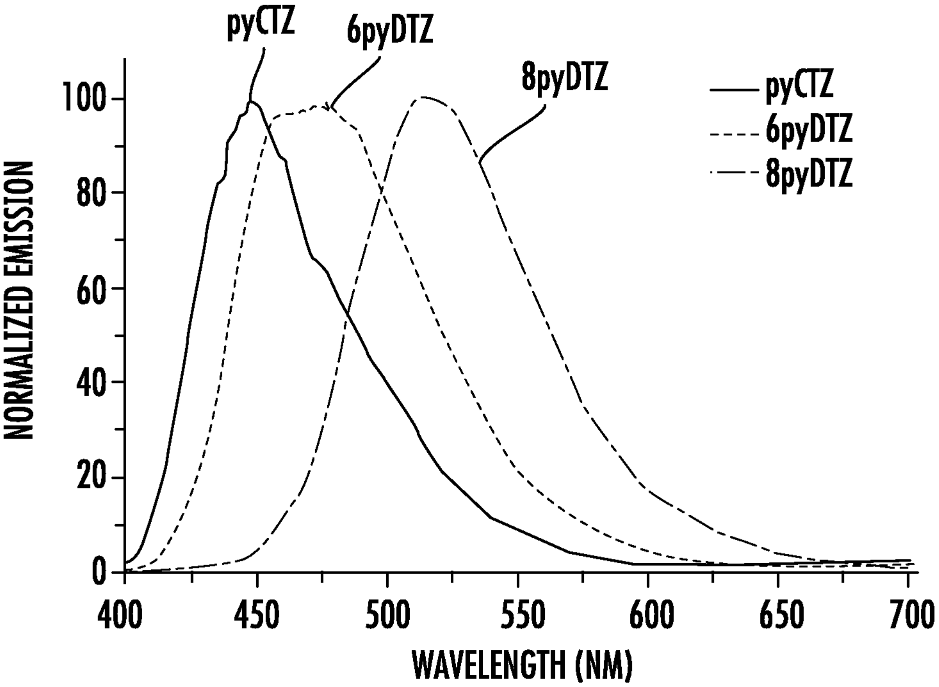

LumiLuc has broad substrate specificity. It improved the photon flux of 3a (pyCTZ) and 3d (6pyDTZ) from teLuc by about 120% and about 150%, respectively (FIG. 4C). The directed evolution process to enhance photon flux of teLuc for 8pyDTZ did not preclude the luciferase from catalyzing other structurally relevant substrates. LumiLuc is capable of efficiently generating blue, teal, or yellow bioluminescence when paired with pyCTZ, 6pyDTZ or 8pyDTZ (λmax: 450, 476, and 525 nm, respectively; FIG. 4D), thereby leading to a new family of ATP-independent bioluminescent reporters with water-soluble substrates.

Example 3

LumiLuc-8pyDTZ in Cultured Mammalian Cells

Figure 7:
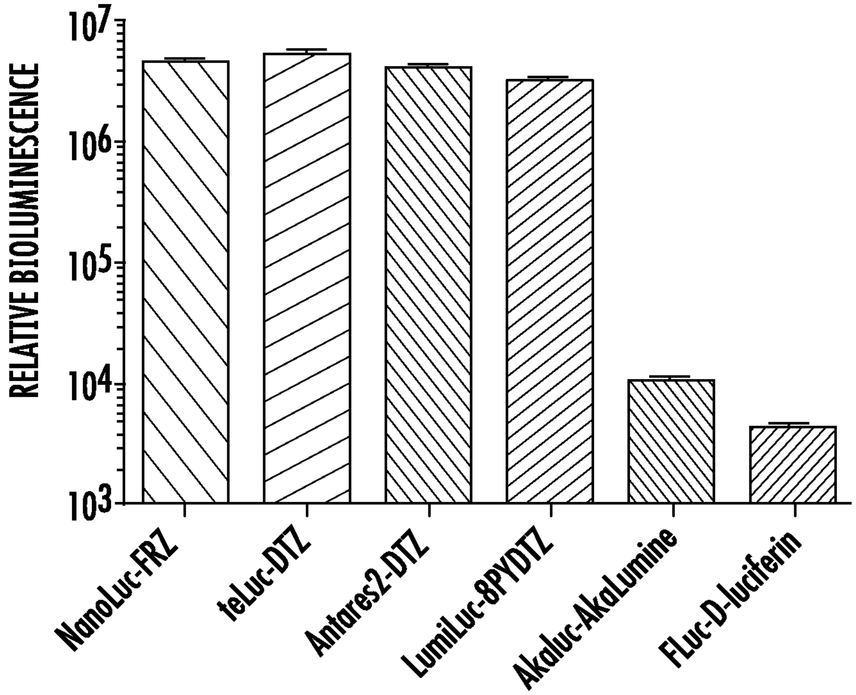
FIG. 7 shows the comparison of luciferase-luciferin pairs in live mammalian cells. Measurements were performed with 5000 HEK 293T cells in PBS. Luciferase genes were introduced by transient transfection (about 70% transfection efficiency). Final concentrations for FRZ, DTZ, and 8pyDTZ were 20 μM, and final concentrations for AkaLumine and D-luciferin were 100 μM. Signals were integrated over the first 10 min post injection of substrates. Data are presented as mean and s.d. from three independent measurements. Under this condition, LumiLuc-8pyDTZ produced about 300-fold higher photon flux than Akaluc-AkaLumine.
Figure 8A:
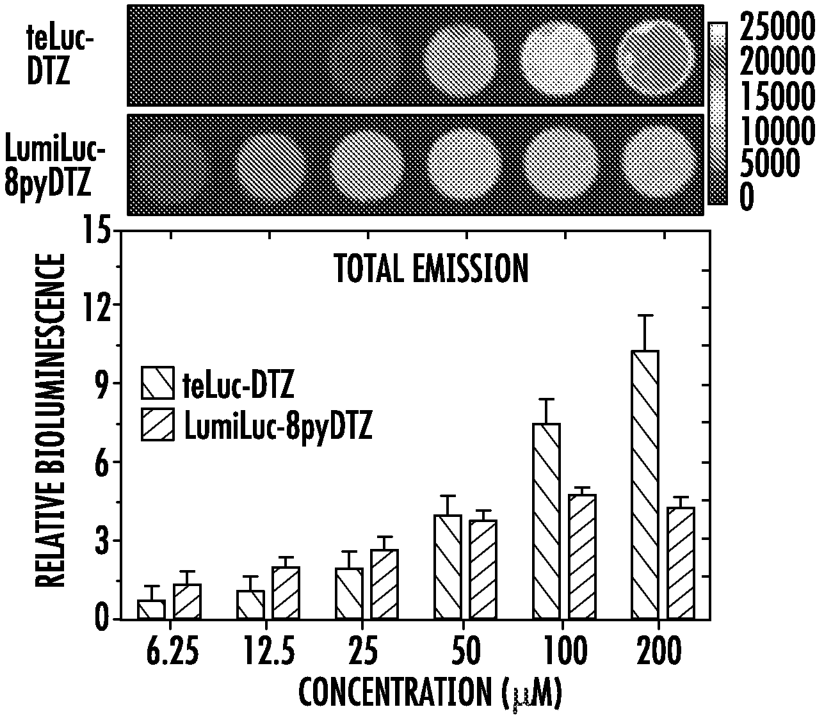
FIGS. 8A and 8B show the bioluminescence of teLuc- and LumiLuc-expressing HEK 293T cells. Images were acquired (FIG. 8A) without or (FIG. 8B) with a 600-700 nm bandpass filter. Values for relative brightness were normalized to teLuc in the presence of 6.25 μM DTZ.
Figure 8B:
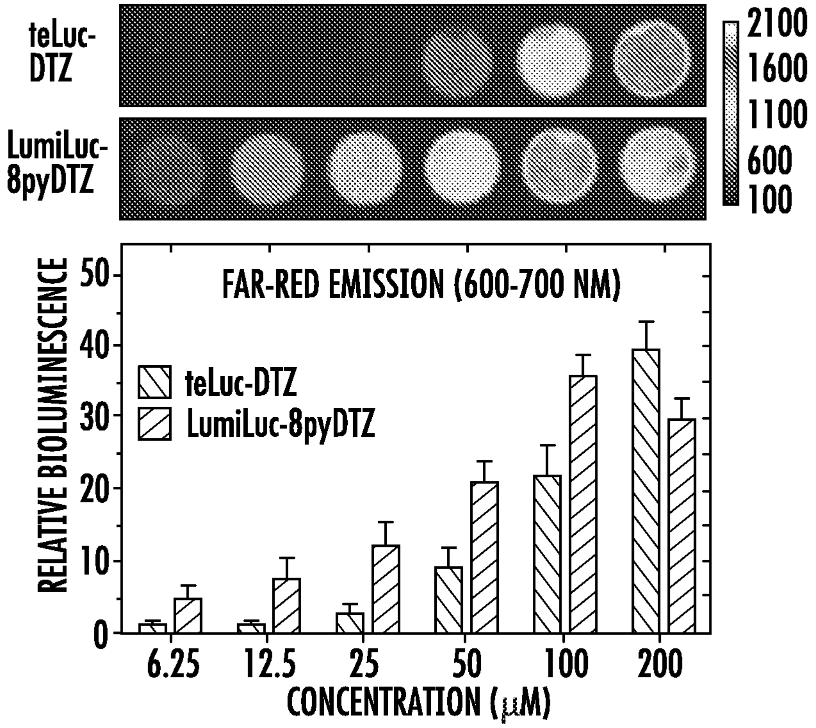

Next, LumiLuc-8pyDTZ was evaluated in human embryonic kidney (HEK) 293T cells transiently expressing the luciferase (FIG. 7). The LumiLuc-8pyDTZ pair produced about 3- to 5-fold more bioluminescence than teLuc-8pyDTZ at all tested substrate concentrations. Moreover, despite that LumiLuc-8pyDTZ is less bright than teLuc-DTZ at saturated substrate concentrations, LumiLuc-8pyDTZ is notably brighter than teLuc-DTZ at low substrate concentrations (from 6.25 to 25 μM; FIG. 8A). Far-red emission at wavelengths longer than 600 nm is more indicative of the in vivo performance of bioluminescent reporters, because mammalian tissue is more transparent in this spectral region.[25] To compare far-red emission intensities of bioluminescent reporters, HEK 293T cells were imaged in the presence of a 600-700 nm bandpass filter. At substrate concentrations from 6.25 to 100 μM, LumiLuc-8pyDTZ consistently produces 1.6- to 3.9-fold higher photon flux than teLuc-DTZ (FIG. 8B).

ATP-dependent luciferases, such as FLuc and Akaluc consumes one ATP molecule in each catalytic cycle, leading to metabolic disruption.[8] Instead, ATP-independent LumiLuc does not use ATP for catalysis. ATP/ADP ratios were monitored in live HEK 293T cells using PercevalHR, a previously reported fluorescent ATP/ADP biosensor.[27] No ATP perturbation was observed from 8pyDTZ-treated, LumiLuc-expressing cells.

Example 4

LumiLuc-8pyDTZ to Track Tumor Growth in a Mouse Xenograft Model

Figure 9A:
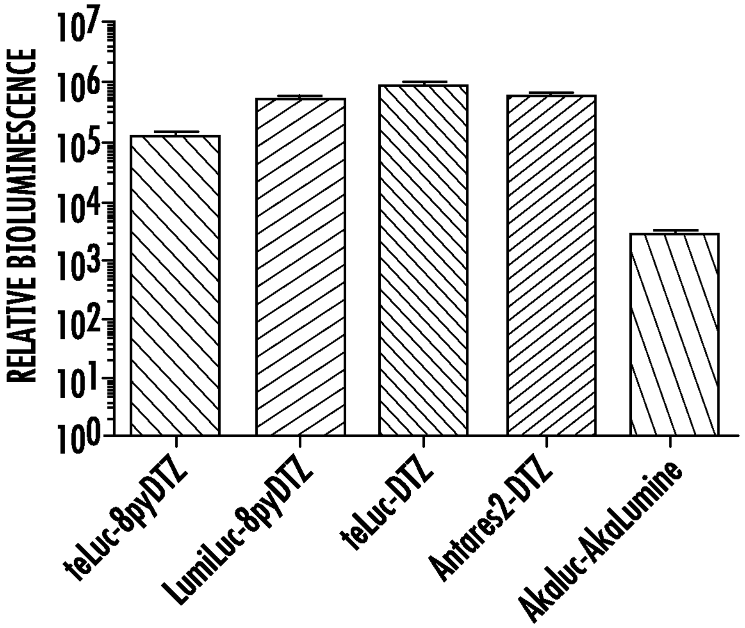
FIGS. 9A and 9B show bioluminescence characterizations of HeLa cells stably expressing luciferases.
Figure 9B:
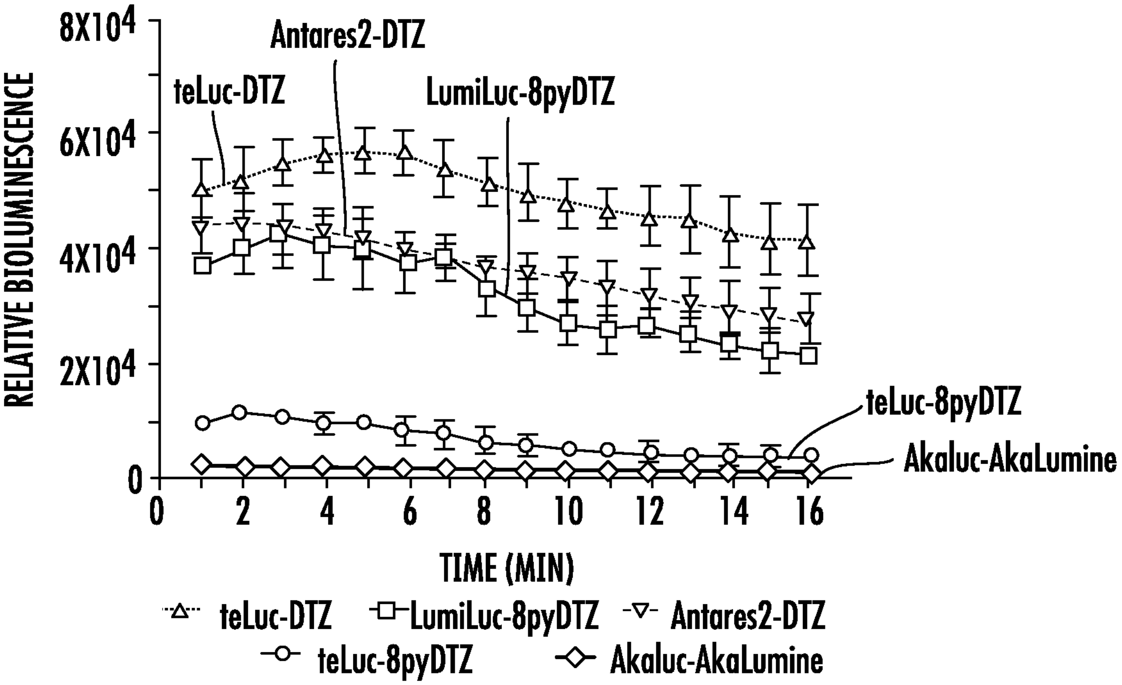
Figure 10A:
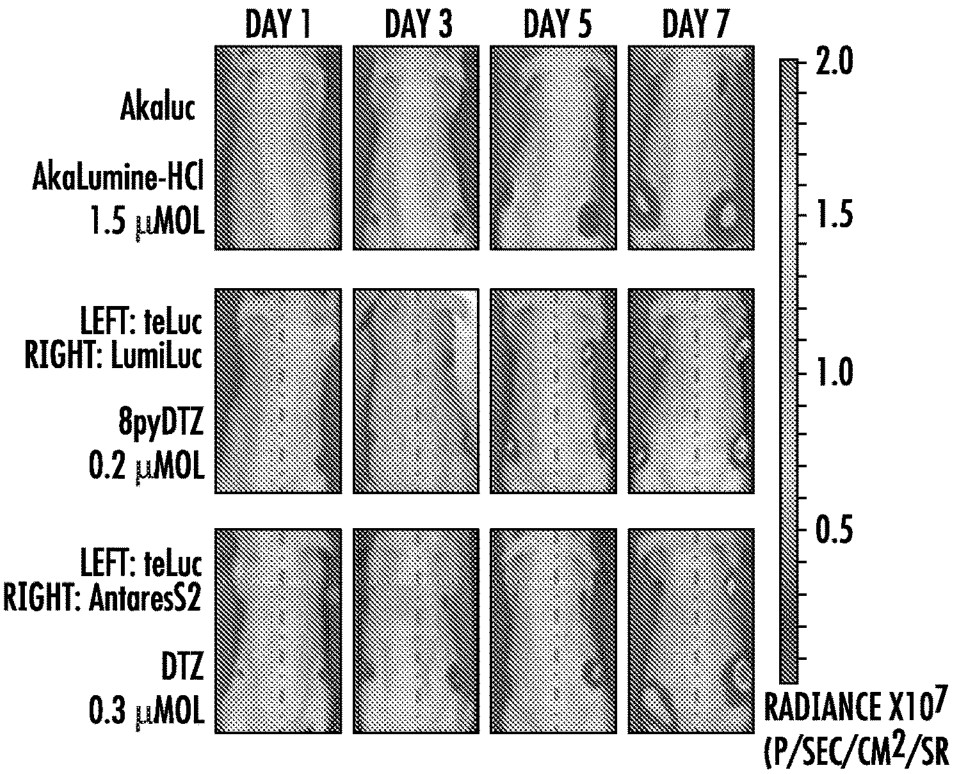
FIGS. 10A and 10B show the tracking of tumor growth in a xenograft mouse model with various luciferase-luciferin pairs.
Figure 10B:
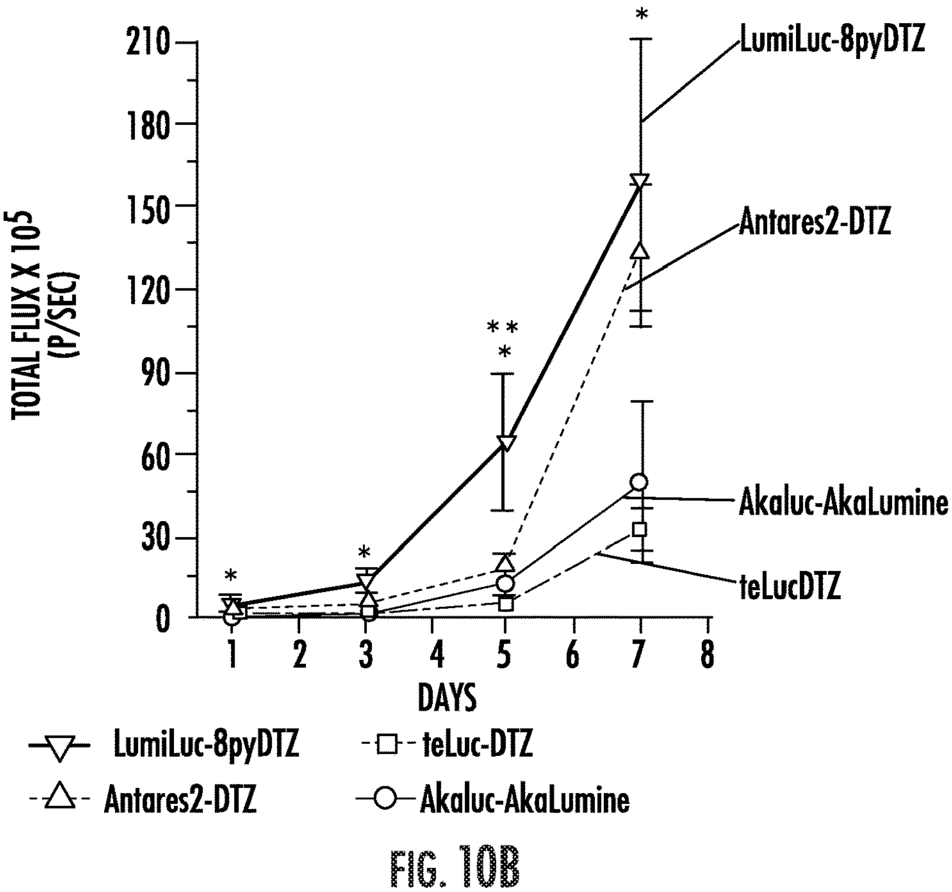

BLI has been a popular imaging modality for various animal models.[13, 25] The recently reported Akaluc-AkaLumine and Antares2-DTZ pairs are two benchmark reporters for in vivo BLI.[6, 7] A biologically-relevant tumor xenograft mouse model[28] was adapted to compare these bioluminescent reporters. Cervical cancer HeLa cell lines stably expressing individual luciferases were generated, including teLuc, Antares2, LumiLuc, and Akaluc (FIGS. 9A and 9B). Next, 104 or 105 luciferase-expressing HeLa cells were injected into the left or right dorsolateral trapezius and thoracolumbar regions of immunodeficient NU/J mice (day 0) and monitored tumor growth over 4 weeks. Bioluminescence was quantified in days 1, 3, 5, 7, 14, and 28 after tail vein injection of corresponding substrates. AkaLumine-HCl was delivered at a dose of 1.5 μmol per mouse. This dosage (about 75 nmol/g), which is normalized against the body weights of mice, is identical to the previously reported dosage.[6] Moreover, when 3 μmol of AkaLumine-HCl per mouse (about 150 nmol/g) was used, death for 2 out of 3 mice was observed in the pilot experiment. 8pyDTZ was dissolved in normal saline to its saturation concentration and intravenously injected, resulting in a dose of 0.2 μmol per mouse (about 10 nmol/g). The LumiLuc-8pyDTZ pair showed detectable bioluminescence on day 1 at sites inoculated with 104 cells, and kept exhibiting about 3-fold higher photon flux over Akaluc-AkaLumine up to day 7 (FIGS. 10A and 10B). The signals for Akaluc-AkaLumine at sites inoculated 104 cells were not consistently higher than background until day 3. Furthermore, the in vivo brightness of LumiLuc-8pyDTZ is comparable to, if not higher than, the Antares2-DTZ pair (FIGS. 10A, 10B and 11A-11C), despite the fact that the majority of emitted photons from LumiLuc-8pyDTZ has not yet exceeded 600 nm. These data collectively support that LumiLuc-8pyDTZ is a superior bioluminescent reporter system for high-sensitivity in vivo BLI.

Figure 11A:
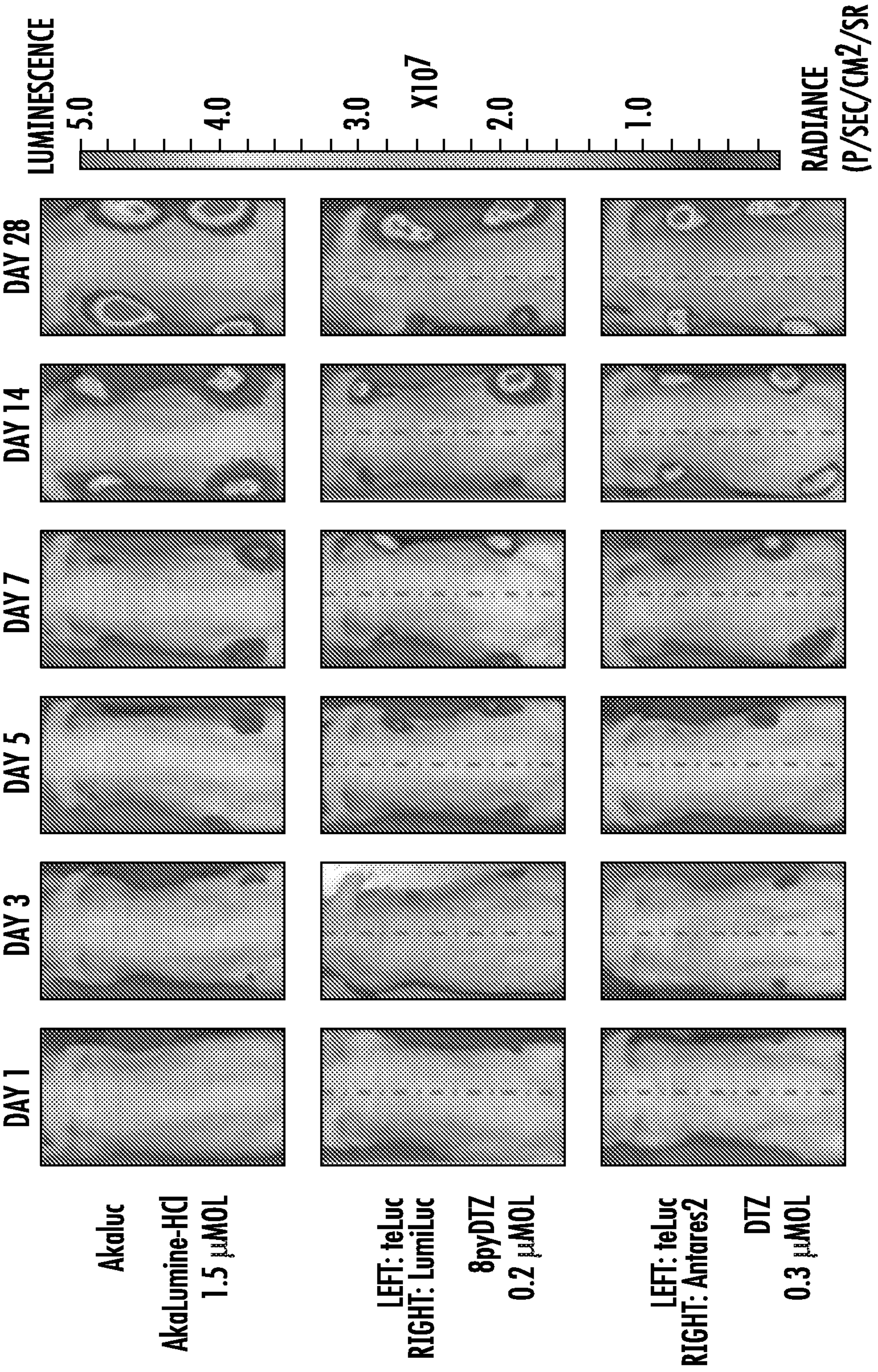
FIGS. 11A-11C show tracking of tumor growth in a xenograft mouse model with various luciferase-luciferin pairs.
Figure 11B:
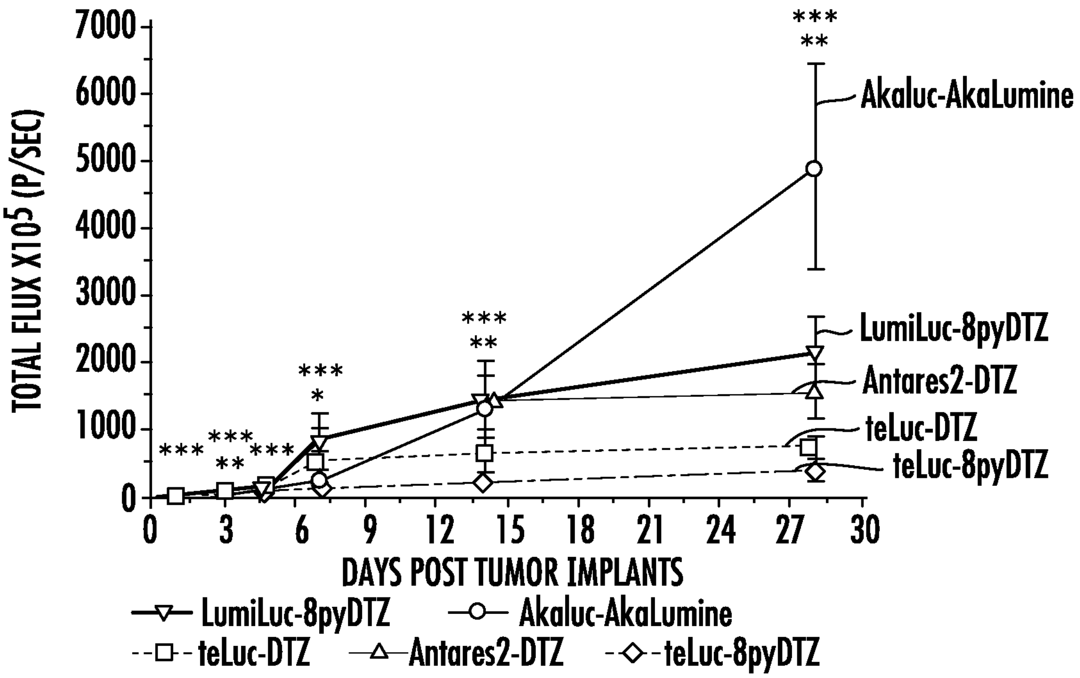
Figure 11C:
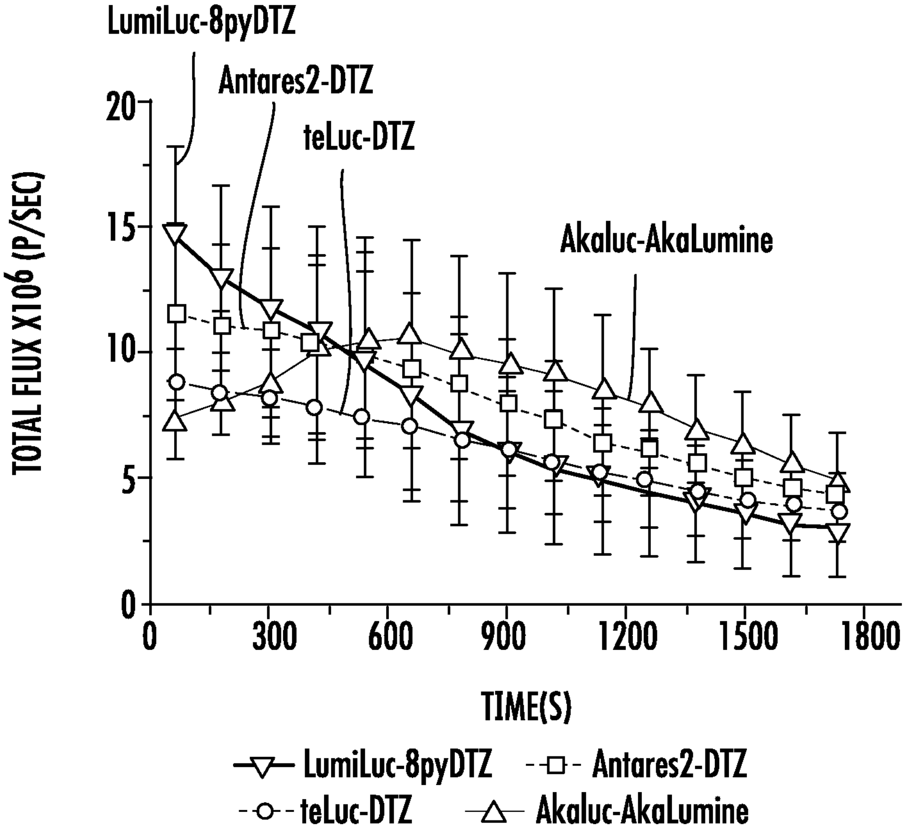

The bioluminescence of Akaluc-AkaLumine eventually surpassed LumiLuc-8pyDTZ from day 14 (FIGS. 11A-11C). In addition to differences in biodistribution and pharmacokinetic properties of AkaLumine and 8pyDTZ, it was interpret that 8pyDTZ may be a limiting reagent in large tumors because AkaLumine-HCl could be delivered into mice at a much higher dose than 8pyDTZ due to the higher solubility of AkaLumine-HCl. It may be possible further enhance the in vivo performance of marine luciferases and their derivatives by further increasing the water solubility and thus the administration dosage of CTZ and DTZ analogs.

This data provides for the monitoring of the disclosed luciferase-luciferin pairs for in vivo monitoring of tumor models. For example, bioluminescence can be monitored in a tumor model by establishing a luciferase expressing cell (e.g. a cell expressing LumiLuc, teLuc, RLuc8 and OpyLuc) in the model, e.g. by transfecting cells in the model and/or by administering to that model already transfected cells expressing a luciferase, and administering to the model a luciferin (e.g. pyCTZ, pyOHCTZ, pyOMeCTZ, pyOEtCTZ, pyiPrCTZ, 2pyDTZ, 6pyDTZ, 6opyDTZ or 8pyDTZ). Using these luciferase-luciferin pairs as reporter systems the bioluminescence can be used as a tool to monitor the tumor.

Example 5

Figures 12A, 12B:
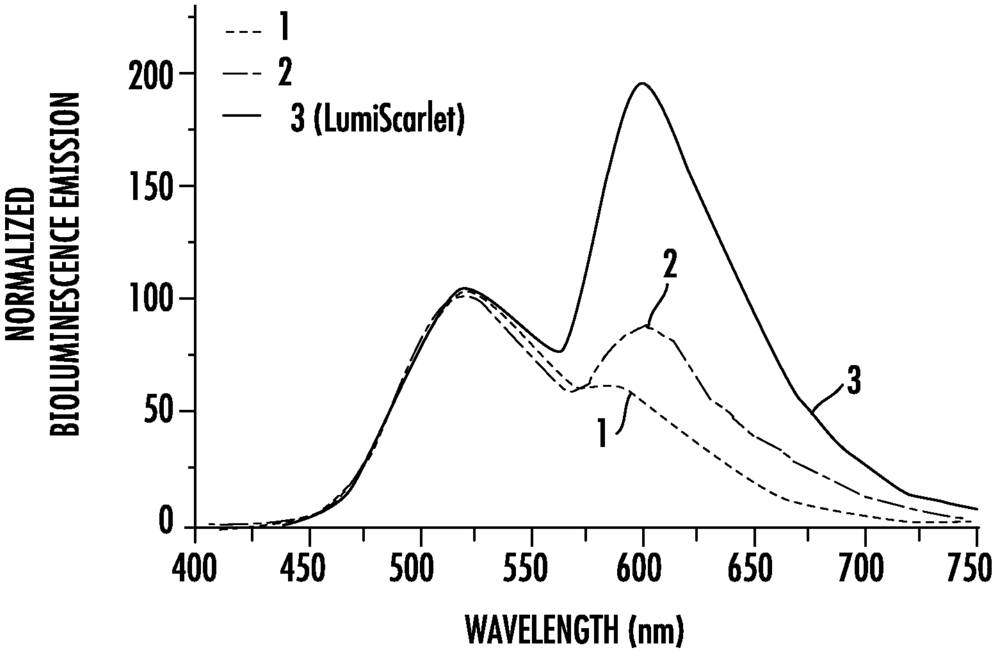
FIGS. 12A-12F show the engineering and characterization of BRET-based LumiScarlet and teScarlet.
Figure 13A:
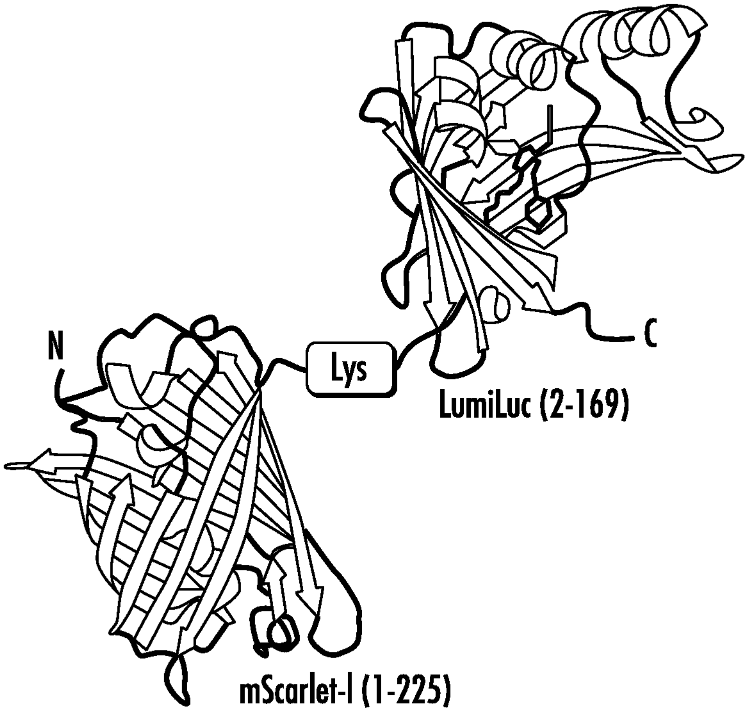
FIGS. 13A-13D show BRET-based LumiScarlet for deep tissue BLI.

Engineering of BRET-Based LumiScarlet and teScarlet for Deep-Tissue BLI mScarlet-I is a recently reported red fluorescent protein with high quantum yield and excellent performance as a Förster resonance energy transfer (FRET) acceptor.[29] It was thus hypothesized that LumiLuc could be genetically fused to mScarlet-I for BRET, thereby red-shifting the emission of LumiLuc. Several fusion strategies between LumiLuc and mScarlet-I were explored, libraries were constructed by randomizing the linkers, and mutants with high BRET efficiency were screened (FIGS. 12A and 12B). A mutant was identified, namely LumiScarlet (FIG. 13A), which is a fusion protein of mScarlet-I (residues 1-225; Bindels et al, 2016, Nature Methods, 14(1), 53-56; incorporated herein by reference) linked to the N-terminus of LumiLuc (residues 2-169; SEQ ID NO. 3) through a single-residue "Lys" linker (nucleotide and polypeptide sequences provided herein as SEQ ID NOs. 4 and 5, respectively).

Figure 12C:
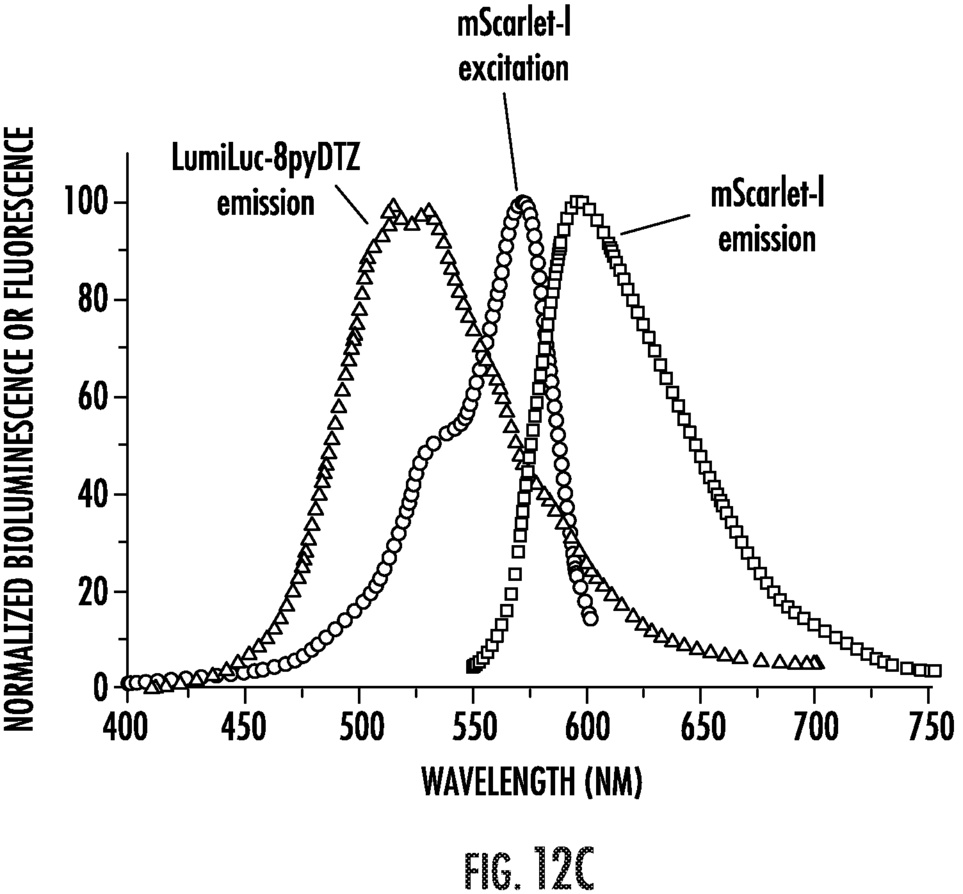
Figure 13B:
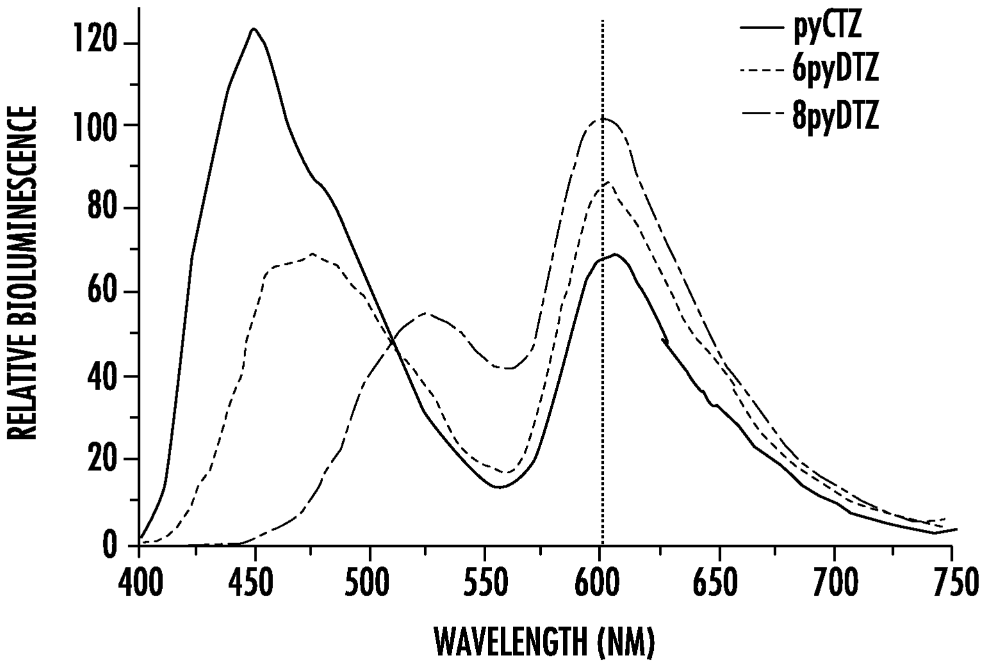

High BRET efficiency was achieved with LumiScarlet in the presence of either pyCTZ, or 6pyDTZ, or 8pyDTZ (FIG. 13B). In particular, because the emission spectrum of LumiLuc-8pyDTZ overlaps well with the excitation spectrum of mScarlet-I (FIG. 12C), about 510% of the total emission of LumiScarlet, when paired with 8pyDTZ, was longer than 600 nm (Table 3).

TABLE 3

BRET-based bioluminescent reporters that are based on NanoLuc and its derivatives.

| BRET Construct | BRET Donor | BRET Acceptor | Size (kDa) | $\lambda_{max}$ (nm) | Luciferin | Photon > 600 nm (%) | Ref. |
|---|---|---|---|---|---|---|---|
| Lumi Scarlet | LumiLuc | mScarlet-I | 44 | 527, 600 | 8pyDTZ | 51 | This work |
| | LumiLuc | mScarlet-I | 44 | 476, 600 | 6pyDTZ | 38 | |
| | LumiLuc | mScarlet-I | 44 | 450, 600 | pyCTZ | 26 | |
| Antares | NanoLuc | CyOFP | 70 | 456, 583 | FRZ | 23 | ([1]) |
| Antares2 | teLuc | CyOFP | 70 | 501, 583 | DTZ | 33 | ([2]) |
| ReNL | NanoLuc | tdTomato | 72 | 459, 583 | FRZ | 24 | ([3]) |

Figure 12D:
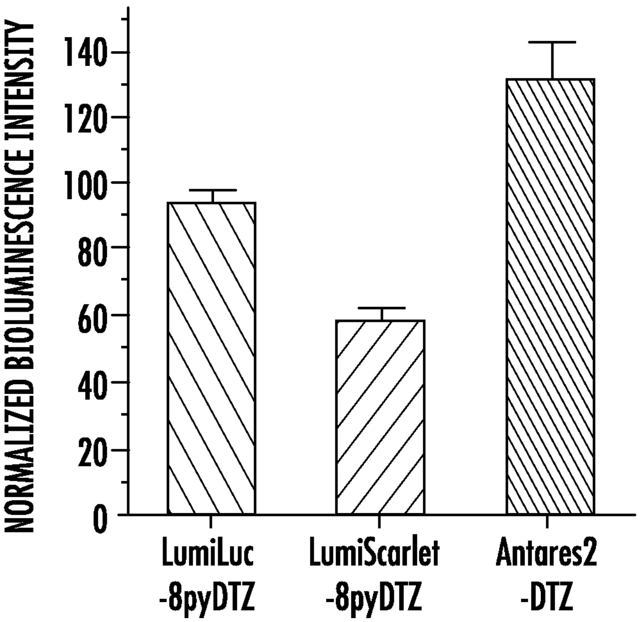
Figure 13C:
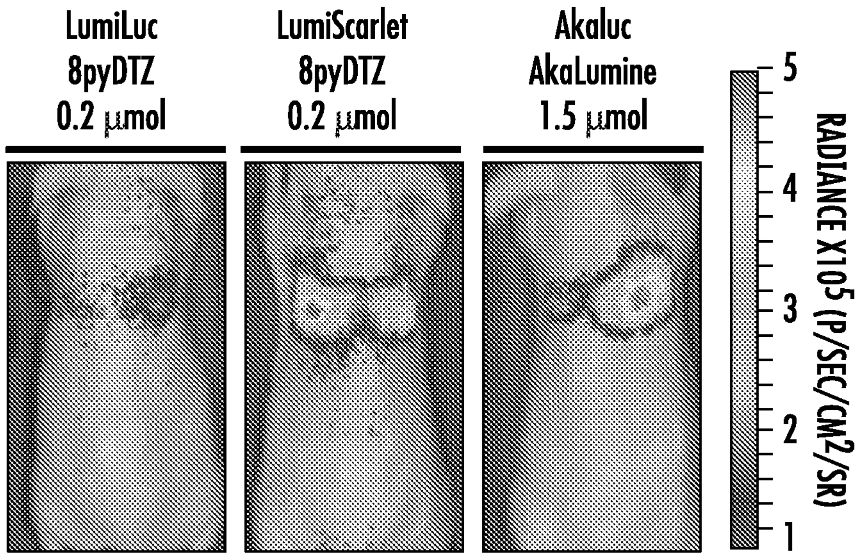
Figure 13D:
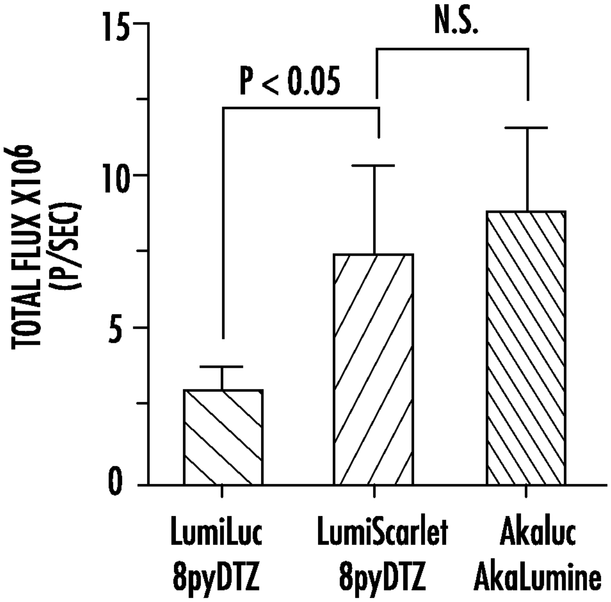

Next, the newly engineered LumiLuc-8pyDTZ and LumiScarlet-8pyDTZ were compared with Akaluc-AkaLumine for deep-tissue BLI. A million HeLa cells stably expressing corresponding luciferases were injected into each of NU/J mice via tail vein and performed BL imaging 4 h later. Immunodeficient mice were used here to minimize immune responses to HeLa cells, so that signals will be mostly from live cells trapped in the lungs. LumiScarlet gave about 3-fold higher detectable signals than LumiLuc under this condition (FIGS. 13C and 13D), even though the in vitro brightness of LumiScarlet is only about 70% of LumiLuc (FIG. 12D). Moreover, the signals from LumiScarlet-8pyDTZ were comparable to the signals from Akaluc-AkaLumine.

Of note, some diffuse signals were observed from areas other than the lungs. These signals were not caused by substrate background, as injection of 8pyDTZ into blank mice resulted in only weak background much lower than what was observed in FIG. 13C. Luciferase activities were detectable in blood after tail vein injection of luciferase-expressing HeLa cells, suggesting partial lysis of luciferase-labeled cells during cell injection. Also, in contrast to ATP-independent LumiLuc and LumiScarlet, ATP-dependent Akaluc is enzymatically inactive in serum because of relatively low ATP levels and further deactivation by serum components.[8] Thus, diffuse signals from LumiScarlet in FIG. 13C were likely from the LumiScarlet luciferase released into blood.

Collectively, the deep-tissue BLI results confirm that red-shifted BRET-based LumiScarlet has better mammalian tissue penetration than LumiLuc. Moreover, LumiScarlet-8pyDTZ is a novel, ATP-independent bioluminescent reporter with exceptional deep-tissue BLI performance comparable to ATP-dependent Akaluc-AkaLumine.

Figure 12E:
Figure 12F:
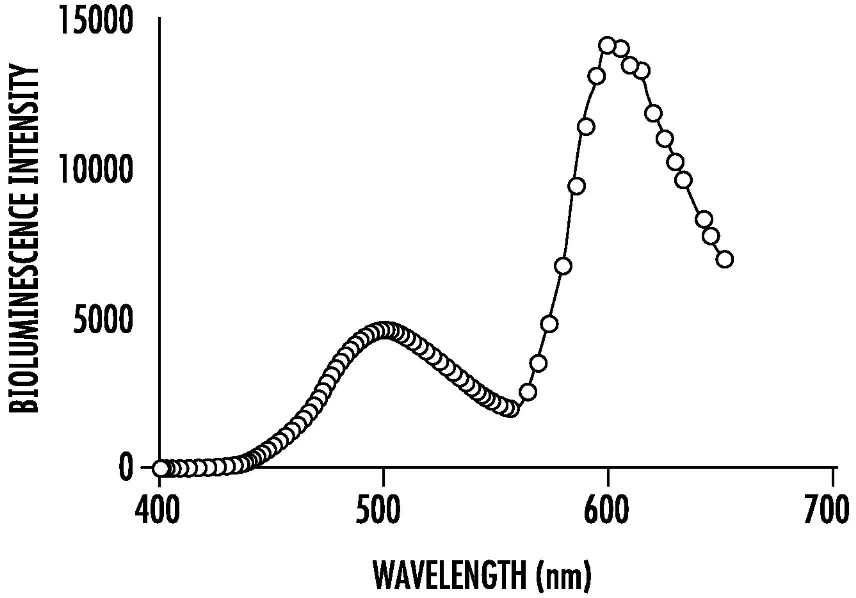

Similar to the BRET-based strategy of creating LumiScarlet, a BRET-based fusion of teLuc and mScarlet-I was engineered. Libraries were constructed to randomize the linker between teLuc and mScarlet-I. A mutant was identified, namely teScarlet (FIG. 12E), which is a fusion protein of mScarlet-I (residues 1-221) linked to the N-terminus of teLuc (residues 2-169) through a three-residue "His-Leu-Asp" linker (nucleotide and polypeptide sequences provided herein as SEQ ID NOs. 7 and 8, respectively). High BRET efficiency was also achieved with teScarlet in the presence of DTZ (FIG. 12F).

Discussion of Examples 1-5

Conventionally, ATP-dependent bioluminescent reporters, such as FLuc and Akaluc, are considered to be more useful for in vivo BLI than ATP-independent marine luciferases, because the emission of ATP-dependent insect luciferases is often at the red end of the visible spectrum where the mammalian tissue is relatively transparent. However, these insect luciferases require ATP and Mg2+ for bioluminescence. The ATP- and Mg2+-dependency is sometimes problematic because ATP and Mg2+ levels may vary under different biological circumstances.[30] In particular, ATP-dependent luciferases are inactive in extracellular space and common biological fluids such as blood and urine, where ATP accessibility is limited.[8] Moreover, ATP-dependent luciferases consume ATP in bioluminescence reactions and may cause concerns such as metabolic disruption.[8] In contrast, most ATP-independent marine luciferases are enzymatically active in extracellular space and common biological fluids; they do not consume ATP for bioluminescence. Furthermore, some marine luciferase derivatives have fast catalytic turnover and thus give high photon flux. It is therefore not surprising that marine luciferase and their derivatives, such as NanoLuc and Gaussia luciferase, have been widely used for in vitro bioluminescence assays. However, currently, the in vivo applications of marine luciferases are hindered by their blue emission and poor substrate water solubility. As disclosed herein, combined chemical synthesis and protein engineering approaches yielded enhanced ATP-independent marine luciferases for in vivo BLI by developing red-shifted colors and water-soluble substrates.

First, a series of pyridyl CTZ and DTZ analogs with diverse emission profiles were prepared. The water solubility of these synthetic analogs generally increased by about 10-fold from their ancestors. These substrate analogs can not only be paired with the new luciferases engineered here, but also existing ATP-independent reporters, such as RLuc and aequorin.

Further, a luciferase was engineered for the 8pyDTZ substrate via directed protein evolution. The resultant LumiLuc-8pyDTZ bioluminescent reporter system exhibited reduced KM and red-shifted emission. These factors favored in vivo BLI. As a result, LumiLuc-8pyDTZ showed high sensitivity in a mouse xenograft model. In addition, LumiLuc-8pyDTZ did not perturb the intracellular ATP/ADP level, and 8pyDTZ could be dissolved up to about 2 mM in low-viscosity saline without using irritative and toxic organic cosolvent. Therefore, the efforts disclosed herein enhanced not only the biocompatibility of bioluminescent reporters, but also reproducibility for intravenous injections.

Furthermore, a BRET-based LumiScarlet reporter was developed for further red-shifted emission. The emission of LumiLuc-8pyDTZ overlaps well with the excitation of mScarlet-I, an excellent red-emitting resonance energy transfer acceptor. LumiScarlet-8pyDTZ exhibited high brightness, significant emission longer than 600 nm, and excellent tissue penetration. LumiScarlet-8pyDTZ was comparable to NIR-emitting Akaluc-AkaLumine in a mouse model for deep-tissue BLI. Moreover, because LumiScarlet is enzymatically active in blood, it will be an excellent reporter for monitoring targets of interest in the blood of in vivo models.

LumiLuc is a luciferase with broad substrate specificity. When it was paired with different substrates, intense blue, teal, and yellow bioluminescence was generated. Subsequently, different emission profiles from LumiScarlet were gained in the presence of different substrates. The use of LumiScarlet-8pyDTZ for deep-tissue imaging was also demonstrated. In addition, because the two emission peaks of LumiScarlet-pyCTZ or LumiScarlet-6pyDTZ are more separated than LumiScarlet-8pyDTZ, LumiScarlet-pyCTZ and LumiScarlet-6pyDTZ will be useful for studying protein-protein interactions or constructing BRET-based biosensors.

In summary, disclosed herein are several engineered luciferase-luciferin pairs that emit photons spanning an appreciable range in the visible spectrum. The discoveries disclosed herein greatly enhance the biocompatibility and sensitivity of ATP-independent bioluminescent reporters for in vivo BLI. Future studies are likely to continuously increase the water-solubility of CTZ and DTZ analogs and red-shift the emission of marine luciferases. Subsequently, it is expected that a large array of bioluminescent biosensors will be developed on the basis of these bright, ATP-independent bioluminescent reporters.[31] The new reporters and biosensors will further ease non-invasive imaging of freely moving animals, leading to new biological insights.

Materials and Methods for Examples 6-9

Materials and General Methods

Synthetic DNA oligonucleotides were purchased from Integrated DNA Technologies. Restriction endonucleases were purchased from Thermo Fisher Scientific. Q5 high-fidelity DNA polymerase and Taq DNA polymerase were purchased from NEB. Products of PCR and restriction digestion were purified by gel electrophoresis and Syd Laboratories Gel Extraction columns. Plasmid DNA was purified using Syd Laboratories Miniprep columns. DNA sequences were analyzed by Eurofins. AkaLumine-HCl was purchased from Aobious. All other chemicals were purchased from Sigma-Aldrich, Fisher Scientific, or VWR and used without further purification. Bruker Avance DRX 600 and Varian NMRS 600 at the UVA Biomolecular Magnetic Resonance Facility was used to record all NMR spectra. Chemical shift (δ) is given in parts per million relative to $^1H$ (7.24 p.p.m.) and $^{13}C$ (77.23 p.p.m.) for $CDCl_3$; $^1H$ (2.50 p.p.m.) and $^{13}C$ (39.5 p.p.m.) for DMSO-$d_6$; $^1H$ (3.31 p.p.m.) and $^{13}C$ (49.15 p.p.m.) for methanol-$d_4$. Splitting patterns are reported as s (singlet), bs (broad singlet), d (doublet), t (triplet), dd (doublet of doublets), and m (multiplet). Coupling constant (J) is given in Hz. High resolution ESI-MS was run on an Agilent 6545 Q-TOF LC/MS system by direct infusion. A Waters Delta Prep ZQ 2000 LC-MS Purification System equipped with a XBridge BEH Amide OBD Prep Column (130 Å, 5 μm, 30 mm×150 mm) was used for preparative reverse-phase HPLC purifications. Images were analyzed using the Fiji image analysis software. Microsoft Excel and GraphPad Prism were used to analyze data and prepare figures.

Chemical Synthesis 3-benzyl-5-(4-methoxyphenyl)pyrazin-2-amine (2)

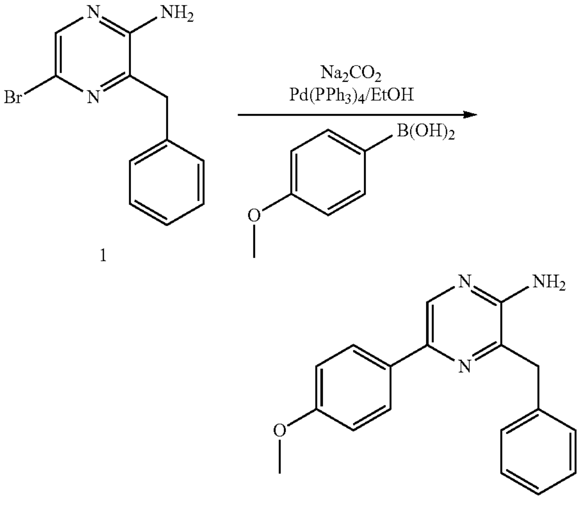

1

2

1 was prepared following the published synthesis methods[64]. To a solution of $Pd(PPh_3)_4$ (230 mg, 0.2 mmol, 0.1 equiv.) in 50 mL EtOH was added 1 (528 mg, 2 mmol, 1 equiv.), 1N $Na_2CO_3$ solution (4 mL, 4 mmol, 2 equiv.) and 4-Methoxylphenylboronic acid (304 mg, 2 mmol, 1 equiv.). The resultant mixture was stirred at 80° C. under argon for 12 h. The solvent was removed in vacuo and the residue was suspended in 100 mL dd$H_2O$, which was extracted twice with EtOAc (100 mL). The organic layers were combined and dried over anhydrous $Na_2SO_4$, filtered and removed in vacuo. The residue was purified by silica column chromatography with elution (Ethyl acatate:Hexane=1:1) to yield compound 2 as yellow solid (413 mg, 71%). $^1H$ NMR (600 MHz, DMSO-$d_6$) δ 8.33 (s, 1H), 7.82 (d, J=8.8 Hz, 2H), 7.32 (d, J=6.7 Hz, 2H), 7.26 (t, J=7.6 Hz, 2H), 7.17 (t, J=7.4 Hz, 1H), 6.95 (d, J=8.8 Hz, 2H), 6.26 (s, 2H), 4.05 (s, 2H), 3.76 (s, 3H). $^{13}C$ NMR (150 MHz, DMSO-$d_6$) 158.9, 152.2, 139.8, 139.0, 138.2, 136.2, 128.9, 128.2, 126.1, 126.1, 114.1, 55.1, 38.6. HRMS (ESI-TOF) calcd for $C_{18}H_{17}N_3O$ $[M+H]^+$: 292.1372, found: m/z 292.1369.

8-benzyl-6-(4-methoxyphenyl)-2-(pyridin-4-ylmethyl)imidazo[1,2-a]pyrazin-3(7H)-one (pyOMeCTZ)

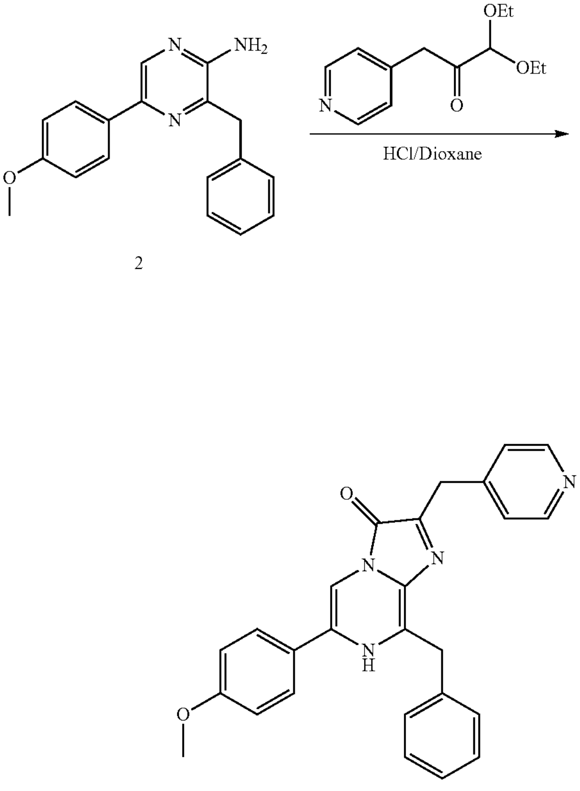

2 pyOMeCTZ

To a solution of 2 (29 mg, 0.1 mmol, 1 equiv.) and 3-pyridin-4-yl-1,1-diethoxyacetone (45 mg, 0.2 mmol, 2 equiv) in 2 mL degassed 1,4-dioxane was added 1 mL 6N HCl. The resulting mixture was stirred at 80° C. in a seal tube for 12 h. The solvent was then removed in vacuo and the residue was dissolved in 1 mL (ACN:$H_2O$=1:1) and next purified with preparative RP-HPLC. (acetonitrile/water=1:99 to 90:10, 20 mL/min, UV 254 nm). Product fractions were combined and lyophilized to give pyOMeCTZ as yellow powder (10 mg, 24%), which has to be stored as solid at −80° C. for long-term stability. $^1H$ NMR (600 MHz, Methanol-$d_4$) δ 8.82 (d, J=6.4 Hz, 2H), 8.27 (s, 1H), 8.09 (d, J=6.2 Hz, 2H), 7.73 (d, J=8.7 Hz, 2H), 7.43 (d, J=7.5 Hz, 2H), 7.32 (t, J=7.6 Hz, 2H), 7.26 (t, J=7.2 Hz, 1H), 7.10 (d, J=8.7 Hz, 2H), 4.66 (s, 2H), 4.61 (s, 2H), 3.87 (s, 3H). $^{13}C$ NMR (150 MHz, Methanol-$d_4$) δ 142.7, 137.0, 130.2, 130.1, 129.1, 128.7, 126.5, 115.9, 56.2. HRMS (ESI-TOF) calcd for $C_{26}H_{22}N_4O_2$ $[M+H]^+$: 423.1743, found: m/z 423.1740.

2-benzyl-6-phenyl-8-(pyridin-4-yl)imidazo[1,2-a]pyrazin-3(7H)-one (pyDTZ)

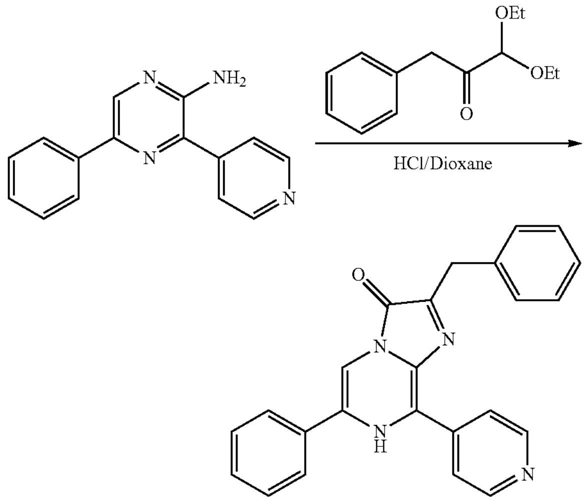

pyDTZ

To a solution of 5-phenyl-3-(pyridin-4-yl)pyrazin-2-amine (25 mg, 0.1 mmol, 1 equiv.) and 1,1-diethoxy-3-phenylpropan-2-one (89 mg, 0.4 mmol, 4 equiv.) in 5 mL degassed 1,4-dioxane was added 0.8 mL 6 N HCl, and the resulting mixture was stirred at 80° C. in a sealed tube for 12 h. The solvent was then removed in vacuo and the residue was dissolved in 1 mL (ACN:$H_2O$=1:1) and next purified with preparative RP-HPLC. (acetonitrile/water=1:99 to 90:10, 20 mL/min, UV 254 nm). Product fractions were combined and lyophilized to give pyDTZ as brown powder (8 mg, 22%). $^1H$ NMR (600 MHz, Acetonitrile-$d_3$ and D20, ratio=9:1) δ 9.31 (d, J=6.8 Hz, 2H), 8.84 (d, J=6.8 Hz, 2H), 8.54 (s, 1H), 8.09 (d, J=8.0 Hz, 2H), 7.52 (t, J=7.6 Hz, 2H), 7.44 (t, J=7.3 Hz, 1H), 7.35 (d, J=7.7 Hz, 2H), 7.28 (t, J=7.7 Hz, 2H), 7.24-7.21 (m, 1H), 4.19 (s, 2H). $^{13}C$ NMR (150 MHz, Methanol-$d_4$) δ 143.0, 140.7, 140.1, 139.5, 137.5, 132.0, 130.2, 129.9, 129.6, 129.4, 127.8, 127.5, 127.4, 126.5, 113.8, 33.6. HRMS (ESI-TOF) calcd for $C_{24}H_{18}N_4O$ $[M+H]^+$: 379.1481, found: m/z 379.1477.

Plasmid Construction

Polymerase chain reactions with various synthetic oligonucleotide pairs (see Table 4) were used to amplify genetic elements. Generating gene libraries with randomizations were previously described. Abovementioned screening approach was applied to the selection process of random mutagenesis by Error prone-PCR. Oligonucleotides pBAD-F and pBAD-R were used to create a library with randomization by using Taq DNA polymerase, 0.2 mM $MnCl_2$, and unbalanced dNTPs to promote amplification errors. The PCR product was digested with Xho I and Hind III restriction enzymes and ligated into a predigested, compatible pBAD/His B plasmid. To create mammalian expression plasmids containing NFκB response element, NFkB_SacI_F and NFkB_BglII_R were used to amplify the fragment from pHAGE NFkB-TA-LUC-UBC-GFP-W plasmid (Addgene:49343), which was further treated with Sac I and Bgl II restriction enzymes and ligated into a predigested, compatible SRE reporter vector_559 plasmid (Addgene: 82686). For Antioxidant response element, the DNA fragment was synthesized by IDT and ligated into Sac I and Bgl II predigested SRE reporter vector 559 plasmid. The Opy-Luc, RLuc8, and Akaluc gene were cloned into corresponding plasmids containing desired response element by using opyluc_AscI_Kozak_F/opyluc_FseI_R, Rluc_AscI_Kozak_F/Rluc_FseI_R, or Akaluc_AscI_Kozak_F/Akaluc_FseI_R oligonucleotide pairs with Asc I and Fse I double digestion. All ligation products were used to transform *Escherichia coli* DH10B electrocompetent cells, which were next plated on LB agar plates supplemented with ampicillin (100 μg/mL).

TABLE 4

Oligonucleotides used in this study.

| Oligo name | SEQ ID NO. | Nucleotide sequence (5'>3') |
|---|---|---|
| pBAD-F | 19 | ATGCCATAGCATTTTTATCC |
| pBAD-R | 20 | GATTTAATCTGTATCAGG |
| NFkB_SacI_F | 21 | TACCGAGCTCATCCAGTTTGGACTAGTGG |
| NFkB_BglII_R | 22 | AGCCCAGATCTCCTCTAGAGTCTAGATCTGG |
| opyluc_AscI_ Kozak_F | 23 | AAAGCCACCGGCGCGCCGCCGCCACCATGGT CTTCACTCTCGAAGATTTTGT |
| opyluc_FseI_R | 24 | TCGAAGCGGCCGGCCTTACGCCAGAATGCGT TCATGCA |
| Akaluc_AscI_ Kozak_F | 25 | AAAGCCACCGGCGCGCCGCCGCCACCATGGA AGATGCCAAAAACATTAAGA |
| Akaluc_FseI_R | 26 | TCGAAGCGGCCGGCCTTACACGGCGATCTTG CCGTCCTTCTT |
| Rluc_ AscI_Kozak_F | 27 | AAAGCCACCGGCGCGCCGCCGCCACCATGGC TTCCAAGGTGTACGACC |
| Rluc_FseI_R | 28 | TCGAAGCGGCCGGCCTTACTGCTCGTTCTTC AGCACGCGCT |

Preparation of Mammalian Cell Culture and Cell Lysate

HEK 293T cells were cultured and transfected as previously described.[63] The number and density of cells in Dulbecco's phosphate-buffered saline (DPBS) were determined using a hemocytometer. Cells were next diluted in DPBS to gain the desired numbers in each 50 μL solution. Cell lysates were obtained by incubating desired number of cell in a CelLytic M solution for 15 minutes and centrifuged.

Library Screening

DH10B cells containing luciferase mutants were plated on LB agar plates supplemented with ampicillin (100 μg/mL) and 1-arabinose (0.02%, w/v %) and incubated at 37° C. overnight to form bacterial colonies. Agar plates were left at room temperature for another 6 h, and this was followed by bioluminescence imaging using a luminescence dark box (UVP Bio Spectrum) equipped with a QSI 628 cooled CCD camera (Quantum Scientific Imaging). Digital images were acquired after spraying about 200 μL of 50 μM pyDTZ to each agar plate, and next, images were processed with the Fiji image analysis software to derive bioluminescence intensities of individual colonies. For each round of selection, colonies showed bright bioluminescence were chosen and inoculated in 1 mL liquid LB broth containing ampicillin (100 μg/mL) and L-arabinose (0.02%, w/v %) in 96-well deep plates. After overnight growth at 37° C. and 250 r.p.m., the cultures were moved onto a shaker at room temperature for another 6 h. The 96-well plates were centrifuged and the pellet in each well was lysed with 200 μL B-PER. After 30-minute incubation, the 96-well plates were centrifuged again. Next, 2 μL lysate from each sample was transferred to the wells of new white 96-well plates where 100 μL of 20 μM pyDTZ in assay buffer was added to each well. Bioluminescence activities of individual samples were measured on a microplate reader. Kinetics were followed for 0.1 s signal integration every 30 s for a total of 10 min. Meanwhile, 2 μL lysate from each sample was added 100 μL of 20 μM pyOMeCTZ in assay buffer. The selectivity was determined by the specific activity toward pyDTZ/activity toward pyOMeCTZ. Top three mutants showing exceptionally high bioluminescence selectivity of pyDTZ over pyOMeCTZ were chosen for next-round selection, sequencing, and other additional characterization.

In Vitro Bioluminescence Characterization

Luciferases were expressed and purified as previously described.[53] A microplate reader was used for all in vitro bioluminescence characterizations. To record bioluminescence emission spectra, 50 μL of luciferin substrates was injected into the wells of white 96-well plates containing 50 μL of pure enzymes in PBS (1.5 mM ATP and 5 mM $MgSO_4$ were supplemented for Akaluc). Kinetic measurements were taken every 30 s post injection with 0.1 s integration and 10 s shaking during intervals. To derive values for apparent Michaelis constants (Km), substrate concentrations varied from 0.78 to 50 μM, and 10-min integrated bioluminescence at individual substrate concentrations were used to fit the Michaelis-Menten equation.

Bioluminescence Imaging with Luminescence Dark Box

UVP Bio Spectrum luminescence dark box was used for all bioluminescence imaging. To record bioluminescence imaging with pure enzymes, 50 μL of 60 μM substrates were injected into corresponding 50 μL pure enzymes (final concentration: 10 nM for RLuc8 and OpyLuc; 100 nM for Akaluc), and the bioluminescence imaging was collected with 10 s exposure time. A filter wheel equipped with a Chroma Blue 360-500 nm, a Chroma Green 495-580 nm, and a Chroma Red 600-700 nm filter was used to acquire emission in each channel. To use the luminescence dark box to directly image cells, we added luciferase-expressing HEK 293T cells (5,000 cells per well for RLuc8 and OpyLuc; 30,000 cells per well for Akaluc) and the indicated luciferin substrates solution were injected into wells of a white 96-well plate. Final concentration of each substrate were 25 μM for pyOMeCTZ, 10 μM for pyDTZ, and 100 μM for AkaLumine-HCl. Bioluminescence was imaged in the luminescence dark box immediately after substrate addition. The camera exposure time was set at 30 s. All images were analyzed using the Fiji image analysis software.

Transfection and Activation of Signaling Pathways in HEK293T Cell Line

HEK293T cells were transfected at about 70% confluency by using plasmid DNA:PEI=3:9 mixture. Plasmids used in this study included SRE-RLuc8, ARE-OpyLuc, and NF-κB-Akaluc, NF-κB-RLuc8, SRE-OpyLuc, ARE-Akaluc and CMV-Akaluc. 3 h after transfection, the medium was removed and replaced by fresh medium. The cells were allowed to recover for another 3 h. 20% fetal bovine serum (FBS), 50 μM tert-butylhydroquinone (tBHQ), or 10 ng/mL tumor necrosis factor alpha (TNFα) were used to activate serum response element (SRE), antioxidant response element (ARE), or nuclear factor kappa B (NF-κB) responsive element. Bioluminescence signals were acquired 16 h post induction. An un-transfected sample was used for background subtraction and an un-induced sample was used as a negative control.

Example 6

Figure 14A:
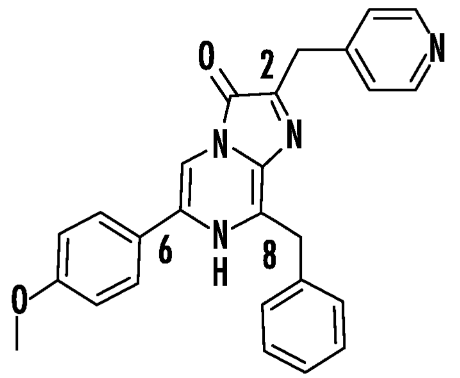
FIGS. 14A-14C show the chemical structures and maximum bioluminescence (BL) emission wavelength of (FIG. 14A) pyOMeCTZ, (FIG. 14B) pyDTZ, and (FIG. 14C) AkaLumine in the presence of its corresponding luciferase.

Design of Triple Luciferase System and the Directed Evolution of Luciferase to Improve Substrate Selectivity for Synthetic pyDTZ To choose bioluminescent reporters that can generate different colors of emission, available luciferase-luciferin pairs that have been reported previously in literature were first screened.[54] RLuc8 (nucleotide and polypeptide sequences provided herein as SEQ ID NOs.13 and 14, respectively) is able to produce intense bioluminescence in a violet wavelength range ($\lambda_{max}$: ~405 nm) when methoxy-eCoelenterazine (me-eCTZ) was used as the substrate.[55] Renilla luciferase (RLuc) is also known to be not tolerant to C-8 chemical modifications.[56] It was reasoned that the blue-shifted emission might be due to dihedral angle twist caused by the C-6 methoxyl substitution. Therefore, a me-eCTZ analog, pyOMeCTZ (FIG. 14A), with a pyridyl substitution on C-2 was synthesized to improve the water solubility by taking advantage of the fact that pyridine-containing molecules can be readily turned into pyridinium salts. As a result, RLuc8-pyOMeCTZ pair is able to generate violet emission with $\lambda_{max}$ at about 416 nm, or yield a bioluminescence of about 380-470 (nm).

Figure 14B:
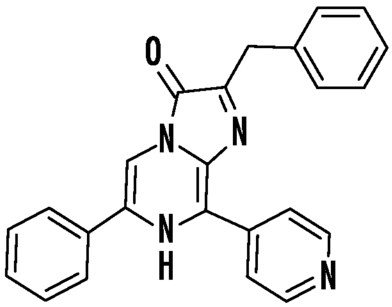
Figure 14C:
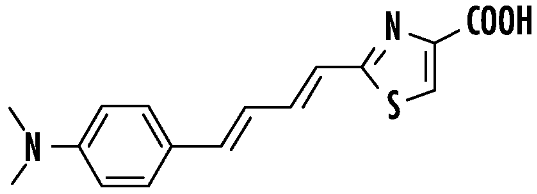

According to our result, teLuc is tolerant to a variety of C-8 chemical modifications, including both electronic and steric derivatives.[53] Herein, pyDTZ (FIG. 14B) that can emit green to yellow photons ($\lambda_{max}$: about 530 nm, or yield a bioluminescence of about 480-600 (nm)) when paired with teLuc was synthesized. Since the emission wavelength between RLuc8-pyOMeCTZ and teLuc-pyDTZ pairs are well resolved, they are readily available to pair with Akaluc (nucleotide and polypeptide sequences provided herein as SEQ ID NOs. 15 and 16, respectively)-AkaLumine pair that produces near infrared (NIR) photons[57] ($\lambda_{max}$: about 650 nm, or yield a bioluminescence of about 600-750 (nm); FIG. 14C) to yield a triple-color luciferase reporter system. It has been known that CTZ-utilizing murine luciferases do not have substrate cross-talk with D-luciferin-utilizing insect luciferases, so the remaining issue is the substrate selectivity between RLuc8 and teLuc to engineer a fully orthogonal triple-color luciferase system.

Figure 15A:
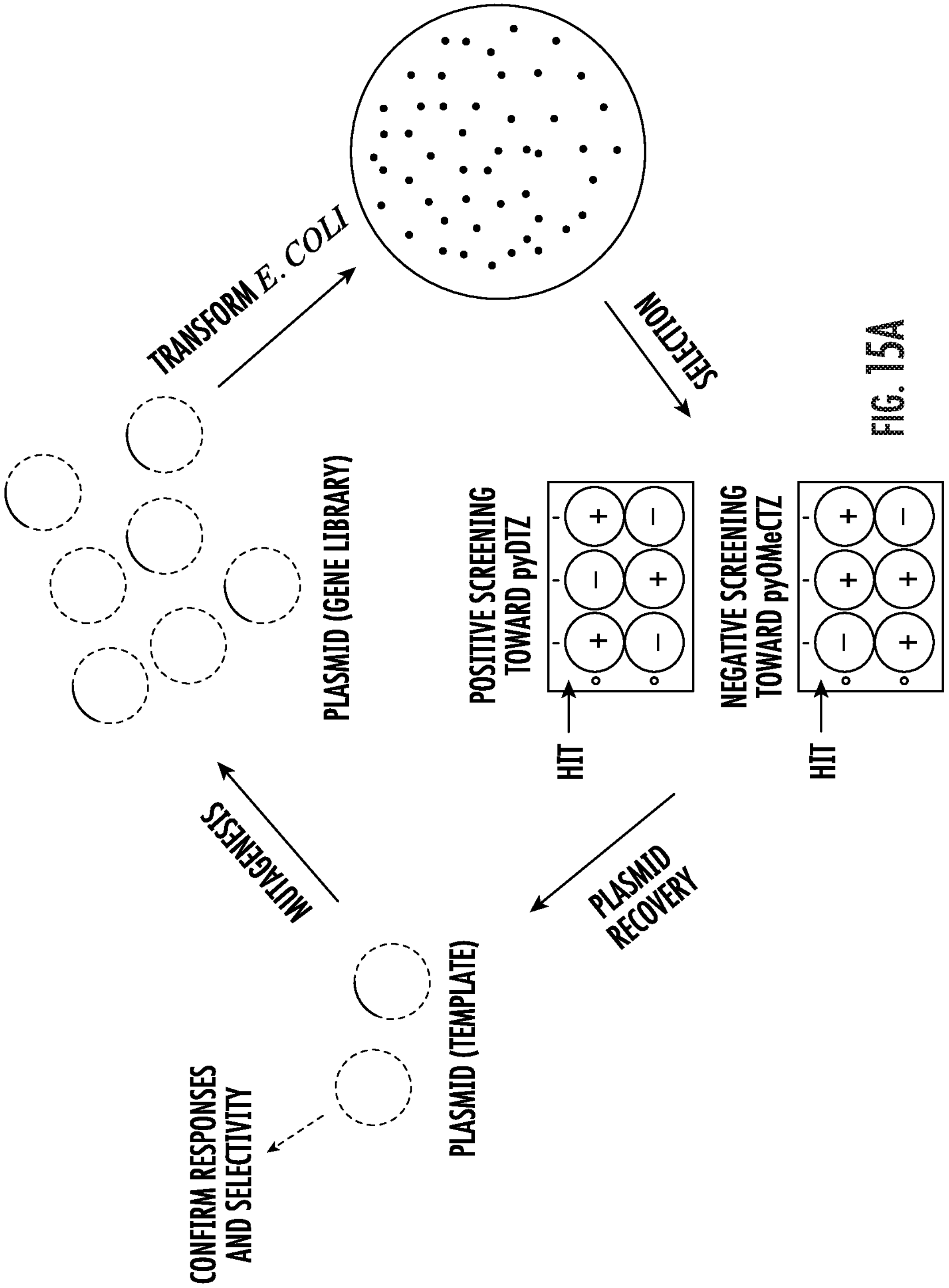
FIGS. 15A-15C show engineering of OpyLuc luciferase for pyDTZ selectivity over pyOMeCTZ.
Figure 15B:
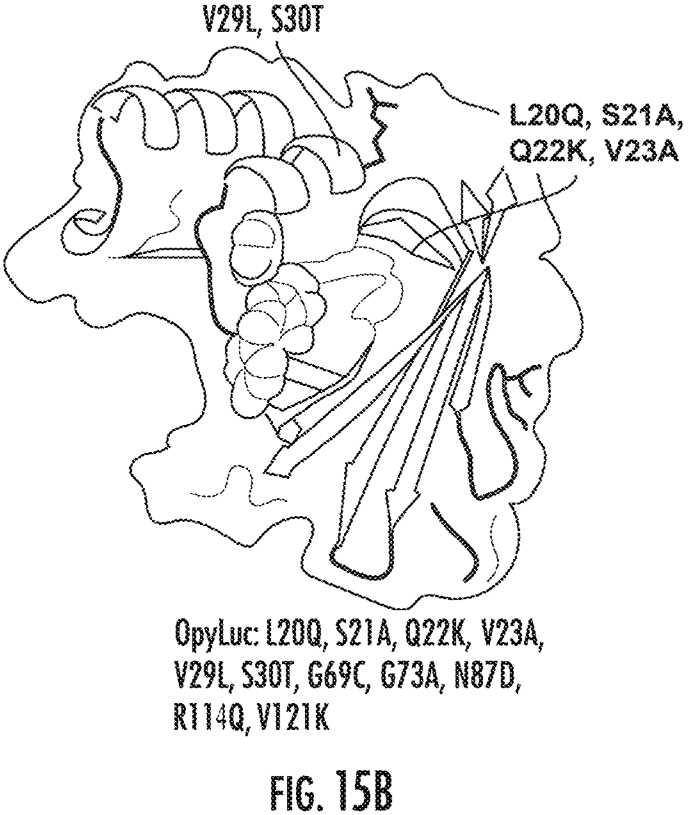
Figure 15C:
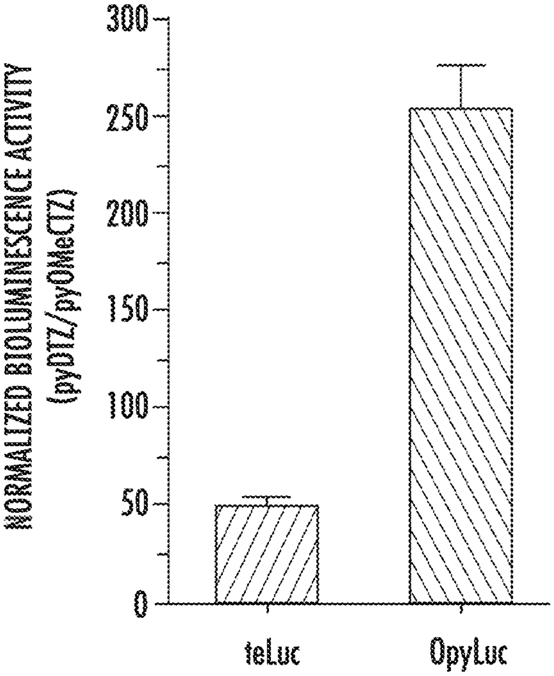
Figure 16:
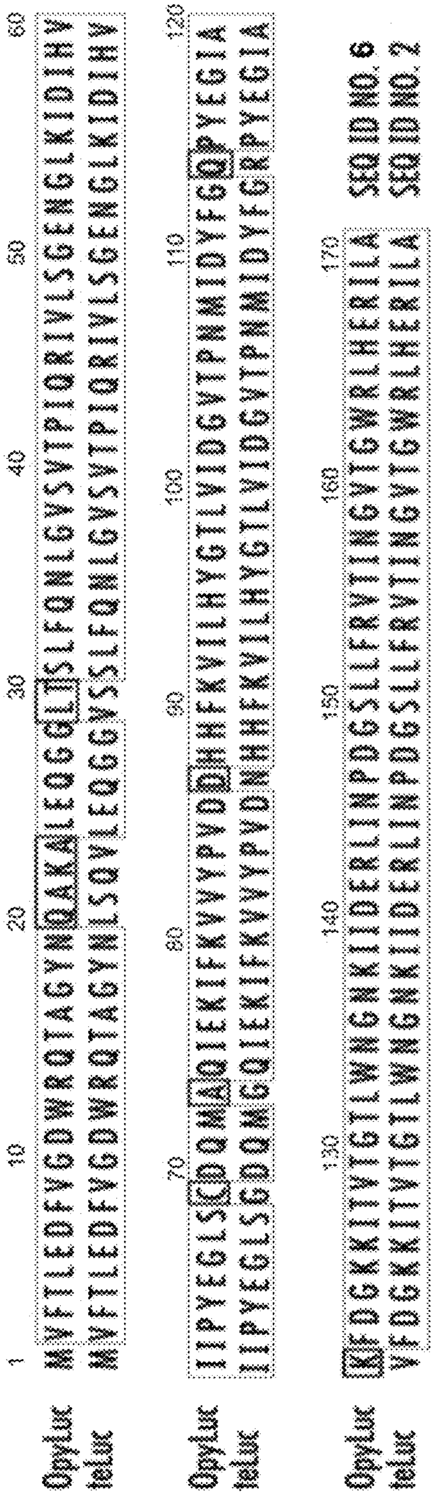
FIG. 16 shows the alignments of primary polypeptide sequences of OpyLuc (SEQ ID NO. 6) and teLuc (SEQ ID NO. 2). OpyLuc mutations are highlighted.

To address this issue, it was noticed that teLuc exhibited a substrate preference to pyDTZ over pyOMeCTZ by about 50-fold activity, suggesting that it might be feasible to engineer a mutant via directed evolution to more selectively access pyDTZ rather than pyOMeCTZ. Instead of screening the library for only enhanced bioluminescence output, a method was designed where the BL activity of the mutants to both of pyDTZ (positive screening) and pyOMeCTZ (negative screening) were screened in parallel. The "hit" mutants showing not only high specific activity in positive screening but also low activity in negative screening were selected for the next round selection (FIG. 15A). After 8 rounds of selection, a mutant (designated OpyLuc; SEQ ID NO. 6) carried 11 mutations was obtained (FIG. 15B, and FIG. 16) and showed about 250-fold selectivity to pyDTZ over pyOMeCTZ (FIG. 15C). Notably, Q22K and V23A mutations were acquired during random mutagenesis, suggesting residues nearby the catalytic site contribute to the substrate selectivity.

Figure 17A:
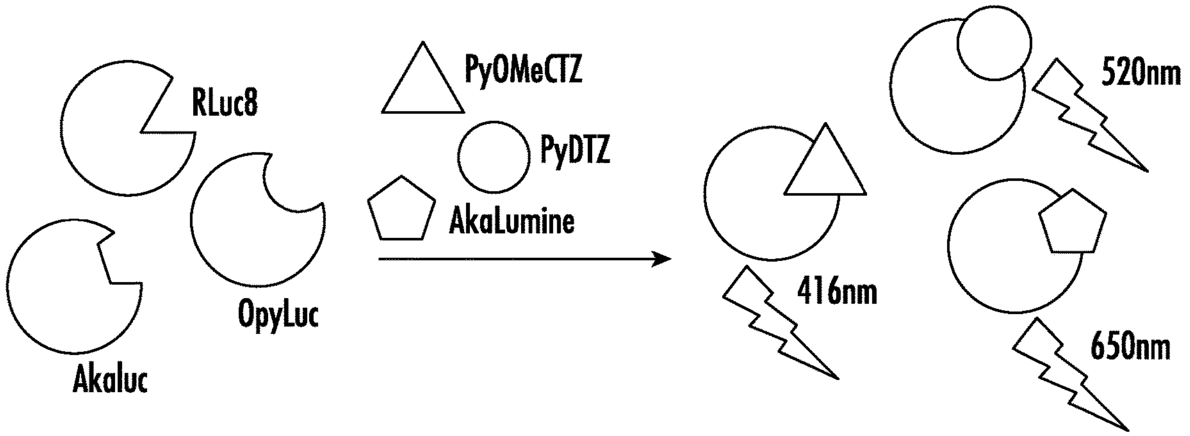
FIGS. 17A and B show the results of the analysis of orthogonal luciferase-luciferin pairs.
Figure 17B:
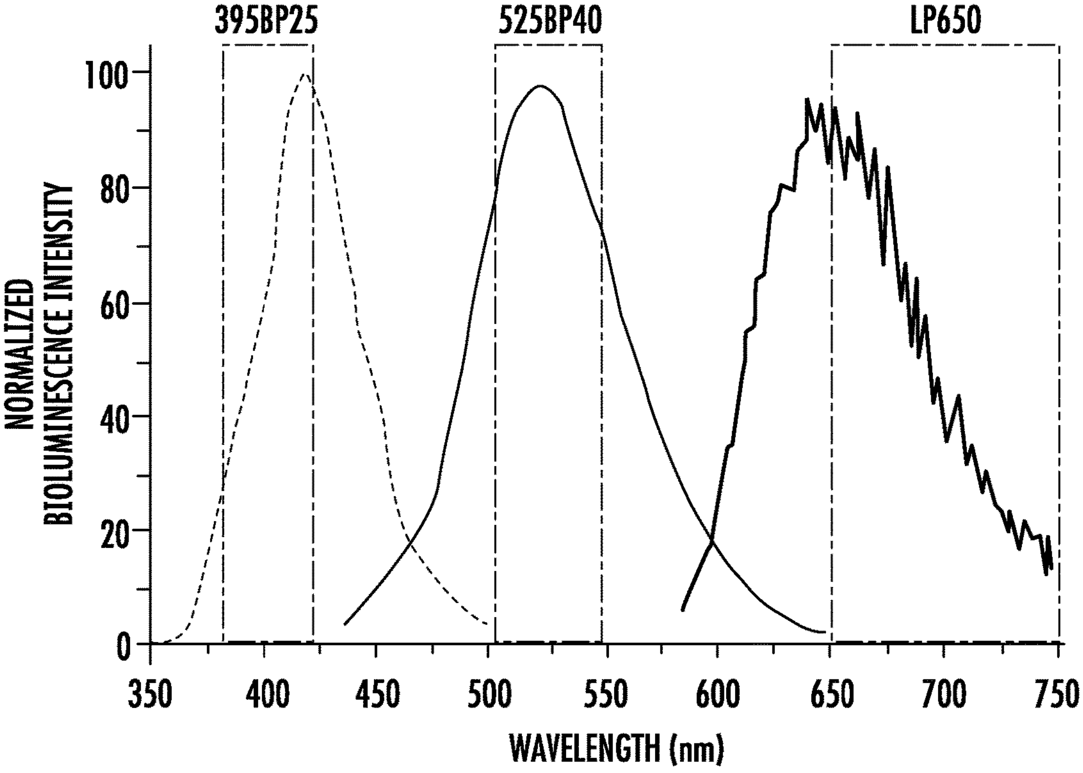
(FIG. 17B) Normalized bioluminescence emission spectra of RLuc8-pyOMeCTZ (purple), OpyLuc-pyDTZ (green), and Akaluc-AkaLumine pairs (red).
Figure 18A:
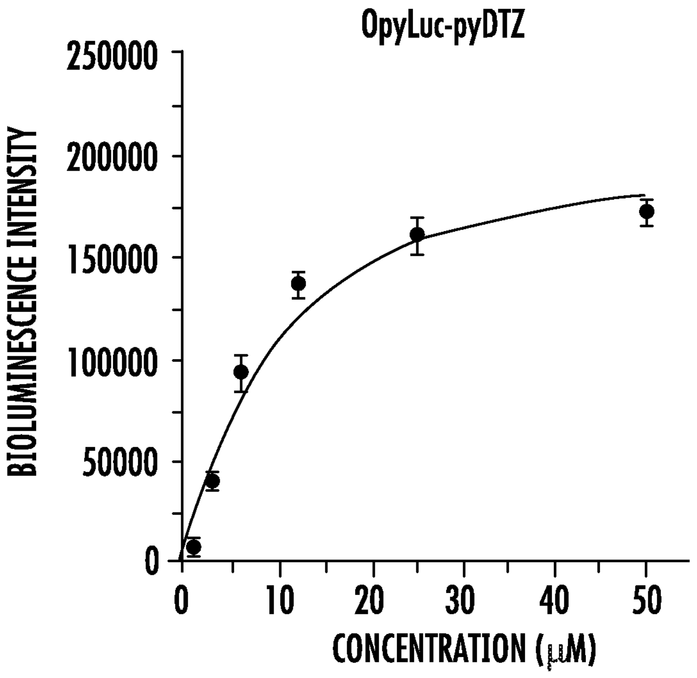
Figure 18B:
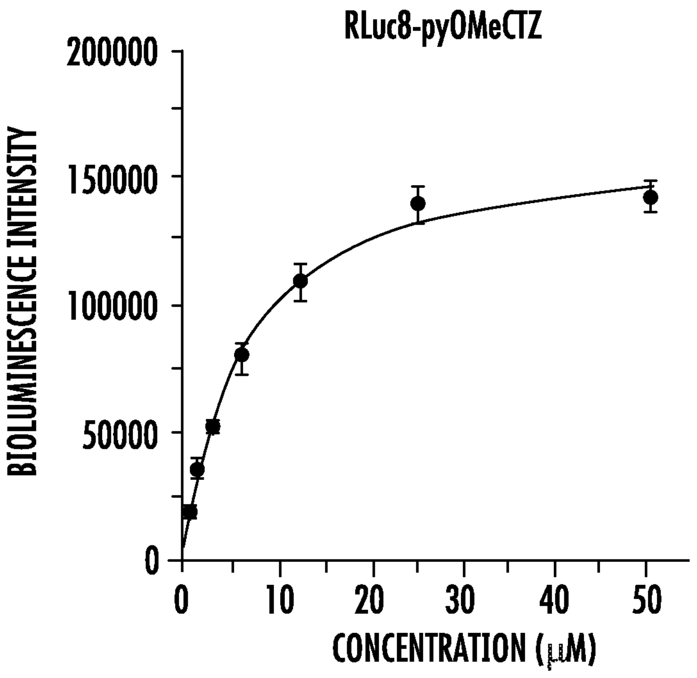
(FIG. 18B) RLuc8-pyOMeCTZ: 6.3±0.5 μM. Final concentrations of all enzymes were 100 pM. Substrate concentrations varied from 0.78 to 50 μM, and 10 min integration of total bioluminescence intensities at individual substrate concentrations were used to fit the Michaelis-Menten equation.

Collectively, provided herein are three luciferase-luciferin pairs (RLuc8-pyOMeCTZ; $\lambda_{max}$: 416 nm, OpyLuc-pyDTZ; $\lambda_{max}$: 520 nm, and Akaluc-AkaLumine; $\lambda_{max}$. 650 nm) that can access its specific luciferin and produce distinct colors of emission across the visible spectrum (FIGS. 17A, 18A and 18B). Their emission spectra are well separated and with only minimal spectra cross-talk. These features allow researcher to either initiate a specific luciferase activity by adding its corresponding luciferin substrate or scan the full spectra or use commercial filters to determine individual luciferase signals, thereby providing flexible data acquisition methods for any chosen purpose (FIG. 17B).

Example 7

Figure 19A:
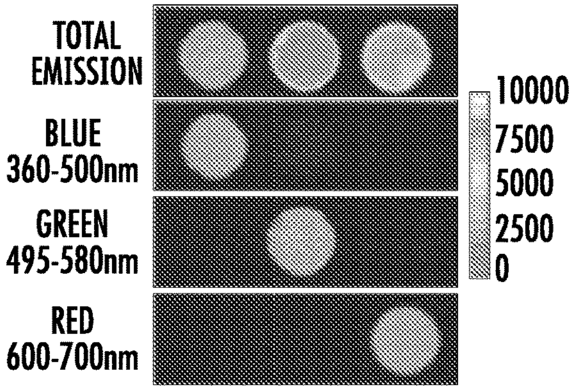
FIGS. 19A-19D show bioluminescence imaging of (FIGS. 19A-B) purified recombinant RLuc8, OpyLuc, and Akaluc and (FIGS. 19C-D) luciferase-expressing HEK 293T cells.
Figure 19B:
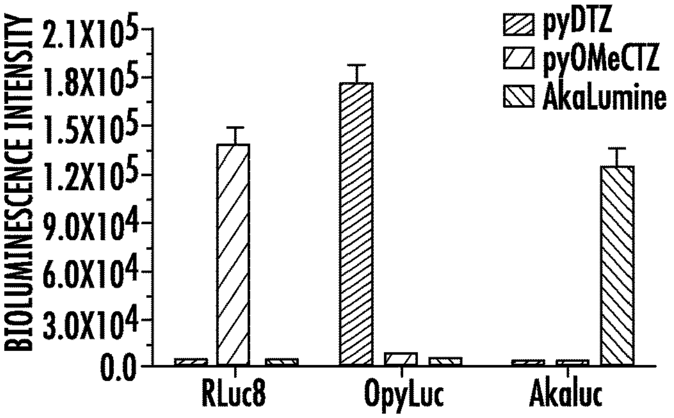

Triple Luciferase System Produces Orthogonal BL Signals in Purified Enzyme and in Transfected HEK293T Cells To validate that the emission of these three luciferase-luciferin pairs are indeed spectrally separated, and can be resolved by filters, recombinant luciferases were first purified from *E. coli* and the respective BL signals were imaged with/without 360-500 nm, 495-580 nm, or 600-700 nm bandpass filters (FIGS. 19A and 19B). The result indicated RLuc8-pyOMeCTZ, OpyLuc-pyDTZ, and Akaluc-AkaLumine pairs all give the highest signal under the filter set-up that matches its respective emission color, suggesting their emission spectra can be well separated simultaneously by a set of commercial filters. Since these signals can be recorded in the same time, it solved the need of sequential sampling by Promega Dual-Luciferase Reporter assay.

To demonstrate that the disclosed triple luciferase system is a practical tool to monitor gene expression levels in live mammalian cells, the photon flux of each luciferase was first evaluated in the presence of a series of substrate concentrations. It would have been ideal to explore an optimal concentration for each luciferin (pyOMeCTZ, pyDTZ, and AkaLumine) that can provide a similar level of photon flux from individual luciferase-luciferin pair. Unfortunately, the photon flux of Akaluc-AkaLumine at saturated concentration is about 10-fold lower than that of RLuc8-pyOMeCTZ and OpyLuc-pyDTZ pairs, possibly due to its nature BL mechanism of ATP-dependency and two-step reaction. In order to at least keep the photon flux of RLuc8-pyOMeCTZ and OpyLuc-pyDTZ pairs at the same level, a condition containing 25 μM pyOMeCTZ, 10 μM pyDTZ, and 100 μM AkaLumine-HCl was selected as the "Optimal Mix" for live cell imaging. By comparing Optimal Mix and only its respective substrate, only OpyLuc exhibited slightly unspecific inhibition by Optimal Mix while RLuc8 and Akaluc remained unaffected.

Figure 19C:
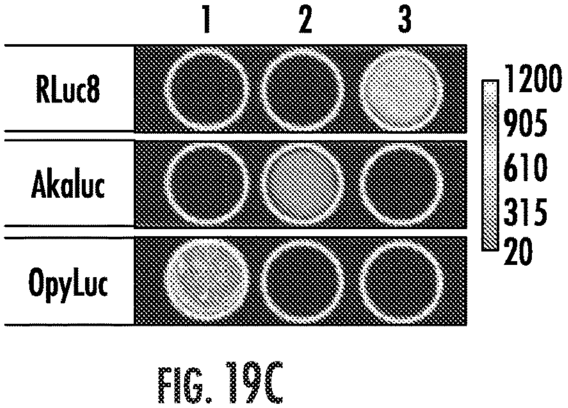
Figure 19D:
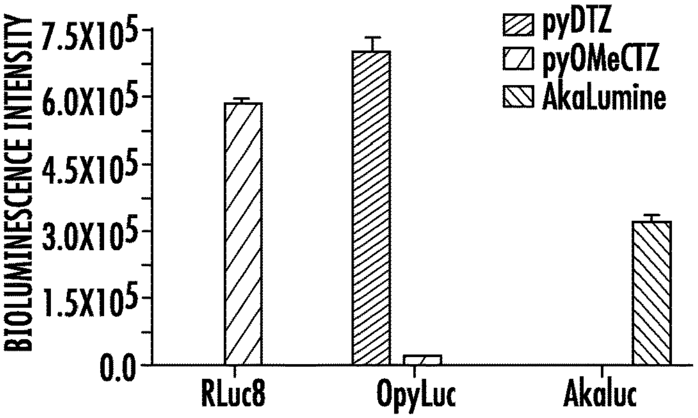

Next, the performance of each luciferase was examined for in cellulo imaging in the presence of chosen luciferin concentration. The indicated luciferin substrate solution was injected into luciferase-expressing HEK 293T cells in a 96-well plate. As expected, pyDTZ initiated the BL emission only in the presence of OpyLuc. The excellent substrate selectivity was also observed in both Akaluc for AkaLumine and RLuc8 for pyOMeCTZ (FIGS. 19C and 19D). Taken together, the results indicated again that each of luciferase in the disclosed triple luciferase system can process its distinct substrate and generate distinguishable emission wavelength. To briefly sum up, each luciferase can be selectively activated by its specific luciferin and the emission photons can also be distinguished by wavelength, which provided the flexibility to monitor multiple transcriptional activities specifically, stepwise, or simultaneously as a versatile experimental design. Moreover, the equations to calculate the activities of the individual luciferases by splitting emissions is not necessarily required since the spectra cross-talks are minimized.

While reporter assays are typically performed in lysates from cultured cells, the disclosed triple luciferase system was also evaluated in lysates. The results indicated that RLuc8-pyOMeCTZ and OpyLuc-pyDTZ pairs showed about 2 to 3-fold higher BL signals in lysates while Akaluc-AkaLumine exhibited decreased signal even after supplementing with additional ATP. Therefore, using lysates in not required in the disclosed triple luciferase system because all three luciferins described here are cell-permeable and work well with intact mammalian cells. This feature is beneficial to expand the real-time measurement of BL assays without lysing cultured cells.

Example 8

Figure 20A:
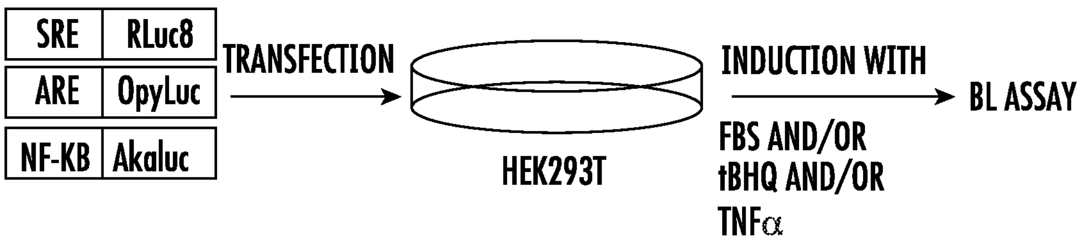
FIG. 20A shows results of the triple luciferase assay in live HEK293T after co-transfection of SRE-RLuc8, ARE-OpyLuc, and NFκB-Akaluc plasmids.

Monitor Serum Response, Antioxidant, and NF-κB Promoter Activities in HEK293T Cells by Triple Luciferase System Subsequently, the disclosed triple luciferase system was used to monitor three signaling pathway activations in HEK293T cells where each of the luciferase expression was under control by a growth factor-regulated promoter element (serum response element, SRE),[58] a Nrf2-antioxidant response element (ARE),[59] or a transcription factor-nuclear factor kappa B (NF-κB) responsive promoter element (Table 5).[60] A reporter system was designed based on SRE promoter driving the expression of RLuc8, ARE promoter driving the expression of OpyLuc, and NF-κB promoter driving the expression of Akaluc. The response element promoters can be specifically activated by its respective stimuli-fetal bovine serum (FBS), tert-butylhydroquinone (tBHQ), and tumor necrosis factor alpha (TNFα) (FIG. 20A).

TABLE 5

Oligonucleotides used in this study.

| Oligo name | SEQ ID NO. | Nucleotide sequence (5'->3') |
|---|---|---|
| L18D19NNK-F | 29 | CAGACAGCCGGCTACAACNNKNNKCAAGTCCTTGAACAGGGAGGTGTG |
| L18D19NNK-R | 30 | CACACCTCCCTGTTCAAG GACTTGMNNMNNGTTGTAGCCGGCTGTCTG |
| 27VSSNNK-F | 31 | CAAGTCCTTGAACAGGGAGGTNNKNNKNNKTTGTTTCAGAATCTCGGGGTG |
| 27VSSNNK-R | 32 | CACCCCGAGATTCTGAAACAAMNNMNNMNNACCTCCCTGTTCAAGGACTTG |
| pBAD-F | 33 | ATGCCATAGCATTTTTATCC |
| pBAD-R | 34 | GATTTAATCTGTATCAGG |
| HindIII-pyr-F-Koz | 35 | AATAAAGCTTGCCGCCACCATGGTCTTCACTCTCGGGGATTTT |
| pyr-R-XhoI | 36 | TAATTCTCGAGTTACGCCAGAATGCGTTCATGCAG |
| Aka-F-HindIII-Kozak | 37 | ATTATAAAGCTTGCCGCCACCATGGAAGATGCCAAAAACATTAAGA |
| Aka-R-XhoI | 38 | TTATTCTCGAGTTACACGGCGATCTTGCCGTCCTTCTT |
| Aka-F-XhoI | 39 | ATAACTCGAGCATGGAAGATGCCAAAAACATTAAGA |
| Aka-R-HindIII | 40 | TTGCCAAGCTTACACGGCGATCTTGCCGTCCTTCTT |
| HindIII- | 41 | ATTATAAAGCTTGCCGCCACCATGGTGAGC |

TABLE 5-continued

Oligonucleotides used in this study.

| Oligo name | SEQ ID NO. | Nucleotide sequence (5'->3') |
|---|---|---|
| mScarlet-F-Koz | | AAGGGCGAGGCAGT |
| mScarlet-F-XhoI | 42 | ATAACTCGAGCATGGTGAGCAAGGGCGAGGCAGTG |
| pyr-R-HindIII | 43 | TTGCCAAGCTTACGCCAGAATGCGTTCATGCA |
| mScar-NNK-pyr-F | 44 | GAGGGCCGCCACTCCACCGGANNKACTCTCGGGGATTTTGTTGGG |
| mScar-NNK-pyr-R | 45 | CCCAACAAAATCCCCGAGAGTMNNTCCGGTGGAGTGGCGGCCCTC |

Figure 20B:
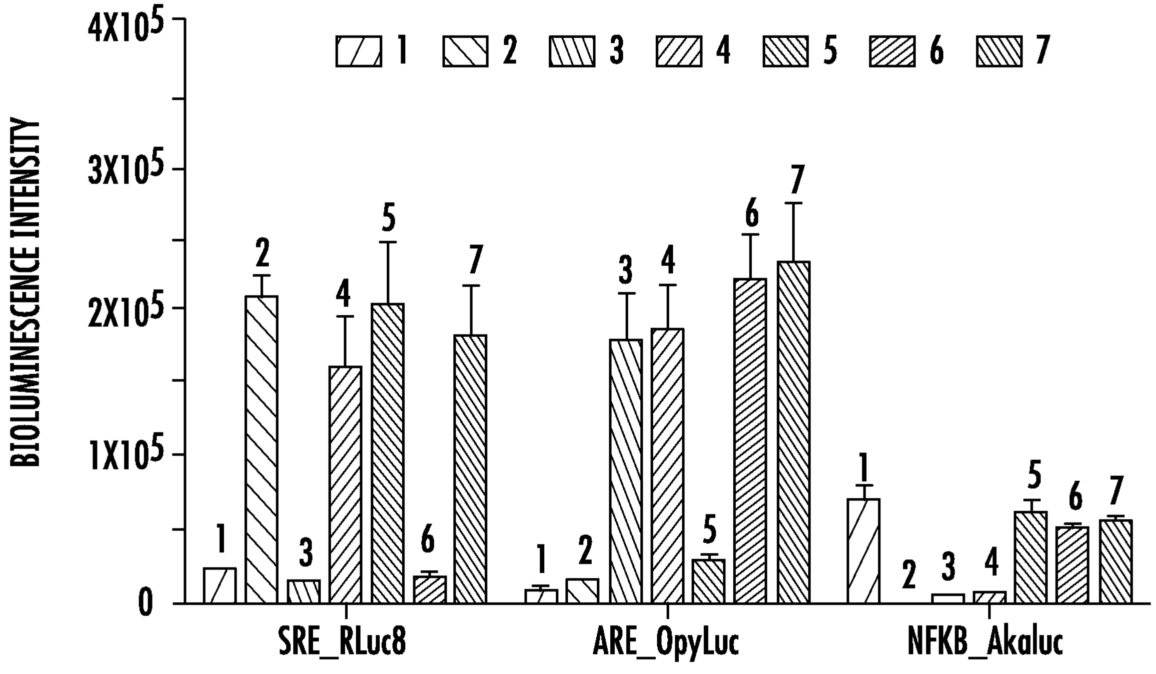
FIG. 20B shows the BL signals from each luciferase were acquired from intact cells after adding its corresponding luciferin. The cells were induced by 1: 10 ng/mL TNFα; 2: 20% FBS; 3: 50 μM tBHQ; 4: 20% FBS+50 μM tBHQ; 5: 20% FBS+10 ng/mL TNFα, 6:50 μM tBHQ+10 ng/mL TNFα; 7: 20% FBS+50 μM tBHQ+10 ng/mL TNFα for 16 h post PEI transfection.
Figure 21A:
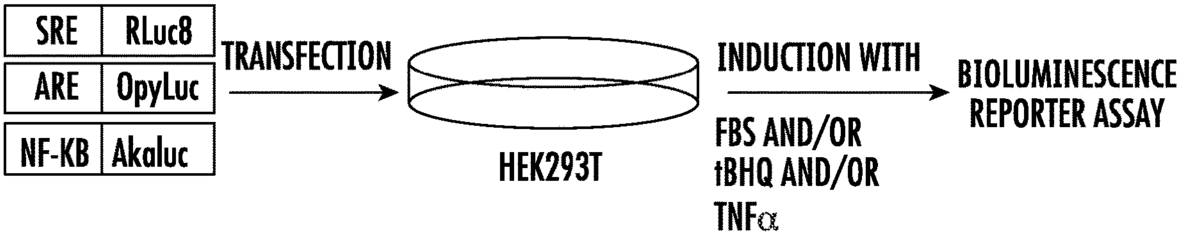
FIGS. 21A-21I show results of triple luciferase assay in live HEK293T after co-transfection of SRE-RLuc8, ARE-OpyLuc, and NFκB-Akaluc plasmids.
Figure 21B:
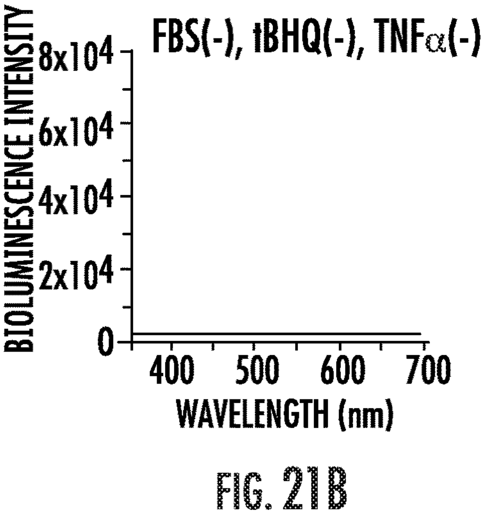
Figure 21C:
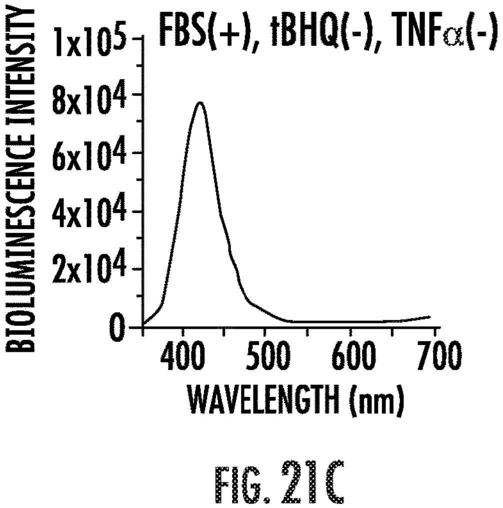
Figure 21D:
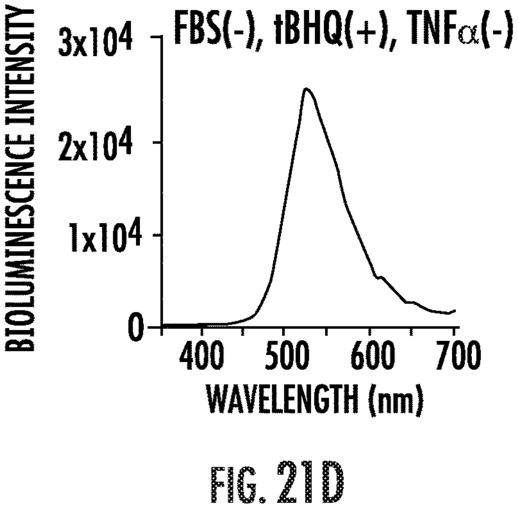
Figure 21E:
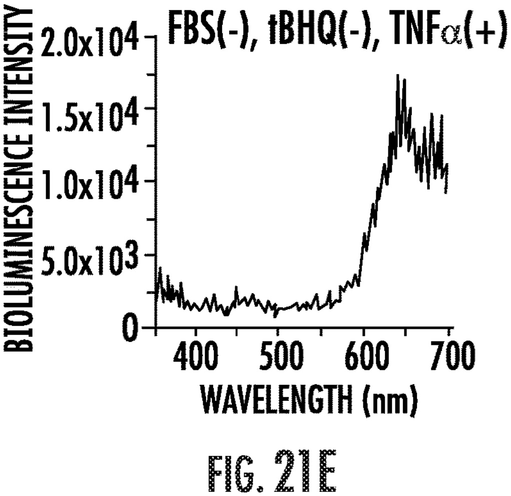

The basal promoter activities of all SRE, ARE, and NF-κB response elements were low (FIG. 6A). The individual luciferase activity was measured (RLuc8, OpyLuc, and Akaluc) by adding its corresponding luciferin (pyO-MeCTZ, pyDTZ, and AkaLumine). As expected, treating with single stimuli enabled the activation of its specific pathway and drove the downstream expression of genetically encoded luciferase. Stimulating the cells with either two or three stimuli resulted in activation of multi-pathway and were reported correctly by our triple luciferase system (FIG. 20B). Next, the emission spectra were recorded after injection of Optimal Mix solution to the transfected HEK293T cells (FIG. 20B and FIGS. 21C, D, and E). Due to the fact that all three emission spectra are well-separated, this system demonstrated a proof-of-concept of simultaneous recording of three pathway activations. Again, the results suggested that there is no cross-reactivity between each luciferase-luciferin pair, providing an advantage in future studies that require either sequential or simultaneous multicomponent monitoring.

Figure 21F:
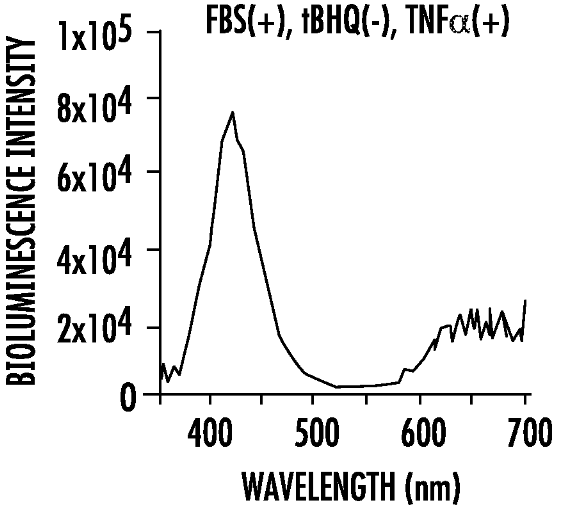
Figure 21G:
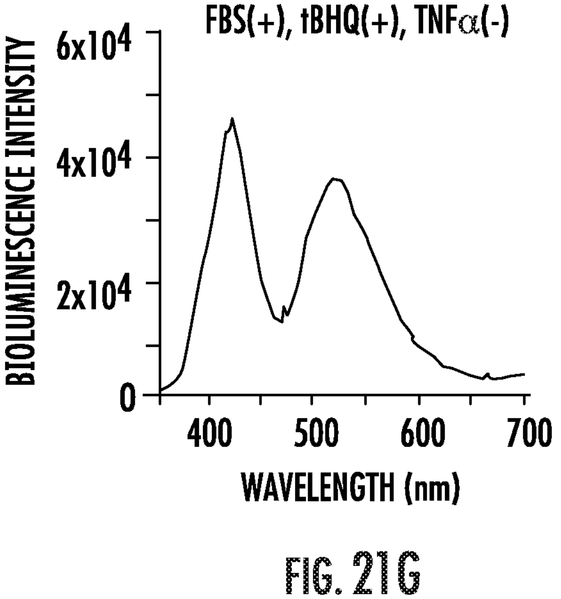
Figure 21H:
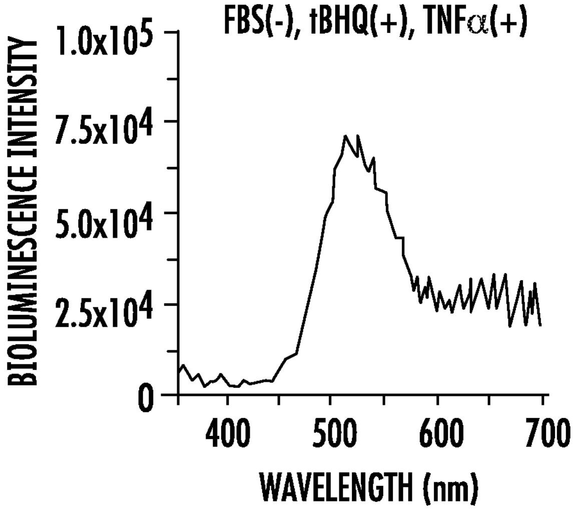
Figure 21I:
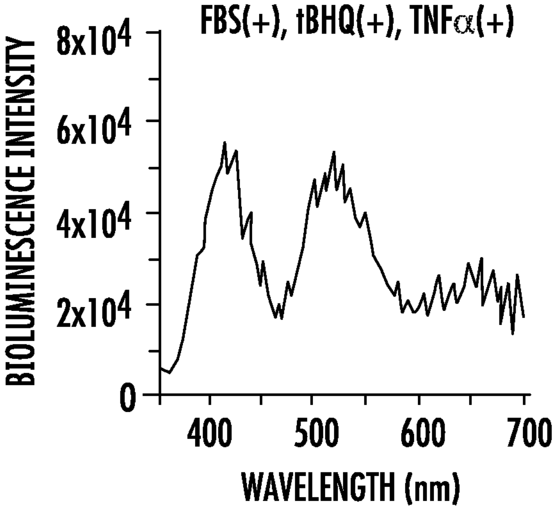

Herein, the ability of the disclose triple luciferase system to monitor the simultaneous activation of two or all three labeled pathways was demonstrated. The ability to qualitatively detect three signaling activation states after treating with stimuli mixtures was demonstrated (FIGS. 20B and 21F, G, H, and I).

Next, the promoters were switched over to drive the downstream luciferase expression by using an alternative combination (NF-κB-RLuc8, SRE-OpyLuc, and ARE-Akaluc). After inducing with all stimuli (TNFα, FBS, and tBHQ), the signals from RLuc8 and OpyLuc were obvious as expected, while the signal from Akaluc was overwritten by the broad emission tailing of OpyLuc (FIG. 21). This result suggested that Akaluc is only suitable to monitor strong promoter activity when paired with the other two luciferases, because the photon flux of Akaluc is relatively lower. This is a factor that needs to be taken into account when researchers conducting the initial experimental design.

These data support the use of the new luciferase-luciferin pairs for assays of cell signaling pathways. Particularly, the data summarized in FIG. 21 suggest that the use of the disclosed luciferase-luciferin pairs can allow for the monitoring of particular cell signaling pathways, which can be implemented to for candidate compound and drug screening applications.

Example 9

Akaluc-AkaLumine Pair is More Suitable as an Internal Control

Figure 6B:
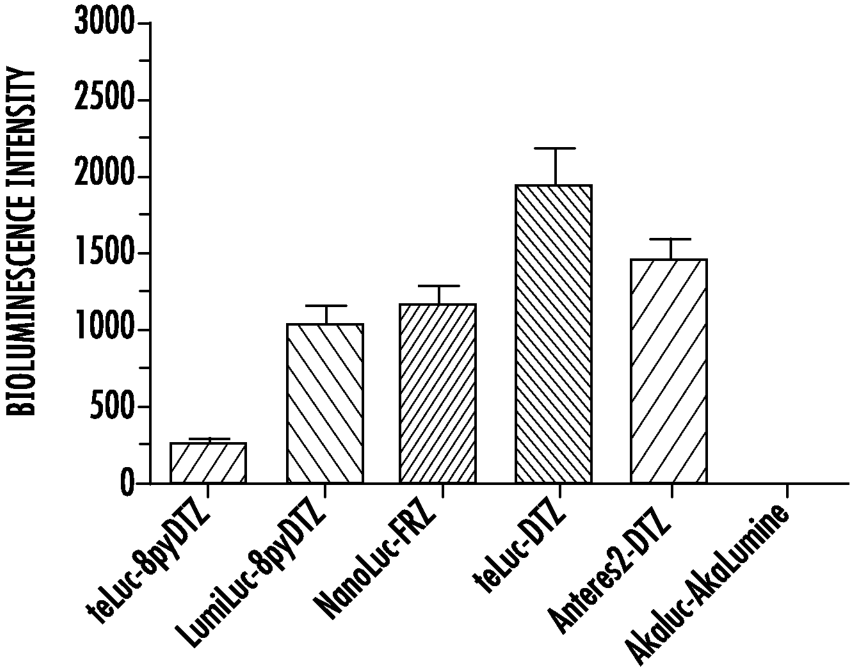
Figure 6C:
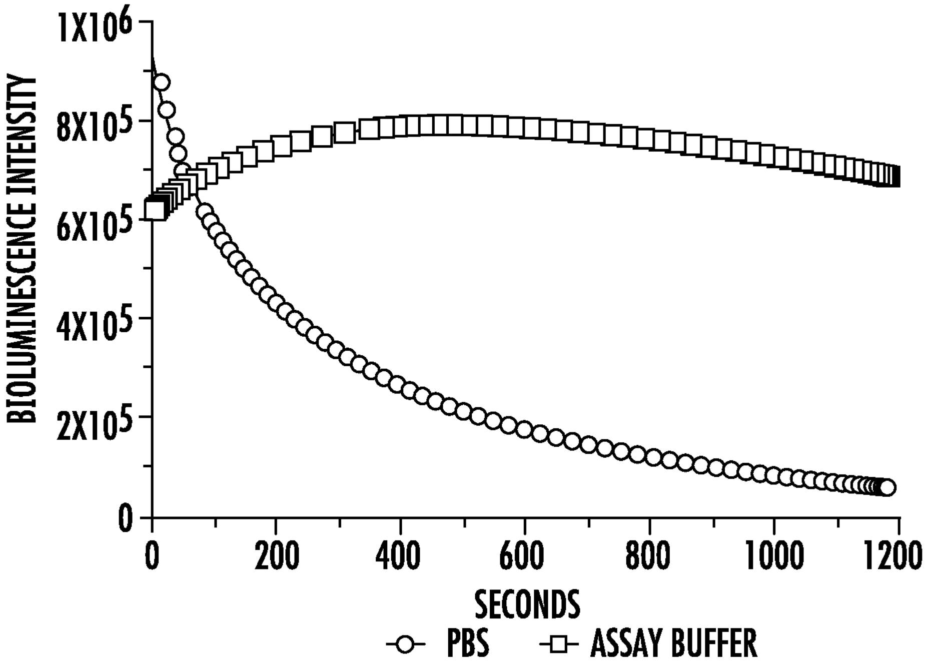

As mentioned above, it is recommended to normalize the BL assay results by an internal control for cell number, and transfection efficiency normalizations. Another set of plasmids containing NF-κB-RLuc8, SRE-OpyLuc, and a control of the constitutively active cytomegalovirus (CMV) promoter (CMV-Akaluc) was prepared. The cells were transfected with all three plasmids and incubated with two stimuli (TNFα and FBS) for 16 h. In this case, the BL signal was selectively triggered from individual luciferase by adding its respective luciferin to intact cells (FIG. 6A). The BL kinetics were monitored for each luciferase after the addition of its respective luciferin (FIG. 6B). All three luciferase generated BL signal, and the BL signal attenuated by the function of time. The advantage of incorporating an internal control here is not only limited to the normalization of cell number and transfection efficiency of each sample, but also the kinetic of each BL signal can be normalized to give a more constant ratio readout, which is more amenable to high-throughput screening (FIG. 6C). Thus, this system enabled the monitoring of two signaling activations and improved the accuracy of assay by including another orthogonal control to exclude factors such as cell number, transfection efficiency, and BL emission kinetic.

Example 10

Figure 22A:
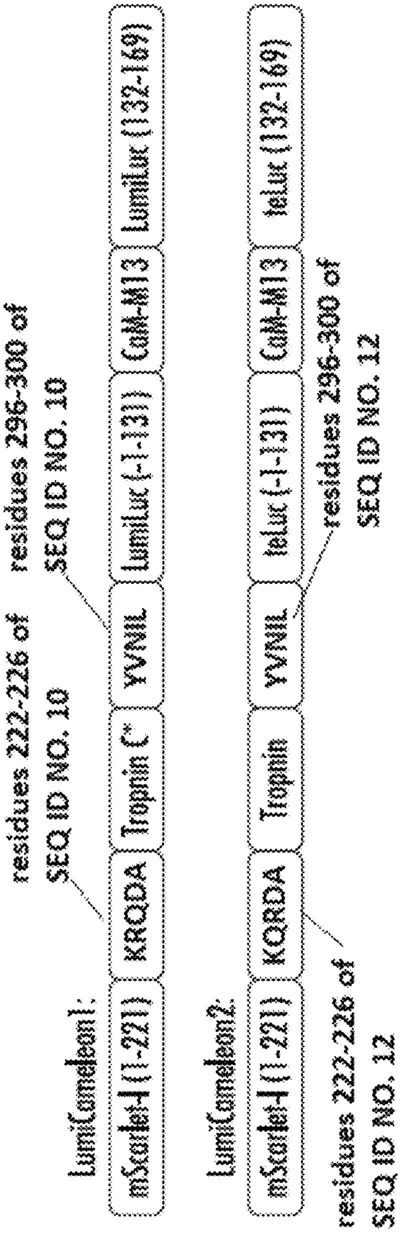
FIGS. 22A-22C show bioluminescent $Ca^{2+}$ biosensors.
Figure 22B:
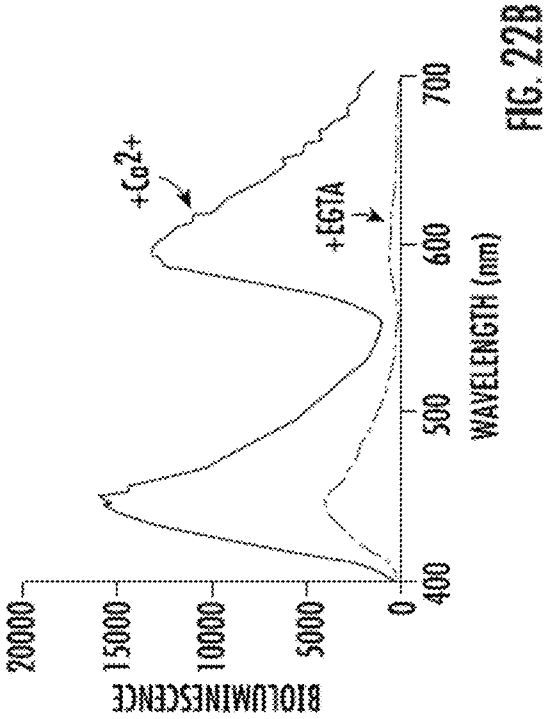
Figure 22C:
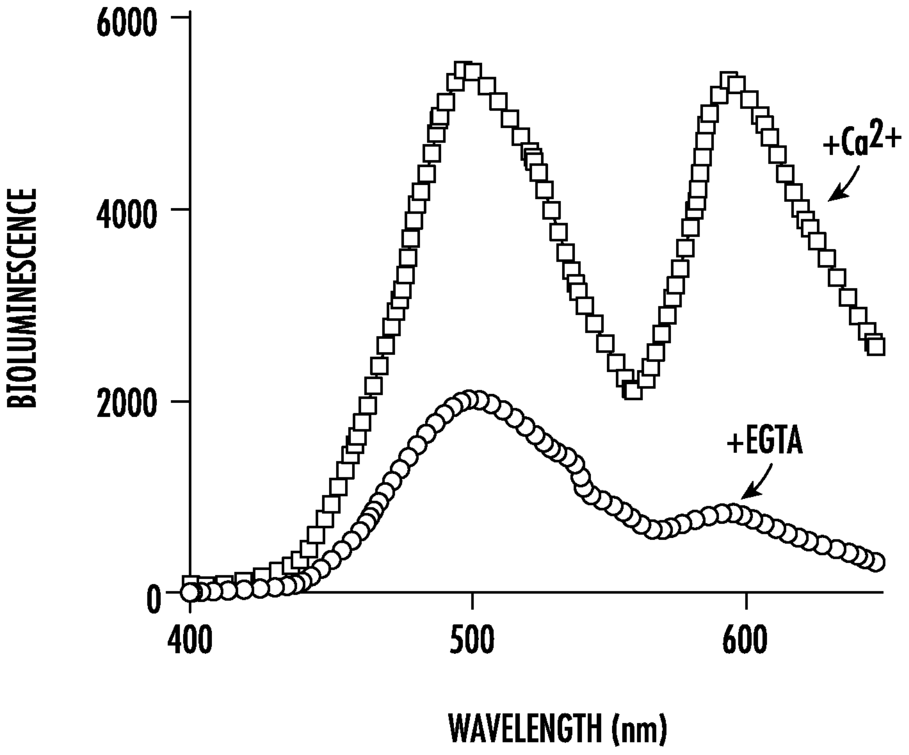

Analysis of Bioluminescent $Ca^{2+}$ Biosensors $Ca^{2+}$ is one of the most important signaling cations in biological systems. Bioluminescent $Ca^{2+}$ biosensors are expected to have broad applications in non-invasive imaging and drug screening. Recent studies have reported a few bioluminescent $Ca^{2+}$ biosensors based on NanoLuc.[65-68] To address the limitations of these existing sensors, such as small dynamic range, low brightness, and/or relatively blue emission, $Ca^{2+}$ biosensors based on the disclosed brighter and redder luciferase-luciferin pairs were developed. Moreover, in contrast to existing approaches, multiple $Ca^{2+}$ binding elements were introduced to modulate bioluminescence through two different mechanisms. In particular, a calcium sensory element (e.g., a modified Troponin C) was sandwiched between a LumiLuc and Scarlet-I BRET pair. After testing several linker lengths, a prototypic biosensor was derived, whose bioluminescence at wavelengths longer than 600 nm increases by about 4-fold in response to $Ca^{2+}$. Further, calmodulin and M13 were inserted between the residue 133 and 134 of Lumiluc to modulate its intensity, resulting in LumiCameleon1 (FIGS. 22A and 22B; SEQ ID NOs. 9 and 10) showing a total of greater than about 20-fold increase of greater than about 600 nm emission in response to $Ca^{2+}$. The brightness of LumiCameleon1 in the $Ca^{2+}$ saturated state is about 52% of LumiScarlet. This sensor is thus well suited for in vivo and in vitro applications, because of its high brightness, large dynamic range, and red-shifted emission compared to any previously reported NanoLuc-based $Ca^{2+}$ sensor. Along the same line, a similar biosensor based on teLuc was created. The resultant LumiCameleon2 (FIGS. 22A and 22C; SEQ ID NOs. 11 and 12) also showed a large bioluminescence increase in response to $Ca^{2+}$.

Discussion of Examples 6-10

Herein, substrate selectivity was utilized to engineer a mutually orthogonal luciferase-luciferin pair for multiplexed cell-based BL assay. In combination with RLuc8 and Akaluc, this triple-color BL system features the selectivity of synthetic substrates and production of well separated emission spectra from 400 nm to 650 nm. Several advantages of previous bioluminescence technology (Table 6) were combined to develop a spectral-resolved triple-color BL system, which provides flexible and convenient approaches to monitor multiple biological events in either qualitative or quantitative manners.

New bioluminescent $Ca^{2+}$ biosensors were also developed based on the modified luciferase compounds disclosed herein. These bioluminescent $Ca^{2+}$ biosensors showed large bioluminescence increase in response to $Ca^{2+}$, making them well suited for in vivo and in vitro applications.

TABLE 6

Qualitative comparison of this study and commercial luciferase reporter systems

| | Promega Dual-Luciferase Assay | Promega Chroma-Glo | Pierce Cypridina-Firefly Luciferase Dual Assay | Orthogonal Triple Luciferase Assay (this work) |
|---|---|---|---|---|
| Number of Substrates | 2 | 1 | 2 | 3 |
| Types of Enzymes | 2 (Rluc, FLuc) | 1 (2 CBLucs) | 2 (VLuc, Red FLuc) | 3 |
| Gene Identity | low | >99% | low | low |
| Orthogonal Signals | Yes | No | Yes | Yes |
| Simultaneous Detection of 2 Signals | No | Yes | Yes | Yes |
| Simultaneous Detection of 3 Signals | No | No | No | Yes |
| Data Calculations Required | No | Yes | No | Yes/No |
| Luminometer Filters Required | No | Yes | Yes | Yes/No |
| Single Reagent Solution | No (CTZ, D-luciferin) | Yes (D-luciferin) | Yes (Vargulin, D-luciferin) | Yes (pyDTZ, pyOMeCTZ, Akalumine-HCl) |
| Emission Signals Well-Separated | Yes | No | Yes | Yes |
| Cell Lysis Required | Yes | Yes | Yes | Yes/No |

By using this triple luciferase system, it was demonstrated that the activations of cell signaling can be detected simultaneously or separately from live cells in a single experiment where each individual BL signal can be distinguished from the other two luciferase-luciferin pairs. It is expected that there is also an ability to combine newly discovered luciferase-luciferin pairs[61] to independently activate even more innate processes in the same sample to study the cross-talks of cellular signaling pathways. Moreover, multiplexed BL assay is compatible with modem genetically encoded fluorescent biosensors to further investigate complexed biological events via functional imaging.[62] The development of a such versatile tool ensures an accurate and precise analysis of signaling pathways which will extend to study other physiologically transcriptional activation and is critical to improve the design and screening of new drugs, as well as the diagnosis and treatment of disease.

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

1. Rodriguez, E. A., Campbell, R. E., Lin, J. Y., Lin, M. Z., Miyawaki, A., Palmer, A. E., Shu, X., Zhang, J., and Tsien, R. Y. (2017) The Growing and Glowing Toolbox of Fluorescent and Photoactive Proteins, Trends Biochem. Sci. 42, 111-129.
2. Sadikot, R. T., and Blackwell, T. S. (2005) Bioluminescence imaging, Proc. Am. Thorac. Soc. 2, 537-540, 511-532.
3. Mezzanotte, L., van't Root, M., Karatas, H., Goun, E. A., and Lowik, C. (2017) In Vivo Molecular Bioluminescence Imaging: New Tools and Applications, Trends Biotechnol. 35, 640-652.
4. Yao, Z., Zhang, B. S., and Prescher, J. A. (2018) Advances in bioluminescence imaging: new probes from old recipes, Curr. Opin. Chem. Biol. 45, 148-156.
5. Adams, S. T., Jr., and Miller, S. C. (2014) Beyond D-luciferin: expanding the scope of bioluminescence imaging in vivo, Curr. Opin. Chem. Biol. 21c, 112-120.
6. Iwano, S., Sugiyama, M., Hama, H., Watakabe, A., Hasegawa, N., Kuchimaru, T., Tanaka, K. Z., Takahashi, M., Ishida, Y., Hata, J., Shimozono, S., Namiki, K., Fukano, T., Kiyama, M., Okano, H., Kizaka-Kondoh, S., McHugh, T. J., Yamamori, T., Hioki, H., Maki, S., and Miyawaki, A. (2018) Single-cell bioluminescence imaging of deep tissue in freely moving animals, Science 359, 935-939.
7. Yeh, H. W., Karmach, O., Ji, A., Carter, D., Martins-Green, M. M., and Ai, H. W. (2017) Red-shifted luciferase-luciferin pairs for enhanced bioluminescence imaging, Nat. Methods 14, 971-974.
8. Yeh, H. W., Wu, T., Chen, M., and Ai, H. (2019) Identification of Factors Complicating Bioluminescence Imaging, Biochemistry minor revision as of 02/01/2019, reprint from BioRxiv: https://doi.org/10.1101/511501.
9. Saito, R., Kuchimaru, T., Higashi, S., Lu, S. W., Kiyama, M., Iwano, S., Obata, R., Hirano, T., Kizaka-Kondoh, S., and Maki, S. A. (2018) Synthesis and luminescence properties of near-infrared N-heterocyclic luciferin analogues for in vivo optical imaging, B Chem Soc Jpn. doi:10.1246/bcsj.20180350.
10. Haddock, S. H., Moline, M. A., and Case, J. F. (2010) Bioluminescence in the sea, Ann Rev Mar Sci 2, 443-493.
11. Inouye, S., and Sasaki, S. (2007) Overexpression, purification and characterization of the catalytic component of Oplophorus luciferase in the deep-sea shrimp, Oplophorus gracilirostris, Protein Expr. Purif. 56, 261-268.
12. Hall, M. P., Unch, J., Binkowski, B. F., Valley, M. P., Butler, B. L., Wood, M. G., Otto, P., Zimmerman, K., Vidugiris, G., Machleidt, T., Robers, M. B., Benink, H. A., Eggers, C. T., Slater, M. R., Meisenheimer, P. L., Klaubert, D. H., Fan, F., Encell, L. P., and Wood, K. V. (2012)

Engineered luciferase reporter from a deep sea shrimp utilizing a novel imidazopyrazinone substrate, ACS Chem. Biol. 7, 1848-1857.
13. Weissleder, R., and Ntziachristos, V. (2003) Shedding light onto live molecular targets, Nat. Med. 9, 123-128.
14. Chu, J., Oh, Y, Sens, A., Ataie, N., Dana, H., Macklin, J. J., Laviv, T., Welf, E. S., Dean, K. M., Zhang, F., Kim, B. B., Tang, C. T., Hu, M., Baird, M. A., Davidson, M. W., Kay, M. A., Fiolka, R., Yasuda, R., Kim, D. S., Ng, H. L., and Lin, M. Z. (2016) A bright cyan-excitable orange fluorescent protein facilitates dual-emission microscopy and enhances bioluminescence imaging in vivo, Nat. Biotechnol. 34, 760-767.
15. Suzuki, K., Kimura, T., Shinoda, H., Bai, G., Daniels, M. J., Arai, Y., Nakano, M., and Nagai, T. (2016) Five colour variants of bright luminescent protein for real-time multicolour bioimaging, Nat. Commun. 7, 13718.
16. Teranishi, K., and Shimomura, O. (1997) Solubilizing coelenterazine in water with hydroxypropyl-beta-cyclodextrin, Biosci. Biotechnol. Biochem. 61, 1219-1220.
17. Morse, D., and Tannous, B. A. (2012) A water-soluble coelenterazine for sensitive in vivo imaging of coelenterate luciferases, Mol. Ther. 20, 692-693.
18. Shakhmin, A., Hall, M. P., Machleidt, T., Walker, J. R., Wood, K. V., and Kirkland, T. A. (2017) Coelenterazine analogues emit red-shifted bioluminescence with NanoLuc, Org Biomol Chem. 15, 8559-8567.
19. Shakhmin, A., Hall, M. P., Walker, J. R., Machleidt, T., Binkowski, B. F., Wood, K. V., and Kirkland, T. A. (2016) Three Efficient Methods for Preparation of Coelenterazine Analogues, Chem-Eur J 22, 10369-10375.
20. Jedinak, L., Zatopkova, R., Zemankova, H., Sustkova, A., and Cankar, P. (2017) The Suzuki-Miyaura Cross-Coupling Reaction of Halogenated Aminopyrazoles: Method Development, Scope, and Mechanism of Dehalogenation Side Reaction, J. Org. Chem. 82, 157-169.
21. Adamczyk, M., Akireddy, S. R., Johnson, D. D., Mattingly, P. G., Pan, Y., and Reddy, R. E. (2003) Synthesis of 3,7-dihydroimidazo[1,2a]pyrazine-3-ones and their chemiluminescent properties, Tetrahedron 59, 8129-8142.
22. Kerns, E. H., Di, L., and Carter, G. T. (2008) In vitro solubility assays in drug discovery, Curr. Drug Metab. 9, 879-885.
23. Yeh, H. W., and Ai, H. W. (2019) Development and Applications of Bioluminescent and Chemiluminescent Reporters and Biosensors, Annu. Rev. Anal. Chem. 12, DOI: 10.1146/annurev-anchem-061318-115027.
24. Rogers, K. L., Picaud, S., Roncali, E., Boisgard, R., Colasante, C., Stinnakre, J., Tavitian, B., and Brulet, P. (2007) Non-invasive in vivo imaging of calcium signaling in mice, PLoS One 2, e974.
25. Zinn, K. R., Chaudhuri, T. R., Szafran, A. A., O'Quinn, D., Weaver, C., Dugger, K., Lamar, D., Kesterson, R. A., Wang, X., and Frank, S. J. (2008) Noninvasive bioluminescence imaging in small animals, ILAR J. 49, 103-115.
26. Inouye, S., Sato, J., Sahara-Miura, Y., Yoshida, S., and Hosoya, T. (2014) Luminescence enhancement of the catalytic 19 kDa protein (KAZ) of Oplophorus luciferase by three amino acid substitutions, Biochem. Biophys. Res. Commun. 445, 157-162.
27. Tantama, M., Martinez-Francois, J. R., Mongeon, R., and Yellen, G. (2013) Imaging energy status in live cells with a fluorescent biosensor of the intracellular ATP-to-ADP ratio, Nat. Commun. 4, 2550.
28. Morton, C. L., and Houghton, P. J. (2007) Establishment of human tumor xenografts in immunodeficient mice, Nat. Protoc. 2, 247-250.
29. Bindels, D. S., Haarbosch, L., van Weeren, L., Postma, M., Wiese, K. E., Mastop, M., Aumonier, S., Gotthard, G., Royant, A., Hink, M. A., and Gadella, T. W., Jr. (2017) mScarlet: a bright monomeric red fluorescent protein for cellular imaging, Nat. Methods 14, 53-56.
30. Salin, K., Auer, S. K., Rey, B., Selman, C., and Metcalfe, N. B. (2015) Variation in the link between oxygen consumption and ATP production, and its relevance for animal performance, P Roy Soc B-Biol Sci 282, 14-22.
31. Greenwald, E. C., Mehta, S., and Zhang, J. (2018) Genetically Encoded Fluorescent Biosensors Illuminate the Spatiotemporal Regulation of Signaling Networks, Chemical reviews 118, 11707-11794.
32. Chu, J., Oh, Y., Sens, A., Ataie, N., Dana, H., Macklin, J. J., Laviv, T., Welf, E. S., Dean, K. M., Zhang, F., Kim, B. B., Tang, C. T., Hu, M., Baird, M. A., Davidson, M. W., Kay, M. A., Fiolka, R., Yasuda, R., Kim, D. S., Ng, H. L., and Lin, M. Z. (2016) A bright cyan-excitable orange fluorescent protein facilitates dual-emission microscopy and enhances bioluminescence imaging in vivo, *Nat. Biotechnol.* 34, 760-767.
33. Yeh, H. W., Karmach, O., Ji, A., Carter, D., Martins-Green, M. M., and Ai, H. W. (2017) Red-shifted luciferase-luciferin pairs for enhanced bioluminescence imaging, *Nat. Methods* 14, 971-974.
34. Suzuki, K., Kimura, T., Shinoda, H., Bai, G., Daniels, M. J., Arai, Y., Nakano, M., and Nagai, T. (2016) Five colour variants of bright luminescent protein for real-time multicolour bioimaging, *Nat. Commun.* 7, 13718.
35. Jiang, T. Y., Yang, X. Y., Zhou, Y. B., Yampolsky, I., Du, L. P., and Li, M. Y. (2017) New bioluminescent coelenterazine derivatives with various C-6 substitutions, *Org. Biomol. Chem.* 15, 7008-7018.
36. Adamczyk, M., Akireddy, S. R., Johnson, D. D., Mattingly, P. G., Pan, Y., and Reddy, R. E. (2003) Synthesis of 3,7-dihydroimidazo[1,2a]pyrazine-3-ones and their chemiluminescent properties, *Tetrahedron* 59, 8129-8142.
37. Suzuki, K.; Nagai, *T. Curr Opin Biotech* 2017, 48, 135-141.
38. Yeh, H.-W.; Ai, H.-W. *Annual Review of Analytical Chemistry* 2019. https://doi.org/10.1146/annurev-anchem-061318-115027
39. Naylor, L. H. *Biochem Pharmacol* 1999, 58, 749-757.
40. Miraglia, L. J.; King, F. J.; Damoiseaux, R. *Comb Chem High Throughput Screen* 2011, 14, 648-657.
41. Ohmiya, Y. *Comb Chem High Throughput Screen* 2015, 18, 937-945.
42. Michelini, E.; Cevenini, L.; Mezzanotte, L.; Coppa, A.; Roda, A. *Anal Bioanal Chem* 2010, 398, 227-238.
43. Thorne, N.; Inglese, J.; Auldl, D. S. *Chemistry & Biology* 2010, 17, 646-657.
44. Michelini, E.; Cevenini, L.; Mezzanotte, L.; Ablamsky, D.; Southworth, T.; Branchini, B.; Roda, A. *Anal Chem* 2008, 80, 260-267.
45. Rathbun, C. M.; Porterfield, W. B.; Jones, K. A.; Sagoe, M. J.; Reyes, M. R.; Hua, C. T.; Prescher, J. A. *ACS Cent Sci* 2017, 3, 1254-1261.
46. Jones, K. A.; Porterfield, W. B.; Rathbun, C. M.; McCutcheon, D. C.; Paley, M. A.; Prescher, J. A. *Journal of the American Chemical Society* 2017. 139, 2351-2358.
47. Heise, K.; Oppermann, H.; Meixensberger, J.; Gebhardt, R.; Gaunitz, F. *Assay Drug Dev Techn* 2013, 11, 244-252.
48. Mezzanotte, L.; Que, I.; Kaijzel, E.; Branchini, B.; Roda, A.; Lowik, C. *Plos One* 2011, 6, e19277.
49. Yasunaga, M.; Nakajima, Y.; Ohmiya, Y. *Anal Bioanal Chem* 2014, 406, 5735-5742.

50. Mezzanotte, L.; An, N.; Mol, I. M.; Lowik, C. W.; Kaijzel, E. L. *Plos One* 2014, 9, e85550.

51. Nakajima, Y.; Kimura, T.; Sugata, K.; Enomoto, T.; Asakawa, A.; Kubota, H.; Ikeda, M.; Ohmiya, Y. *Biotechniques* 2005, 38, 891-894.

52. Branchini, B. R.; Southworth, T. L.; Fontaine, D. M.; Kohrt, D.; Florentine, C. M.; Grossel, M. J. *Sci Rep-Uk* 2018, 8.

53. Yeh, H. W.; Karmach, O.; Ji, A.; Carter, D.; Martins-Green, M. M.; Ai, H. W. *Nat Methods* 2017, 14, 971-974.

54. Loening, A. M.; Wu, A. M.; Gambhir, S. S. *Nat Methods* 2007, 4, 641-643.

55. Rumyantsev, K. A.; Turoverov, K. K.; Verkhusha, V. V. *Sci Rep-Uk* 2016, 6, 36588.

56. Wu, C.; Nakamura, H.; Murai, A.; Shimomura, O. *Tetrahedron Lett* 2001, 42, 2997-3000.

57. Iwano, S.; Sugiyama, M.; Hama, H.; Watakabe, A.; Hasegawa, N.; Kuchimaru, T.; Tanaka, K. Z.; Takahashi, M.; Ishida, Y.; Hata, J.; Shimozono, S.; Namiki, K.; Fukano, T.; Kiyama, M.; Okano, H.; Kizaka-Kondoh, S.; McHugh, T. J.; Yamamori, T.; Hioki, H.; Maki, S., et al. *Science* 2018, 359, 935-939.

58. Hill, C. S.; Treisman, R. *Embo J* 1995, 14, 5037-5047.

59. Nguyen, T.; Nioi, P.; Pickett, C. B. *J Biol Chem* 2009, 284, 13291-13295.

60. Badr, C. E.; Niers, J. M.; Tjon-Kon-Fat, L. A.; Noske, D. P.; Wurdinger, T.; Tannous, B. A. *Molecular Imaging* 2009, 8, 278-290.

61. Kotlobay, A. A.; Sarkisyan, K. S.; Mokrushina, Y. A.; Marcet-Houben, M.; Serebrovskaya, E. O.; Markina, N. M.; Gonzalez Somermeyer, L.; Gorokhovatsky, A. Y.; Vvedensky, A.; Purtov, K. V.; Petushkov, V. N.; Rodionova, N. S.; Chepurnyh, T. V.; Fakhranurova, L. I.; Guglya, E. B.; Ziganshin, R.; Tsarkova, A. S.; Kaskova, Z. M.; Shender, V.; Abakumov, M., et al. *Proceedings of the National Academy ofSciences of the United States of America* 2018, 115, 12728-12732.

62. Greenwald, E. C.; Mehta, S.; Zhang, J. *Chemical reviews* 2018, 118, 11707-11794.

63. Yeh, H. W., Karmach, O., Ji, A., Carter, D., Martins-Green, M. M., and Ai, H. W. (2017) Red-shifted luciferase-luciferin pairs for enhanced bioluminescence imaging, *Nat Methods* 14, 971-974.

64. Adamczyk, M., Akireddy, S. R., Johnson, D. D., Mattingly, P. G., Pan, Y., and Reddy, R. E. (2003) Synthesis of 3,7-dihydroimidazo[1,2a]pyrazine-3-ones and their chemiluminescent properties, *Tetrahedron* 59, 8129-8142.

65. Suzuki, K.; Kimura, T.; Shinoda, H.; Bai, G.; Daniels, M. J.; Arai, Y.; Nakano, M.; Nagai, T. Five colour variants of bright luminescent protein for real-time multicolour bioimaging. *Nat. Commun.* 2016, 7, 13718.

66. Qian, Y.; Rancic, V.; Wu, J.; Ballanyi, K.; Campbell, R. E. A Bioluminescent Ca(2+) Indicator Based on a Topological Variant of GCaMP6s. *ChemBioChem* 2018.

67. Inagaki, S.; Tsutsui, H.; Suzuki, K.; Agetsuma, M.; Arai, Y.; Jinno, Y.; Bai, G.; Daniels, M. J.; Okamura, Y.; Matsuda, T. et al. Genetically encoded bioluminescent voltage indicator for multi-purpose use in wide range of bioimaging. *Scientific reports* 2017, 7, 42398.

68. Oh, Y.; Park, Y.; Cho, J. H.; Wu, H.; Paulk, N. K.; Liu, L. X.; Kim, N.; Kay, M. A.; Wu, J. C.; Lin, M. Z. An orange calcium-modulated bioluminescent indicator for non-invasive activity imaging. *Nat Chem Biol* 2019, 15 (5), 433.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A bioluminescent proteins comprising; an amino acid sequence selected from the group consisting of: an amino acid sequence at least 96% identical to SEQ ID NO: 6; an amino acid sequence at least 96% identical to SEQ ID NO: 8; an amino acid sequence at least 96% identical to SEQ ID NO: 10; and an amino acid sequence at least 96% identical to SEQ ID NO: 12; wherein the bioluminescent protein maintains bioluminescent activity.

2. A bioluminescent protein, comprising: a substituted luciferase polypeptide; and, a fluorescent protein connected to the substituted luciferase polypeptide; wherein said substituted luciferase polypeptide is selected from the group consisting of, comprises an amino acid sequence at least 92% identical to SEQ ID NO: 2; an amino acid sequence wherein the substituted luciferase has four individual amino acid substitutions at positions corresponding to positions 20, 21, 29, and 30 of SEQ ID NO: 2; an amino acid sequence wherein the substituted luciferase has at least one additional amino acid substitution from positions consisting of: 6, 69, 73, 87, 92, 114, 121, and 138 of SEQ ID NO: 2; and, an amino acid sequence wherein the substituted luciferase polypeptide exhibits bioluminescence in the presence of a substrate; wherein the substituted luciferase polypeptide comprises the amino acid sequence of SEQ ID NO: 5.

* * * * *

SEQUENCE LISTING

```
<160> NUMBER OF SEQ ID NOS: 45

<210> SEQ ID NO 1
<211> LENGTH: 171
<212> TYPE: PRT
<213> ORGANISM: Artificial Sequence
<220> FEATURE:
<223> OTHER INFORMATION: Artificially mutated luciferase polypeptide

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
```

-continued

```
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170


<210> SEQ ID NO 2
<211> LENGTH: 171
<212> TYPE: PRT
<213> ORGANISM: Artificial Sequence
<220> FEATURE:
<223> OTHER INFORMATION: Artificially mutated luciferase polypeptide

<400> SEQUENCE: 2

Met Val Phe Thr Leu Glu Asp Phe Val Gly Asp Trp Arg Gln Thr Ala
1               5                   10                  15

Gly Tyr Asn Leu Ser Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asn His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu His Glu Arg Ile Leu Ala
                165                 170


<210> SEQ ID NO 3
<211> LENGTH: 171
<212> TYPE: PRT
<213> ORGANISM: Artificial Sequence
<220> FEATURE:
<223> OTHER INFORMATION: Artificially mutated luciferase polypeptide

<400> SEQUENCE: 3

Lys Val Phe Thr Leu Gly Asp Phe Val Gly Asp Trp Arg Gln Thr Ala
1               5                   10                  15

Gly Tyr Asn Gln Ala Gln Val Leu Glu Gln Gly Gly Leu Thr Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Cys Asp Gln Met Ala Gln Ile Glu Lys Ile Phe Lys
65                  70                  75                  80
```

-continued

```
Val Val Tyr Pro Val Asp Asp His His Phe Lys Ala Ile Leu His Tyr
                85                  90                  95

Gly Thr Leu Val Ile Asp Gly Val Thr Pro Asn Met Ile Asp Tyr Phe
            100                 105                 110

Gly Gln Pro Tyr Glu Gly Ile Ala Lys Phe Asp Gly Lys Lys Ile Thr
        115                 120                 125

Val Thr Gly Thr Leu Trp Asn Gly Asn Thr Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu His Glu Arg Ile Leu Ala
                165                 170
```

<210> SEQ ID NO 4
<211> LENGTH: 1185
<212> TYPE: DNA
<213> ORGANISM: Artificial Sequence
<220> FEATURE:
<223> OTHER INFORMATION: Artificially mutated luciferase oligonucleotide

<400> SEQUENCE: 4

```
atggtgagca agggcgaggc agtgatcaag gagttcatgc ggttcaaggt gcacatggag     60

ggctccatga acggccacga gttcgagatc gagggcgagg gcgagggccg cccctacgag    120

ggcacccaga ccgccaagct gaaggtgacc aagggtggcc ccctgccctt ctcctgggac    180

atcctgtccc ctcagttcat gtacggctcc agggccttca tcaagcaccc cgccgacatc    240

cccgactact ataagcagtc cttccccgag ggcttcaagt gggagcgcgt gatgaacttc    300

gaggacggcg gcgccgtgac cgtgacccag gacacctccc tggaggacgg caccctgatc    360

tacaaggtga agctccgcgg caccaacttc cctcctgacg gccccgtaat gcagaagaag    420

acaatgggct gggaagcgtc caccgagcgg ttgtaccccg aggacggcgt gctgaagggc    480

gacattaaga tggccctgcg cctgaaggac ggcggccgct acctggcgga cttcaagacc    540

acctacaagg ccaagaagcc cgtgcagatg cccggcgcct acaacgtcga ccgcaagttg    600

gacatcacct cccacaacga ggactacacc gtggtggaac agtacgaacg ctccgagggc    660

cgccactcca ccggaaagac tctcggggat tttgttgggg actggcgaca gacagccggc    720

tacaaccagg ctcaagtcct tgaacaggga ggtttgacca gtttgtttca gaacctcggg    780

gtgtccgtaa ctccaatcca aaggattgtc ctgagcggtg aaaatgggct gaagatcgat    840

atccatgtca tcatcccgta tgaaggtctg agctgcgacc aaatggccca gatcgaaaaa    900

atttttaagg tggtataccc tgtggatgat catcacttta aggcgatcct gcactatggc    960

acactggtaa tcgacggggt tacgccgaac atgatcgact atttcggaca gccgtatgaa   1020

ggcatcgcca agttcgacgg caaaaagatc acagtaacag ggaccctgtg gaacggcaac   1080

acaattatcg acgagcgcct gatcaacccc gacggctccc tgctgttccg agtaaccatt   1140

aacggagtga ccggctggcg tctgcatgaa cgcattctgg cgtaa                   1185
```

<210> SEQ ID NO 5
<211> LENGTH: 394
<212> TYPE: PRT
<213> ORGANISM: Artificial Sequence
<220> FEATURE:
<223> OTHER INFORMATION: Artificially mutated luciferase polypeptide

<400> SEQUENCE: 5

```
Met Val Ser Lys Gly Glu Ala Val Ile Lys Glu Phe Met Arg Phe Lys
```

-continued

```
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Ile Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Lys Thr Leu Gly Asp Phe Val Gly Asp Trp Arg Gln Thr Ala Gly
225                 230                 235                 240

Tyr Asn Gln Ala Gln Val Leu Glu Gln Gly Gly Leu Thr Ser Leu Phe
                245                 250                 255

Gln Asn Leu Gly Val Ser Val Thr Pro Ile Gln Arg Ile Val Leu Ser
            260                 265                 270

Gly Glu Asn Gly Leu Lys Ile Asp Ile His Val Ile Ile Pro Tyr Glu
        275                 280                 285

Gly Leu Ser Cys Asp Gln Met Ala Gln Ile Glu Lys Ile Phe Lys Val
    290                 295                 300

Val Tyr Pro Val Asp Asp His His Phe Lys Ala Ile Leu His Tyr Gly
305                 310                 315                 320

Thr Leu Val Ile Asp Gly Val Thr Pro Asn Met Ile Asp Tyr Phe Gly
                325                 330                 335

Gln Pro Tyr Glu Gly Ile Ala Lys Phe Asp Gly Lys Lys Ile Thr Val
            340                 345                 350

Thr Gly Thr Leu Trp Asn Gly Asn Thr Ile Ile Asp Glu Arg Leu Ile
        355                 360                 365

Asn Pro Asp Gly Ser Leu Leu Phe Arg Val Thr Ile Asn Gly Val Thr
    370                 375                 380

Gly Trp Arg Leu His Glu Arg Ile Leu Ala
385                 390
```

<210> SEQ ID NO 6
<211> LENGTH: 171
<212> TYPE: PRT
<213> ORGANISM: Artificial Sequence -continued
<220> FEATURE:
<223> OTHER INFORMATION: Artificially mutated luciferase polypeptide

<400> SEQUENCE: 6

```
Met Val Phe Thr Leu Glu Asp Phe Val Gly Asp Trp Arg Gln Thr Ala
1               5                   10                  15

Gly Tyr Asn Gln Ala Lys Ala Leu Glu Gln Gly Gly Leu Thr Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Cys Asp Gln Met Ala Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Gln Pro Tyr Glu Gly Ile Ala Lys Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu His Glu Arg Ile Leu Ala
                165                 170
```

<210> SEQ ID NO 7
<211> LENGTH: 1179
<212> TYPE: DNA
<213> ORGANISM: Artificial Sequence
<220> FEATURE:
<223> OTHER INFORMATION: Artificially mutated luciferase oligonucleotide

<400> SEQUENCE: 7

```
atggtgagca agggcgaggc agtgatcaag gagttcatgc ggttcaaggt gcacatggag     60

ggctccatga acggccacga gttcgagatc gagggcgagg gcgagggccg cccctacgag    120

ggcacccaga ccgccaagct gaaggtgacc aagggtggcc ccctgccctt ctcctgggac    180

atcctgtccc ctcagttcat gtacggctcc agggccttca tcaagcaccc cgccgacatc    240

cccgactact ataagcagtc cttccccgag ggcttcaagt gggagcgcgt gatgaacttc    300

gaggacggcg gcgccgtgac cgtgacccag gacacctccc tggaggacgg caccctgatc    360

tacaaggtga agctccgcgg caccaacttc cctcctgacg gccccgtaat gcagaagaag    420

acaatgggct gggaagcgtc caccgagcgg ttgtaccccg aggacggcgt gctgaagggc    480

gacattaaga tggccctgcg cctgaaggac ggcggccgct acctggcgga cttcaagacc    540

acctacaagg ccaagaagcc cgtgcagatg cccggcgcct acaacgtcga ccgcaagttg    600

gacatcacct cccacaacga ggactacacc gtggtggaac agtacgaacg ctccgagggc    660

cgccatcttg atacactcga agatttcgtt ggggactggc gacagacagc cggctacaac    720

ttgagtcaag tccttgaaca gggaggtgtg tccagtttgt ttcagaatct cggggtgtcc    780

gtaactccga tccaaaggat tgtcctgagc ggtgaaaatg ggctgaagat cgacatccat    840

gtcatcatcc cgtatgaagg tctgagcggc gaccaaatgg gccagatcga aaaaattttt    900

aaggtggtgt accctgtgga taatcatcac tttaaggtga tcctgcacta tggcacactg    960
```

```
gtaatcgacg gggttacgcc gaacatgatc gactatttcg gacggccgta tgaaggcatc   1020

gccgtgttcg acggcaaaaa gatcactgta acagggaccc tgtggaacgg caacaaaatt   1080

atcgacgagc gcctgatcaa ccccgacggc tccctgctgt tccgagtaac catcaacgga   1140

gtgaccggct ggcgtctgca tgaacgcatt ctggcgtaa                           1179


<210> SEQ ID NO 8
<211> LENGTH: 392
<212> TYPE: PRT
<213> ORGANISM: Artificial Sequence
<220> FEATURE:
<223> OTHER INFORMATION: Artificially mutated luciferase polypeptide

<400> SEQUENCE: 8

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Ile Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Leu Asp
    210                 215                 220

Thr Leu Glu Asp Phe Val Gly Asp Trp Arg Gln Thr Ala Gly Tyr Asn
225                 230                 235                 240

Leu Ser Gln Val Leu Glu Gln Gly Gly Val Ser Ser Leu Phe Gln Asn
                245                 250                 255

Leu Gly Val Ser Val Thr Pro Ile Gln Arg Ile Val Leu Ser Gly Glu
            260                 265                 270

Asn Gly Leu Lys Ile Asp Ile His Val Ile Ile Pro Tyr Glu Gly Leu
        275                 280                 285

Ser Gly Asp Gln Met Gly Gln Ile Glu Lys Ile Phe Lys Val Val Tyr
    290                 295                 300

Pro Val Asp Asn His His Phe Lys Val Ile Leu His Tyr Gly Thr Leu
305                 310                 315                 320
```

-continued

```
Val Ile Asp Gly Val Thr Pro Asn Met Ile Asp Tyr Phe Gly Arg Pro
                325                 330                 335

Tyr Glu Gly Ile Ala Val Phe Asp Gly Lys Lys Ile Thr Val Thr Gly
            340                 345                 350

Thr Leu Trp Asn Gly Asn Lys Ile Ile Asp Glu Arg Leu Ile Asn Pro
        355                 360                 365

Asp Gly Ser Leu Leu Phe Arg Val Thr Ile Asn Gly Val Thr Gly Trp
    370                 375                 380

Arg Leu His Glu Arg Ile Leu Ala
385                 390
```

<210> SEQ ID NO 9
<211> LENGTH: 1962
<212> TYPE: DNA
<213> ORGANISM: Artificial Sequence
<220> FEATURE:
<223> OTHER INFORMATION: Artificially mutated luciferase oligonucleotide

<400> SEQUENCE: 9

```
atggtgagca agggcgaggc agtgatcaag gagttcatgc ggttcaaggt gcacatggag     60

ggctccatga acggccacga gttcgagatc gagggcgagg gcgagggccg cccctacgag    120

ggcacccaga ccgccaagct gaaggtgacc aagggtggcc ccctgccctt ctcctgggac    180

atcctgtccc ctcagttcat gtacggctcc agggccttca tcaagcaccc cgccgacatc    240

cccgactact ataagcagtc cttccccgag ggcttcaagt gggagcgcgt gatgaacttc    300

gaggacggcg gcgccgtgac cgtgacccag gacacctccc tggaggacgg caccctgatc    360

tacaaggtga agctccgcgg caccaacttc cctcctgacg gccccgtaat gcagaagaag    420

acaatgggct gggaagcgtc caccgagcgg ttgtaccccg aggacggcgt gctgaagggc    480

gacattaaga tggccctgcg cctgaaggac ggcggccgct acctggcgga cttcaagacc    540

acctacaagg ccaagaagcc cgtgcagatg cccggcgcct acaacgtcga ccgcaggttg    600

gacatcacct cccacaacga ggactacacc gtggtggaac agtacgaacg ctccgagggc    660

cgcaagcgtc aagatgctag cgaagaagag ctatcagagt gctttcgcgt ttttgacaag    720

gatggaaatg gtttcatcga cagggaggaa tttggagaca tcatccgcct tactggagaa    780

cagctcacgg atgaggatcc cgatgagata tttggagatt cagacacaga caaaaatgga    840

aggattgact ttgatgagtt cctgaagatg gtggagaatg tccagtatgt taatattctc    900

aaagtcttca ctctcgggga ttttgttggg gactggcgac agacagccgg ctacaaccag    960

gctcaagtcc ttgaacaggg aggtttgacc agtttgtttc agaacctcgg ggtgtccgta   1020

actccaatcc aaaggattgt cctgagcggt gaaaatgggc tgaagatcga tatccatgtc   1080

atcatcccgt atgaaggtct gagctgcgac caaatggccc agatcgaaaa aatttttaag   1140

gtggtatacc ctgtggatga tcatcacttt aaggcgatcc tgcactatgg cacactggta   1200

atcgacgggg ttacgccgaa catgatcgac tatttcggac agccgtatga aggcatcgcc   1260

aagttcgacg gcaaaaagat cacagtaaca gggaccctga taatgcatga ccaactgaca   1320

gaagagcaga ttgcagagtt caaagaagcc ttctcattat tcgacaagga tggggacggc   1380

accatcacca caaaggaact tggcaccgtt atgaggtcgc ttggacaaaa cccaacggaa   1440

gcagaattgc aggatatgat caatgaagtc gatgctgatg gcaatggaac gatttacttt   1500

cctgaatttc ttactatgat ggctagaaaa atgaaggaca cagacagcga agaggaaatc   1560

cgagaagcat tccgtgtttt tgacaaggat gggaacggct acatcagcgc tgctcagtta   1620
```

-continued

```
cgtcacgtca tgacaaacct cggggagaag ttaacagatg aagaagttga tgaaatgata   1680

agggaagcag atatcgatgg tgatggccaa gtaaactatg aagagtttgt acaaatgatg   1740

acagcaaagg ggggcgggtc caagaggcgc tggaagaaaa acttcattgc cgtcagcgct   1800

gccaaccggt tcaagaagat ctccagctcc ggggcactgg agctttggaa cggcaacaca   1860

attatcgacg agcgcctgat caacccgac ggctccctgc tgttccgagt aaccattaac   1920

ggagtgaccg gctggcgtct gcatgaacgc attctggcgt aa                      1962


<210> SEQ ID NO 10
<211> LENGTH: 653
<212> TYPE: PRT
<213> ORGANISM: Artificial Sequence
<220> FEATURE:
<223> OTHER INFORMATION: Artificially mutated luciferase polypeptide

<400> SEQUENCE: 10

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Ile Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Arg Leu Asp Ile Thr Ser His Asn Glu Asp
        195                 200                 205

Tyr Thr Val Val Glu Gln Tyr Glu Arg Ser Glu Gly Arg Lys Arg Gln
    210                 215                 220

Asp Ala Ser Glu Glu Glu Leu Ser Glu Cys Phe Arg Val Phe Asp Lys
225                 230                 235                 240

Asp Gly Asn Gly Phe Ile Asp Arg Glu Glu Phe Gly Asp Ile Ile Arg
                245                 250                 255

Leu Thr Gly Glu Gln Leu Thr Asp Glu Asp Pro Asp Glu Ile Phe Gly
            260                 265                 270

Asp Ser Asp Thr Asp Lys Asn Gly Arg Ile Asp Phe Asp Glu Phe Leu
        275                 280                 285

Lys Met Val Glu Asn Val Gln Tyr Val Asn Ile Leu Lys Val Phe Thr
    290                 295                 300
```

-continued

```
Leu Gly Asp Phe Val Gly Asp Trp Arg Gln Thr Ala Gly Tyr Asn Gln
305                 310                 315                 320

Ala Gln Val Leu Glu Gln Gly Gly Leu Thr Ser Leu Phe Gln Asn Leu
                325                 330                 335

Gly Val Ser Val Thr Pro Ile Gln Arg Ile Val Leu Ser Gly Glu Asn
            340                 345                 350

Gly Leu Lys Ile Asp Ile His Val Ile Ile Pro Tyr Glu Gly Leu Ser
        355                 360                 365

Cys Asp Gln Met Ala Gln Ile Glu Lys Ile Phe Lys Val Val Tyr Pro
    370                 375                 380

Val Asp Asp His His Phe Lys Ala Ile Leu His Tyr Gly Thr Leu Val
385                 390                 395                 400

Ile Asp Gly Val Thr Pro Asn Met Ile Asp Tyr Phe Gly Gln Pro Tyr
                405                 410                 415

Glu Gly Ile Ala Lys Phe Asp Gly Lys Lys Ile Thr Val Thr Gly Thr
            420                 425                 430

Leu Ile Met His Asp Gln Leu Thr Glu Glu Gln Ile Ala Glu Phe Lys
        435                 440                 445

Glu Ala Phe Ser Leu Phe Asp Lys Asp Gly Asp Gly Thr Ile Thr Thr
    450                 455                 460

Lys Glu Leu Gly Thr Val Met Arg Ser Leu Gly Gln Asn Pro Thr Glu
465                 470                 475                 480

Ala Glu Leu Gln Asp Met Ile Asn Glu Val Asp Ala Asp Gly Asn Gly
                485                 490                 495

Thr Ile Tyr Phe Pro Glu Phe Leu Thr Met Met Ala Arg Lys Met Lys
            500                 505                 510

Asp Thr Asp Ser Glu Glu Glu Ile Arg Glu Ala Phe Arg Val Phe Asp
        515                 520                 525

Lys Asp Gly Asn Gly Tyr Ile Ser Ala Ala Gln Leu Arg His Val Met
    530                 535                 540

Thr Asn Leu Gly Glu Lys Leu Thr Asp Glu Glu Val Asp Glu Met Ile
545                 550                 555                 560

Arg Glu Ala Asp Ile Asp Gly Asp Gly Gln Val Asn Tyr Glu Glu Phe
                565                 570                 575

Val Gln Met Met Thr Ala Lys Gly Gly Gly Ser Lys Arg Arg Trp Lys
            580                 585                 590

Lys Asn Phe Ile Ala Val Ser Ala Ala Asn Arg Phe Lys Lys Ile Ser
        595                 600                 605

Ser Ser Gly Ala Leu Glu Leu Trp Asn Gly Asn Thr Ile Ile Asp Glu
    610                 615                 620

Arg Leu Ile Asn Pro Asp Gly Ser Leu Leu Phe Arg Val Thr Ile Asn
625                 630                 635                 640

Gly Val Thr Gly Trp Arg Leu His Glu Arg Ile Leu Ala
                645                 650
```

<210> SEQ ID NO 11
<211> LENGTH: 1962
<212> TYPE: DNA
<213> ORGANISM: Artificial Sequence
<220> FEATURE:
<223> OTHER INFORMATION: Artificially mutated luciferase oligonucleotide

<400> SEQUENCE: 11

```
atggtgagca agggcgaggc agtgatcaag gagttcatgc ggttcaaggt gcacatggag     60

ggctccatga acggccacga gttcgagatc gagggcgagg gcgagggccg cccctacgag    120
```

```
ggcacccaga ccgccaagct gaaggtgacc aagggtggcc ccctgccctt ctcctgggac    180
atcctgtccc ctcagttcat gtacggctcc agggccttca tcaagcaccc cgccgacatc    240
cccgactact ataagcagtc cttccccgag ggcttcaagt gggagcgcgt gatgaacttc    300
gaggacggcg gcgccgtgac cgtgacccag gacacctccc tggaggacgg caccctgatc    360
tacaaggtga agctccgcgg caccaacttc cctcctgacg gccccgtaat gcagaagaag    420
acaatgggct gggaagcgtc caccgagcgg ttgtaccccg aggacggcgt gctgaagggc    480
gacattaaga tggccctgcg cctgaaggac ggcggccgct acctggcgga cttcaagacc    540
acctacaagg ccaagaagcc cgtgcagatg cccggcgcct acaacgtcga ccgcaggttg    600
gacatcacct cccacaacga ggactacacc gtggtggaac agtacgaacg ctccgagggc    660
cgcaagcgtc aagatgctag cgaagaagag ctatcagagt gctttcgcgt ttttgacaag    720
gatggaaatg gtttcatcga cagggaggaa tttggagaca tcatccgcct tactggagaa    780
cagctcacgg atgaggatcc cgatgagata tttggagatt cagacacaga caaaaatgga    840
aggattgact ttgatgagtt cctgaagatg gtggagaatg tccagtatgt taatattctc    900
atggtcttca cactcgaaga tttcgttggg gactggcgac agacagccgg ctacaacttg    960
agtcaagtcc ttgaacaggg aggtgtgtcc agtttgtttc agaatctcgg ggtgtccgta   1020
actccgatcc aaaggattgt cctgagcggt gaaaatgggc tgaagatcga catccatgtc   1080
atcatcccgt atgaaggtct gagcggcgac caaatgggcc agatcgaaaa aatttttaag   1140
gtggtgtacc ctgtggataa tcatcacttt aaggtgatcc tgcactatgg cacactggta   1200
atcgacgggg ttacgccgaa catgatcgac tatttcggac ggccgtatga aggcatcgcc   1260
gtgttcgacg gcaaaaagat cactgtaaca gggaccctga taatgcatga ccaactgaca   1320
gaagagcaga ttgcagagtt caaagaagcc ttctcattat tcgacaagga tggggacggc   1380
accatcacca caaaggaact tggcaccgtt atgaggtcgc ttggacaaaa cccaacggaa   1440
gcagaattgc aggatatgat caatgaagtc gatgctgatg gcaatggaac gatttacttt   1500
cctgaatttc ttactatgat ggctagaaaa atgaaggaca cagacagcga agaggaaatc   1560
cgagaagcat tccgtgtttt tgacaaggat gggaacggct acatcagcgc tgctcagtta   1620
cgtcacgtca tgacaaacct cggggagaag ttaacagatg aagaagttga tgaaatgata   1680
agggaagcag atatcgatgg tgatggccaa gtaaactatg aagagtttgt acaaatgatg   1740
acagcaaagg ggggcgggtc caagaggcgc tggaagaaaa acttcattgc cgtcagcgct   1800
gccaaccggt tcaagaagat ctccagctcc ggggcactgg agctttggaa cggcaacaaa   1860
attatcgacg agcgcctgat caaccccgac ggctccctgc tgttccgagt aaccatcaac   1920
ggagtgaccg gctggcgtct gcatgaacgc attctggcgt aa                      1962
```

<210> SEQ ID NO 12
<211> LENGTH: 653
<212> TYPE: PRT
<213> ORGANISM: Artificial Sequence
<220> FEATURE:
<223> OTHER INFORMATION: Artificially mutated luciferase polypeptide

<400> SEQUENCE: 12

```
Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30
```

-continued

```
Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Ile Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Arg Leu Asp Ile Thr Ser His Asn Glu Asp
        195                 200                 205

Tyr Thr Val Val Glu Gln Tyr Glu Arg Ser Glu Gly Arg Lys Arg Gln
    210                 215                 220

Asp Ala Ser Glu Glu Glu Leu Ser Glu Cys Phe Arg Val Phe Asp Lys
225                 230                 235                 240

Asp Gly Asn Gly Phe Ile Asp Arg Glu Glu Phe Gly Asp Ile Ile Arg
                245                 250                 255

Leu Thr Gly Glu Gln Leu Thr Asp Glu Asp Pro Asp Glu Ile Phe Gly
            260                 265                 270

Asp Ser Asp Thr Asp Lys Asn Gly Arg Ile Asp Phe Asp Glu Phe Leu
        275                 280                 285

Lys Met Val Glu Asn Val Gln Tyr Val Asn Ile Leu Met Val Phe Thr
    290                 295                 300

Leu Glu Asp Phe Val Gly Asp Trp Arg Gln Thr Ala Gly Tyr Asn Leu
305                 310                 315                 320

Ser Gln Val Leu Glu Gln Gly Gly Val Ser Ser Leu Phe Gln Asn Leu
                325                 330                 335

Gly Val Ser Val Thr Pro Ile Gln Arg Ile Val Leu Ser Gly Glu Asn
            340                 345                 350

Gly Leu Lys Ile Asp Ile His Val Ile Ile Pro Tyr Glu Gly Leu Ser
        355                 360                 365

Gly Asp Gln Met Gly Gln Ile Glu Lys Ile Phe Lys Val Val Tyr Pro
    370                 375                 380

Val Asp Asn His His Phe Lys Val Ile Leu His Tyr Gly Thr Leu Val
385                 390                 395                 400

Ile Asp Gly Val Thr Pro Asn Met Ile Asp Tyr Phe Gly Arg Pro Tyr
                405                 410                 415

Glu Gly Ile Ala Val Phe Asp Gly Lys Lys Ile Thr Val Thr Gly Thr
            420                 425                 430

Leu Ile Met His Asp Gln Leu Thr Glu Glu Gln Ile Ala Glu Phe Lys
        435                 440                 445

Glu Ala Phe Ser Leu Phe Asp Lys Asp Gly Asp Gly Thr Ile Thr Thr
```

-continued

```
    450                 455                 460

Lys Glu Leu Gly Thr Val Met Arg Ser Leu Gly Gln Asn Pro Thr Glu
465                 470                 475                 480

Ala Glu Leu Gln Asp Met Ile Asn Glu Val Asp Ala Asp Gly Asn Gly
                485                 490                 495

Thr Ile Tyr Phe Pro Glu Phe Leu Thr Met Met Ala Arg Lys Met Lys
            500                 505                 510

Asp Thr Asp Ser Glu Glu Glu Ile Arg Glu Ala Phe Arg Val Phe Asp
        515                 520                 525

Lys Asp Gly Asn Gly Tyr Ile Ser Ala Ala Gln Leu Arg His Val Met
    530                 535                 540

Thr Asn Leu Gly Glu Lys Leu Thr Asp Glu Glu Val Asp Glu Met Ile
545                 550                 555                 560

Arg Glu Ala Asp Ile Asp Gly Asp Gly Gln Val Asn Tyr Glu Glu Phe
                565                 570                 575

Val Gln Met Met Thr Ala Lys Gly Gly Gly Ser Lys Arg Arg Trp Lys
            580                 585                 590

Lys Asn Phe Ile Ala Val Ser Ala Ala Asn Arg Phe Lys Lys Ile Ser
        595                 600                 605

Ser Ser Gly Ala Leu Glu Leu Trp Asn Gly Asn Lys Ile Ile Asp Glu
    610                 615                 620

Arg Leu Ile Asn Pro Asp Gly Ser Leu Leu Phe Arg Val Thr Ile Asn
625                 630                 635                 640

Gly Val Thr Gly Trp Arg Leu His Glu Arg Ile Leu Ala
                645                 650


<210> SEQ ID NO 13
<211> LENGTH: 936
<212> TYPE: DNA
<213> ORGANISM: Artificial Sequence
<220> FEATURE:
<223> OTHER INFORMATION: Artificially mutated luciferase oligonucleotide

<400> SEQUENCE: 13

atggcttcca aggtgtacga ccccgagcaa cgcaaacgca tgatcactgg gcctcagtgg      60

tgggctcgct gcaagcaaat gaacgtgctg gactccttca tcaactacta tgattccgag     120

aagcacgccg agaacgccgt gatttttctg catggtaacg ctacctccag ctacctgtgg     180

aggcacgtcg tgcctcacat cgagcccgtg gctagatgca tcatccctga tctgatcgga     240

atgggtaagt ccggcaagag cgggaatggc tcatatcgcc tcctggatca ctacaagtac     300

ctcaccgctt ggttcgagct gctgaacctt ccaaagaaaa tcatctttgt gggccacgac     360

tggggggctg ctctggcctt tcactacgcc tacgagcacc aagacaggat caaggccatc     420

gtccatatgg agagtgtcgt ggacgtgatc gagtcctggg acgagtggcc tgacatcgag     480

gaggatatcg ccctgatcaa gagcgaagag ggcgagaaaa tggtgcttga gaataacttc     540

ttcgtcgaga ccgtgctccc aagcaagatc atgcggaaac tggagcctga ggagttcgct     600

gcctacctgg agccattcaa ggagaagggc gaggttagac ggcctaccct ctcctggcct     660

cgcgagatcc ctctcgttaa gggaggcaag cccgacgtcg tccagattgt ccgcaactac     720

aacgcctacc ttcgggccag cgacgatctg cctaagctgt tcatcgagtc cgaccctggg     780

ttcttttcca acgctattgt cgagggagct aagaagttcc ctaacaccga gttcgtgaag     840

gtgaagggcc tccacttcct ccaggaggac gctccagatg aaatgggtaa gtacatcaag     900

agcttcgtgg agcgcgtgct gaagaacgag cagtaa                               936
```

<210> SEQ ID NO 14
<211> LENGTH: 311
<212> TYPE: PRT
<213> ORGANISM: Artificial Sequence
<220> FEATURE:
<223> OTHER INFORMATION: Artificially mutated luciferase polypeptide

<400> SEQUENCE: 14

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 15
<211> LENGTH: 1653
<212> TYPE: DNA
<213> ORGANISM: Artificial Sequence
<220> FEATURE:
<223> OTHER INFORMATION: Artificially mutated luciferase oligonucleotide

<400> SEQUENCE: 15
atggaagatg ccaaaaacat taagaagggc ccagcgccgt tctacccact cgaagacggg 60
accgccggcg agcagctgca caaagccatg aagcgctacg ccctggtgcc cggcgccatc 120
gcctttaccg acgcacatat tcaggtggac gttacctacg ccgagtactt cgagatgagc 180
gttcggctgg cagaagctat gaggcgctat gggctgaata caaaccatcg gatcgtggtg 240
tgcagcgaga atagctcgca gttcttcatg cccgtgttgg gtgccctgtt catcggtgtg 300
gctgtggccc cagctaacga catctacaac gagcgcgagc tgctgaacag catgggcatc 360
agccagccca ccgtcgtatt cgtgagcaag aaagggctgc gaaaggtcct caacgtgcaa 420
aagaagctac cgatcatacg aaagatcatc atcatggata gcaagaccga ctaccagggc 480
ttccaaagca tgtacacctt cgtgacttcc catttgccac ccagcttcaa cgagtacgac 540
ttcgtgcccg agagcttcga ccgggacaaa accatcgccc tgatcatgaa cagtagtggt 600
agtacaggat tacccaaggg cgtagcccta ccgcaccgca ccgcttgtgt ccgattcagt 660
catgcccgcg accccatctt cggctaccag aacatccccg acaccgctat cctcagcgtg 720
gtgccatttc accacggctt cggcatgttc accacgctgg gctacttgat ctgcggcttt 780
cgggtcgtgc tcatgtaccg cttcgaggag gagctattct tgcgcagctt gcaagactat 840
aagattcaat ctgccctgct ggtgcccaca ctatttagct gcctcgctaa gagcactctc 900
atcgacaagt acgacctaag cagcttgcgc gagatcgcca gcggcggggc gccgctcagc 960
aaggaggtag gtgaggccgt ggccaaacgc ttccgcctac caggcatccg ccagggctat 1020
ggcctgacag aaacaaccaa cgccgtcatg atcacccccg aggggggaccg taagcctggc 1080 tcagtaggca aggtggtgcc cttcttcgag gctaaggtgg tagacttggt caccggtaag 1140
acactgggtg tgaaccagcg cggtgagctg tgcgtccgtg gccccatgat catgagcggc 1200
tacgttaaca accccgaggc tacgaacgct ctcatcgaca aggacggctg gctgcacagc 1260
ggcgacatcg cctactggga cgaggacgag cacttcttca tcgtggaccg gctgaagagc 1320
ctgatcaaat acaagggcta ccaggtagcc ccagccgaac tggagggcat cctgctgcaa 1380
cacccctaca tcttcgacgc cggagtcgcc ggcctgcccg acgacgatgc cggcgagctg 1440
cccgccgcag tcgtcgtgtt ggaacacggt aaaaccatga ccgagaaaga gatcgtggac 1500
tatgtggcca gccaggttac aaccgccaag aagctgcgcg gtggtgttgt gtttgtggat 1560
gaagtcccta gaggatcgac cggcaagtta gacgcccgca agatccgcga gattctcact 1620
aaggccaaga aggacggcaa gatcgccgtg taa 1653

<210> SEQ ID NO 16
<211> LENGTH: 550
<212> TYPE: PRT
<213> ORGANISM: Artificial Sequence
<220> FEATURE:
<223> OTHER INFORMATION: Artificially mutated luciferase polypeptide

<400> SEQUENCE: 16

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Ala Ile Ala Phe Thr Asp Ala His Ile Gln
        35                  40                  45

Val Asp Val Thr Tyr Ala Glu Tyr Phe Glu Met Ser Val Arg Leu Ala
    50                  55                  60

-continued

```
Glu Ala Met Arg Arg Tyr Gly Leu Asn Thr Asn His Arg Ile Val Val
65                  70                  75                  80

Cys Ser Glu Asn Ser Ser Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Arg Lys Val Leu Asn Val Gln Lys Lys Leu Pro
    130                 135                 140

Ile Ile Arg Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Ser Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Tyr Gln Asn Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Cys Leu Ala Lys Ser Thr Leu Ile Asp Lys Tyr
    290                 295                 300

Asp Leu Ser Ser Leu Arg Glu Ile Ala Ser Gly Gly Ala Pro Leu Ser
305                 310                 315                 320

Lys Glu Val Gly Glu Ala Val Ala Lys Arg Phe Arg Leu Pro Gly Ile
                325                 330                 335

Arg Gln Gly Tyr Gly Leu Thr Glu Thr Thr Asn Ala Val Met Ile Thr
            340                 345                 350

Pro Glu Gly Asp Arg Lys Pro Gly Ser Val Gly Lys Val Val Pro Phe
        355                 360                 365

Phe Glu Ala Lys Val Val Asp Leu Val Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Gly Ile Leu Leu Gln His Pro Tyr Ile
    450                 455                 460

Phe Asp Ala Gly Val Ala Gly Leu Pro Asp Asp Asp Ala Gly Glu Leu
465                 470                 475                 480
```

```
Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Arg Gly Ser Thr Gly
        515                 520                 525

Lys Leu Asp Ala Arg Lys Ile Arg Glu Ile Leu Thr Lys Ala Lys Lys
    530                 535                 540

Asp Gly Lys Ile Ala Val
545                 550


<210> SEQ ID NO 17
<211> LENGTH: 171
<212> TYPE: PRT
<213> ORGANISM: Artificial Sequence
<220> FEATURE:
<223> OTHER INFORMATION: Artificially mutated luciferase polypeptide

<400> SEQUENCE: 17

Glu Phe Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170


<210> SEQ ID NO 18
<211> LENGTH: 171
<212> TYPE: PRT
<213> ORGANISM: Artificial Sequence
<220> FEATURE:
<223> OTHER INFORMATION: Artificially mutated luciferase polypeptide

<400> SEQUENCE: 18

Met Val Leu Thr Leu Glu Asp Phe Val Gly Asp Trp Arg Gln Thr Asp
1               5                   10                  15

Gly Tyr Asn Gln Ala Gln Val Leu Glu Gln Gly Gly Leu Thr Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60
```

```
Glu Gly Leu Ser Gly Asp Arg Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Gln Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Arg
    130                 135                 140

Ile Asn Pro Asp Gly Ser Leu Leu Phe Arg Val Thr Ile Asn Gly Val
145                 150                 155                 160

Thr Gly Trp Arg Leu Ser Glu Arg Ile Leu Ala
                165                 170
```

<210> SEQ ID NO 19
<211> LENGTH: 20
<212> TYPE: DNA
<213> ORGANISM: Artificial Sequence
<220> FEATURE:
<223> OTHER INFORMATION: Artificial oligonucleotide promoter

<400> SEQUENCE: 19
atgccatagc atttttatcc 20

<210> SEQ ID NO 20
<211> LENGTH: 18
<212> TYPE: DNA
<213> ORGANISM: Artificial Sequence
<220> FEATURE:
<223> OTHER INFORMATION: Artificial oligonucleotide promoter

<400> SEQUENCE: 20
gatttaatct gtatcagg 18

<210> SEQ ID NO 21
<211> LENGTH: 29
<212> TYPE: DNA
<213> ORGANISM: Artificial Sequence
<220> FEATURE:
<223> OTHER INFORMATION: Artificial oligonucleotide promoter

<400> SEQUENCE: 21
taccgagctc atccagtttg gactagtgg 29

<210> SEQ ID NO 22
<211> LENGTH: 31
<212> TYPE: DNA
<213> ORGANISM: Artificial Sequence
<220> FEATURE:
<223> OTHER INFORMATION: Artificial oligonucleotide promoter

<400> SEQUENCE: 22
agcccagatc tcctctagag tctagatctg g 31

<210> SEQ ID NO 23
<211> LENGTH: 52
<212> TYPE: DNA
<213> ORGANISM: Artificial Sequence
<220> FEATURE:
<223> OTHER INFORMATION: Artificial oligonucleotide promoter

<400> SEQUENCE: 23
aaagccaccg gcgcgccgcc gccaccatgg tcttcactct cgaagatttt gt 52

<210> SEQ ID NO 24
<211> LENGTH: 38
<212> TYPE: DNA
<213> ORGANISM: Artificial Sequence
<220> FEATURE:
<223> OTHER INFORMATION: Artificial oligonucleotide promoter

<400> SEQUENCE: 24
tcgaagcggc cggccttacg ccagaatgcg ttcatgca 38

<210> SEQ ID NO 25
<211> LENGTH: 51
<212> TYPE: DNA
<213> ORGANISM: Artificial Sequence
<220> FEATURE:
<223> OTHER INFORMATION: Artificial oligonucleotide promoter

<400> SEQUENCE: 25
aaagccaccg gcgcgccgcc gccaccatgg aagatgccaa aaacattaag a 51

<210> SEQ ID NO 26
<211> LENGTH: 42
<212> TYPE: DNA
<213> ORGANISM: Artificial Sequence
<220> FEATURE:
<223> OTHER INFORMATION: Artificial oligonucleotide promoter

<400> SEQUENCE: 26
tcgaagcggc cggccttaca cggcgatctt gccgtccttc tt 42

<210> SEQ ID NO 27
<211> LENGTH: 48
<212> TYPE: DNA
<213> ORGANISM: Artificial Sequence
<220> FEATURE:
<223> OTHER INFORMATION: Artificial oligonucleotide promoter

<400> SEQUENCE: 27
aaagccaccg gcgcgccgcc gccaccatgg cttccaaggt gtacgacc 48

<210> SEQ ID NO 28
<211> LENGTH: 41
<212> TYPE: DNA
<213> ORGANISM: Artificial Sequence
<220> FEATURE:
<223> OTHER INFORMATION: Artificial oligonucleotide promoter

<400> SEQUENCE: 28
tcgaagcggc cggccttact gctcgttctt cagcacgcgc t 41

<210> SEQ ID NO 29
<211> LENGTH: 48
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (19)..(20)
<223> OTHER INFORMATION: n is a, c, g, t or u
<220> FEATURE:
<221> NAME/KEY: misc_feature
<222> LOCATION: (22)..(23)
<223> OTHER INFORMATION: n is a, c, g, t or u

<400> SEQUENCE: 29
cagacagccg gctacaacnn knnkcaagtc cttgaacagg gaggtgtg 48

<210> SEQ ID NO 30
<211> LENGTH: 48
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (26)..(27)
<223> OTHER INFORMATION: n is a, c, g, t or u
<220> FEATURE:
<221> NAME/KEY: misc_feature
<222> LOCATION: (29)..(30)
<223> OTHER INFORMATION: n is a, c, g, t or u

<400> SEQUENCE: 30
cacacctccc tgttcaagga cttgmnnmnn gttgtagccg gctgtctg 48

<210> SEQ ID NO 31
<211> LENGTH: 51
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (22)..(23)
<223> OTHER INFORMATION: n is a, c, g, t or u
<220> FEATURE:
<221> NAME/KEY: misc_feature
<222> LOCATION: (25)..(26)
<223> OTHER INFORMATION: n is a, c, g, t or u
<220> FEATURE:
<221> NAME/KEY: misc_feature
<222> LOCATION: (28)..(29)
<223> OTHER INFORMATION: n is a, c, g, t or u

<400> SEQUENCE: 31
caagtccttg aacagggagg tnnknnknnk ttgtttcaga atctcggggt g 51

<210> SEQ ID NO 32
<211> LENGTH: 51
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (23)..(24)
<223> OTHER INFORMATION: n is a, c, g, t or u
<220> FEATURE:
<221> NAME/KEY: misc_feature
<222> LOCATION: (26)..(27)
<223> OTHER INFORMATION: n is a, c, g, t or u
<220> FEATURE:
<221> NAME/KEY: misc_feature
<222> LOCATION: (29)..(30)
<223> OTHER INFORMATION: n is a, c, g, t or u

<400> SEQUENCE: 32
caccccgaga ttctgaaaca amnnmnnmnn acctccctgt tcaaggactt g 51

<210> SEQ ID NO 33
<211> LENGTH: 20
<212> TYPE: DNA
<213> ORGANISM: Artificial Sequence
<220> FEATURE:
<223> OTHER INFORMATION: Artificial oligonucleotide promoter

<400> SEQUENCE: 33
atgccatagc atttttatcc 20

<210> SEQ ID NO 34
<211> LENGTH: 18
<212> TYPE: DNA
<213> ORGANISM: Artificial Sequence
<220> FEATURE:
<223> OTHER INFORMATION: Artificial oligonucleotide promoter

<400> SEQUENCE: 34
gatttaatct gtatcagg 18

<210> SEQ ID NO 35
<211> LENGTH: 43
<212> TYPE: DNA
<213> ORGANISM: Artificial Sequence
<220> FEATURE:
<223> OTHER INFORMATION: Artificial oligonucleotide promoter

<400> SEQUENCE: 35
aataaagctt gccgccacca tggtcttcac tctcggggat ttt 43

<210> SEQ ID NO 36
<211> LENGTH: 35
<212> TYPE: DNA
<213> ORGANISM: Artificial Sequence
<220> FEATURE:
<223> OTHER INFORMATION: Artificial oligonucleotide promoter

<400> SEQUENCE: 36
taattctcga gttacgccag aatgcgttca tgcag 35

<210> SEQ ID NO 37
<211> LENGTH: 46
<212> TYPE: DNA
<213> ORGANISM: Artificial Sequence
<220> FEATURE:
<223> OTHER INFORMATION: Artificial oligonucleotide promoter

<400> SEQUENCE: 37
attataaagc ttgccgccac catggaagat gccaaaaaca ttaaga 46

<210> SEQ ID NO 38
<211> LENGTH: 36
<212> TYPE: DNA
<213> ORGANISM: Artificial Sequence
<220> FEATURE:
<223> OTHER INFORMATION: Artificial oligonucleotide promoter

<400> SEQUENCE: 38
ataactcgag catggaagat gccaaaaaca ttaaga 36

<210> SEQ ID NO 39
<211> LENGTH: 36
<212> TYPE: DNA
<213> ORGANISM: Artificial Sequence
<220> FEATURE:
<223> OTHER INFORMATION: Artificial oligonucleotide promoter

<400> SEQUENCE: 39
ttgccaagct tacacggcga tcttgccgtc cttctt 36

<210> SEQ ID NO 40

<211> LENGTH: 44
<212> TYPE: DNA
<213> ORGANISM: Artificial Sequence
<220> FEATURE:
<223> OTHER INFORMATION: Artificial oligonucleotide promoter

<400> SEQUENCE: 40
attataaagc ttgccgccac catggtgagc aagggcgagg cagt 44

<210> SEQ ID NO 41
<211> LENGTH: 35
<212> TYPE: DNA
<213> ORGANISM: Artificial Sequence
<220> FEATURE:
<223> OTHER INFORMATION: Artificial oligonucleotide promoter

<400> SEQUENCE: 41
ataactcgag catggtgagc aagggcgagg cagtg 35

<210> SEQ ID NO 42
<211> LENGTH: 32
<212> TYPE: DNA
<213> ORGANISM: Artificial Sequence
<220> FEATURE:
<223> OTHER INFORMATION: Artificial oligonucleotide promoter

<400> SEQUENCE: 42
ttgccaagct tacgccagaa tgcgttcatg ca 32

<210> SEQ ID NO 43
<211> LENGTH: 45
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (22)..(23)
<223> OTHER INFORMATION: n is a, c, g, t or u

<400> SEQUENCE: 43
gagggccgcc actccaccgg annkactctc ggggattttg ttggg 45

<210> SEQ ID NO 44
<211> LENGTH: 45
<212> TYPE: DNA
<213> ORGANISM: Artificial Sequence
<220> FEATURE:
<223> OTHER INFORMATION: Artificial oligonucleotide promoter
<220> FEATURE:
<221> NAME/KEY: misc_feature
<222> LOCATION: (23)..(24)
<223> OTHER INFORMATION: n is a, c, g, t or u

<400> SEQUENCE: 44
cccaacaaaa tccccgagag tmnntccggt ggagtggcgg ccctc 45

<210> SEQ ID NO 45
<211> LENGTH: 38
<212> TYPE: DNA
<213> ORGANISM: Artificial Sequence
<220> FEATURE:
<223> OTHER INFORMATION: Artificial oligonucleotide promoter

<400> SEQUENCE: 45
ttattctcga gttacacggc gatcttgccg tccttctt 38